(12) United States Patent
Grady et al.

(10) Patent No.: US 8,969,055 B2
(45) Date of Patent: Mar. 3, 2015

(54) METHOD FOR PRODUCING BUTANOL USING EXTRACTIVE FERMENTATION WITH ELECTROLYTE ADDITION

(71) Applicant: Butamax Advanced Biofuels LLC, Wilmington, DE (US)

(72) Inventors: Michael Charles Grady, Oakland, NJ (US); Ranjan Patnaik, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/085,157

(22) Filed: Nov. 20, 2013

(65) Prior Publication Data

US 2014/0080189 A1 Mar. 20, 2014

Related U.S. Application Data

(62) Division of application No. 12/952,480, filed on Nov. 23, 2010, now Pat. No. 8,617,861.

(60) Provisional application No. 61/263,519, filed on Nov. 23, 2009.

(51) Int. Cl.
| | |
|---|---|
| *C12P 7/16* | (2006.01) |
| *C12N 9/00* | (2006.01) |
| *C12N 1/00* | (2006.01) |
| *C12N 1/20* | (2006.01) |
| *C12N 15/00* | (2006.01) |
| *C12N 5/00* | (2006.01) |
| *C07C 29/86* | (2006.01) |
| *C12N 1/28* | (2006.01) |
| *C12M 1/00* | (2006.01) |

(52) U.S. Cl.
CPC . *C12P 7/16* (2013.01); *C07C 29/86* (2013.01); *C12N 1/28* (2013.01); *C12M 47/10* (2013.01); *Y02E 50/10* (2013.01)
USPC ........ 435/160; 435/183; 435/243; 435/252.3; 435/320.1; 435/325; 568/918

(58) Field of Classification Search
None
See application file for complete search history.

(56) References Cited

U.S. PATENT DOCUMENTS

| | | | |
|---|---|---|---|
| 4,865,973 | A | 9/1989 | Kollerup et al. |
| 7,541,173 | B2 | 6/2009 | Bramucci et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0171129 | A1 | 7/2009 | Evanko et al. |
| 2009/0269823 | A1 | 10/2009 | Bramucci et al. |
| 2009/0305363 | A1 | 12/2009 | Anthony |
| 2009/0305370 | A1 | 12/2009 | Grady et al. |
| 2010/0081154 | A1 | 4/2010 | Flint et al. |
| 2010/0081179 | A1 | 4/2010 | Anthony et al. |
| 2010/0120105 | A1 | 5/2010 | Anthony et al. |
| 2010/0197519 | A1 | 8/2010 | Li et al. |
| 2011/0097773 | A1 | 4/2011 | Grady et al. |

FOREIGN PATENT DOCUMENTS

| | | |
|---|---|---|
| WO | 2007050671 | 3/2007 |
| WO | 2007041269 | 4/2007 |
| WO | 2007130518 | 11/2007 |
| WO | 2007130521 | 11/2007 |
| WO | 2007146377 | 12/2007 |

OTHER PUBLICATIONS

Amann et al., "Tightly regulated tac promoter vectors useful for the expression of unfused and fused proteins in *Escherichia coli*", Gene, vol. 69 (1988) pp. 301-315.
Atsumi et al., "Non-fermentative pathways for synthesis of branched-chain higher alcohols as biofuels", Nature, vol. 451, No. 3, Jan. 3, 2008, pp. 86-90.
Baba et al., "Construction of *Escherichia coli* K-12 in-frame, single-gene knockout mutants: the keio collection", Molecular Systems Biology (2006) vol. 2, pp. 1-11.
Cosquer et al., "Nanomolar levels of dimethylsulfoniopropionate, dimethylsulfonioacetate, and glycine betaine are sufficient to confer osmoprotection to *Escherichia coli*", Applied and Environmental Microbiology, Aug. 1999, vol. 65, No. 8, pp. 3304-3311.
Datsenko et al., "One-step inactivation of chromosomal genes in *Escherichia coli* K-12 using PCR products", PNAS, vol. 97, No. 12, Jun. 6, 2000, pp. 6640-6645.
De Carvalho et al., "*Mycobacterium* sp., *Rhodococcus erythropolis*, and *Pseudomonas putida* behavior in the presence of organic solvents", Microscopy Research and Technique, vol. 64, pp. 215-222 (2004).
Flikweert et al., "Pyruvate decarboxylase: an indispensable enzyme for growth of *Saccharomyces cerevisiae* on glucose", Yeast (1996) vol. 12, pp. 247-257.
Hermann et al., "Isolation and characterization of butanol-resistant mutants of *Clostridium acetobutylicum* ", Applied and Environmental Microbiology, vol. 50, No. 5, Nov. 1985, pp. 1238-1243.
Hohmann, "Characterisation of PDC2, a gene necessary for high level expression of pyruvate decarboxylase structural genes in *Saccharomyces cerevisiae*", Mol. Gen. Genet. (1993) vol. 241, pp. 657-666.

(Continued)

*Primary Examiner* — Christian Fronda

(57) ABSTRACT

A method for producing butanol through microbial fermentation, in which the butanol product is removed during the fermentation by extraction into a water-immiscible organic extractant in the presence of at least one electrolyte at a concentration at least sufficient to increase the butanol partition coefficient relative to that in the presence of the salt concentration of the basal fermentation medium, is provided. The electrolyte may comprise a salt which dissociates in the fermentation medium, or in the aqueous phase of a biphasic fermentation medium, to form free ions. Also provided is a method and composition for recovering butanol from a fermentation medium.

19 Claims, 7 Drawing Sheets

(56) References Cited

OTHER PUBLICATIONS

Figure 1:
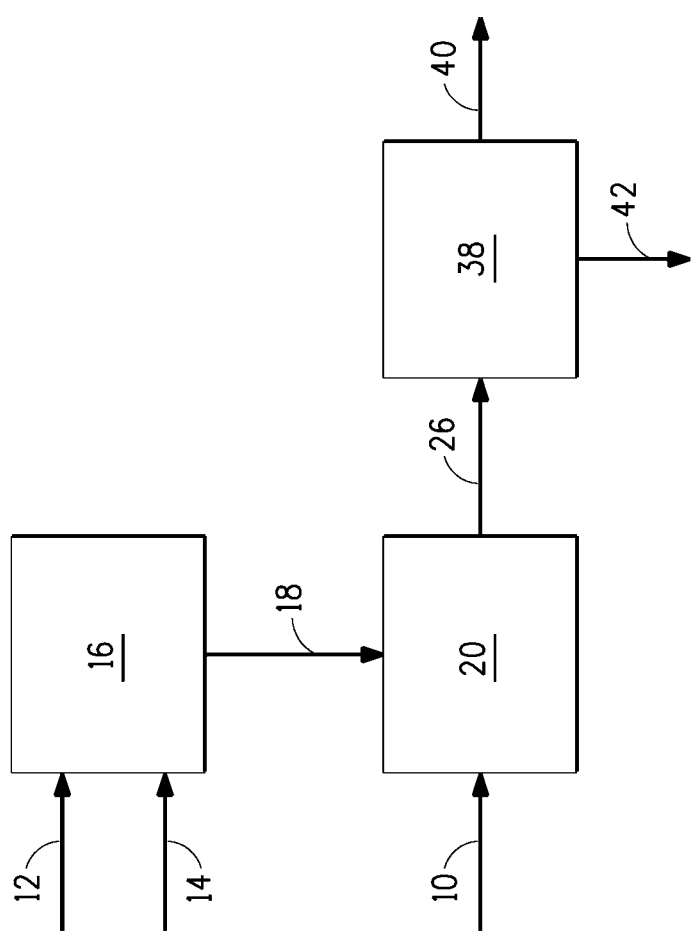

Kabelitz et al., "Effect of aliphatic alcohols on growth and degree of saturation of membrane lipids in *Acinetobacter calcoaceticus*", FEMS Microbiology Letters, vol. 220 (2003), pp. 223-227.
Malinowski et al., "Salt effects in extraction of ethanol, 1-butanol and acetone from aqueous solutions", AIChE Journal, vol. 40, No. 9, Sep. 1994, pp. 1459-1465.
Tomas et al., "Transcriptional analysis of butanol stress and tolerance in *Clostridium acetobutylicum*", Journal of Bacteriology, Apr. 2004, vol. 186, No. 7, pp. 2006-2018.
Methods in Yeast Genetics, 2005, Cold Spring Harbor Laboratory Press, Cold Spring Harbor, NY, pp. 201-202.
Ezeji et al., "Butanol fermentation research: upstream and downstream manipulations", The Chemical Record, vol. 4, pp. 305-314 (2004).
Adhami et al., "Liquid-liquid extraction of butanol from dilute aqueous solutions using soybean-derived biodiesel", J. Am. Oil Chem. Soc. (2009) vol. 86, pp. 1123-1128.
Malinowski et al., "Liquid-liquid and vapour-liquid behaviour of oleyl alcohol applied to extractive fermentation processing", The Canadian Journal of Chemical Engineering, vol. 71, Jun. 1993, pp. 431-436.
Banik, et al., Technological Aspects of Extractive Fermentation using Aqueous Two-phase Systems, World J Microbiol Biotechnol 19(4):337-348, 2003.
Barba, et al., Hyperazeotropic Ethanol Salted-out by Extractive Distillation. Theoretical Evaluation and Experimental Check, Chem. Engineer. Sci. 40(12):2287-2292, 1985.
Belafi-Bako, et al., Product removal in ethanol und ABE fermentations Produktabzug bei der Ethanol- und ABE-Fermentation, Hung. J. Ind. Chemical 23:309-319, 1995 (Abstract).
Carolan, et al., The Effect of Additives und Impurities on the Partition of Ethanol into n_Decanol from Aqueous Solutions, Dev. Chem. Eng. Mineral Process. 8:551-569, 2000.
Carolan, et al., Whole broth ethanol extraction: Partition studies, IChemE Research Event, European Conference for Young Researchers in Chemical Engineering, Apr. 1996 (Abstract).
Ezeji, et al., Production of acetone, butanol and ethanol by *Clostridium beijerinckii* BA101 and in situ recovery by gas stripping, World J Microbiol Biotech 19(6):595-603, 2003.

Harden, et al., The Salt Effect in Alcoholic Fermentation, Biochem. J. 15:312-318, 1921.
Kirk, et al., The Effects of Potassium and Chloride Ions on the Ethanolic Fermentation of Sucrose by *Zymomonas mobilis* 2716, Appl. Microbiol. Biotechnol. 37(1):88-93, 1992.
Lin, et al., Sulfate Effect on Fermentative Hydrogen Production using Anaerobic Mixed Microflora, Intl J Hydrogen Energy 31(7):953-960, 2006.
Naganagouda, et al., Aqueous Two-phase Extraction (ATPE):An Attractive and Economically Viable Technology for Downstream Processing . . . , Process Biochem. 43(11):1293-1299, 2008.
Pfennig, et al., Influence of Electrolytes on Liquid-Liquid Extraction, Ind. Eng. Chem. Res. 37(8):3180-3188, 1998.
Qureshi, et al., Butanol Production from Wheat Straw by Simultaneous Saccharification and Fermentation using *Clostridium beijerinckii*, Biomass and Bioenergy 32:168-175, 2008.
Tanuja, et al., Aqueous Two-phase Extraction Coupled with Ultrafiltration for Purification of Amyloglucosidases, Bioprocess Engineering 23(1):63-68, 2000.
Vane, Separation Technologies for the Recovery and Dehydration of Alcohols from Fermentation Broths, Biofuels, Bioprod. Bioref. 2:553-588, 2008.
Zhang, et al., Aqueous two-phase extraction of 2,3-butanediol from fermentation broth, Guocheng Gongcheng Xuebao 8:897-900, 2008 (Abstract).
Chica, et al., Semi-rational approaches to engineering enzyme activity: combining the benefits of directed evolution and rational design, Curr. Opin. Biotechnol. 16(4):378-384, 2005.
Sen, et al., Developments in Directed Evolution for Improving Enzyme Functions, Appl. Biochem. Biotechnol. 143 (3):212-23, 2007.
International Search Report and Written Opinion of corresponding PCT/US2010/057791 mailed May 4, 2011.
U.S. Appl. No. 12/893,077, filed Sep. 29, 2010.
U.S. Appl. No. 12/893,089, filed Sep. 29, 2010.
U.S. Appl. No. 12/980,597, filed Dec. 29, 2010.
U.S. Appl. No. 12/980,607, filed Dec. 29, 2010.
U.S. Appl. No. 61/379,546, filed Sep. 2, 2010.
U.S. Appl. No. 61/380,563, filed Sep. 7, 2010.
U.S. Appl. No. 13/029,558, filed Feb. 17, 2011.
U.S. Appl. No. 61/356,379, filed Jun. 18, 2010.
U.S. Appl. No. 61/368,429, filed Jul. 28, 2010.
Parent Application, U.S. Appl. No. 12/952,480, filed Nov. 23, 2010.

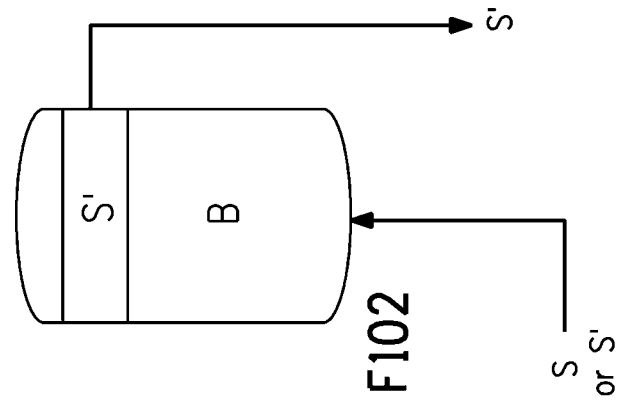
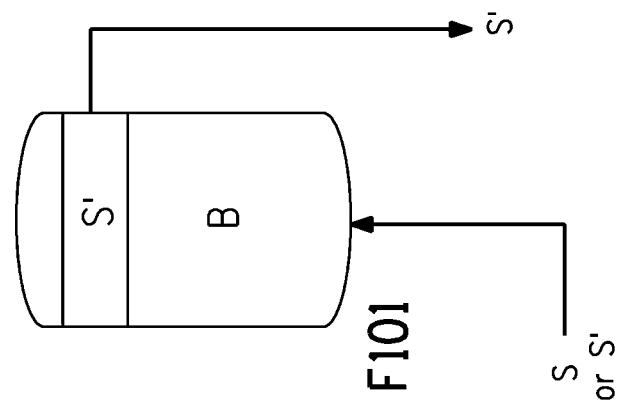
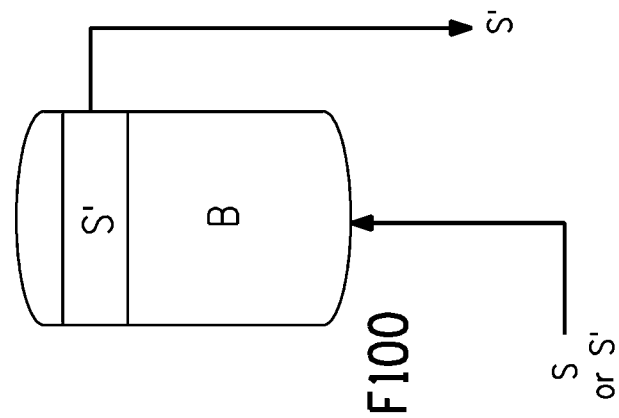
FIG. 7

METHOD FOR PRODUCING BUTANOL USING EXTRACTIVE FERMENTATION WITH ELECTROLYTE ADDITION

CROSS-REFERENCE TO RELATED APPLICATIONS

This application is a divisional of U.S. patent application Ser. No. 12/952,480, filed Nov. 23, 2010 which claims the benefit of priority to the U.S. Provisional Patent Application Ser. No. 61/263,519, filed on Nov. 23, 2009, the entirety of which is herein incorporated by reference.

FIELD OF THE INVENTION

The present invention relates to the field of biofuels. More specifically, the invention relates to a method for producing butanol through microbial fermentation, in which at least one electrolyte is present in the fermentation medium at a concentration at least sufficient to increase the butanol partition coefficient relative to that in the presence of the salt concentration of the basal fermentation medium, and the butanol product is removed by extraction into a water-immiscible organic extractant.

BACKGROUND

Butanol is an important industrial chemical with a variety of applications, such as use as a fuel additive, as a blend component to diesel fuel, as a feedstock chemical in the plastics industry, and as a foodgrade extractant in the food and flavor industry. Each year 10 to 12 billion pounds of butanol are produced by petrochemical means. As the need for butanol increases, interest in producing this chemical from renewable resources such as corn, sugar cane, or cellulosic feeds by fermentation is expanding.

In a fermentative process to produce butanol, in situ product removal advantageously reduces butanol inhibition of the microorganism and improves fermentation rates by controlling butanol concentrations in the fermentation broth. Technologies for in situ product removal include stripping, adsorption, pervaporation, membrane solvent extraction, and liquid-liquid extraction. In liquid-liquid extraction, an extractant is contacted with the fermentation broth to partition the butanol between the fermentation broth and the extractant phase. The butanol and the extractant are recovered by a separation process, for example by distillation.

J. J. Malinowski and A. J. Daugulis, AIChE Journal (1994), 40(9), 1459-1465, disclose experimental studies to assess the effect of salt addition on the extraction of 1-butanol, ethanol, and acetone from dilute aqueous solutions using cyclopentanol, n-valeraldehyde, tert-amyl alcohol, and Adol 85NF (comprised largely of oleyl alcohol) as extractants. The authors note in their conclusions that in spite of the advantages that salt addition offers to the extraction of ethanol, 1-butanol, and acetone from dilute aqueous solutions typically found in fermentation processes, the practical implementation of such a process configuration is presently limited. As an in situ recovery strategy (extractive fermentation) the relatively high salts concentrations which may be required could have severely deleterious effects on cells arising from osmotic shock.

Published Patent Application US 2009/0171129 A1 discloses methods for recovery of C3-C6 alcohols from dilute aqueous solutions, such as fermentation broths. The method includes increasing the activity of the C3-C6 alcohol in a portion of the aqueous solution to at least that of saturation of the C3-C6 alcohol in the portion. According to an embodiment of the invention, increasing the activity of the C3-C6 alcohol may comprise adding a hydrophilic solute to the aqueous solution. Sufficient hydrophilic solute is added to enable the formation of a second liquid phase, either solely by addition of the hydrophilic solute or in combination with other process steps. The added hydrophilic solute may be a salt, an amino acid, a water-soluble solvent, a sugar or combinations of those.

U.S. patent application Ser. No. 12/478,389 filed on Jun. 4, 2009, discloses methods for producing and recovering butanol from a fermentation broth, the methods comprising the step of contacting the fermentation broth with a water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, to form a two-phase mixture comprising an aqueous phase and a butanol-containing organic phase.

U.S. Provisional Patent Application Nos. 61/168,640; 61/168,642; and 61/168,645; filed concurrently on Apr. 13, 2009; and 61/231,697; 61/231,698; and 61/231,699; filed concurrently on Aug. 6, 2009, disclose methods for producing and recovering butanol from a fermentation medium, the methods comprising the step of contacting the fermentation medium with a water-immiscible organic extractant comprising a first solvent and a second solvent, the first solvent being selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof, and the second solvent being selected from the group consisting of $C_7$ to $C_{11}$ alcohols, $C_7$ to $C_{11}$ carboxylic acids, esters of $C_7$ to $C_{11}$ carboxylic acids, $C_7$ to $C_{11}$ aldehydes, and mixtures thereof, to form a two-phase mixture comprising an aqueous phase and a butanol-containing organic phase.

Improved methods for producing and recovering butanol from a fermentation medium are continually sought. A process for in situ product removal of butanol in which electrolyte addition to a fermentation medium provides improved butanol extraction efficiency and acceptable biocompatibility with the microorganism is desired.

SUMMARY OF THE INVENTION

The present invention provides a method for recovering butanol from a fermentation medium comprising butanol, water, at least one electrolyte, and a genetically modified microorganism that produces butanol from at least one fermentable carbon source. The electrolyte is present in the fermentation medium at a concentration at least sufficient to increase the butanol partition coefficient relative to that in the presence of the salt concentration of the basal fermentation medium. The present invention also provides methods for the production of butanol using such a microorganism and an added electrolyte. The methods include contacting the fermentation medium with i) a first water-immiscible organic extractant and optionally ii) a second water-immiscible organic extractant, separating the butanol-containing organic phase from the organic phase, and recovering the butanol from the butanol-containing organic phase. In one embodiment of the invention, a method for recovering butanol from a fermentation medium is provided, the method comprising:

a) providing a fermentation medium comprising butanol, water, at least one electrolyte at a concentration at least sufficient to increase the butanol partition coefficient relative to that in the presence of the salt concentration of the basal fermentation medium, and a genetically modified microorganism that produces butanol from at least one fermentable carbon source;

b) contacting the fermentation medium with i) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally ii) a second water-immiscible organic extractant selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides and mixtures thereof to form a two-phase mixture comprising an aqueous phase and a butanol-containing organic phase;

c) optionally, separating the butanol-containing organic phase from the aqueous phase; and d) recovering the butanol from the butanol-containing organic phase to produce recovered butanol.

In some embodiments, a portion of the butanol is concurrently removed from the fermentation medium by a process comprising the steps of: a) stripping butanol from the fermentation medium with a gas to form a butanol-containing gas phase; and b) recovering butanol from the butanol-containing gas phase.

According to the methods of the invention, the electrolyte may be added to the fermentation medium, to the first extractant, to the optional second extractant, or to combinations thereof. In some embodiments, the electrolyte comprises a salt having a cation selected from the group consisting of lithium, sodium, potassium, rubidium, cesium, magnesium, calcium, strontium, barium, ammonium, phosphonium, and combinations thereof. In some embodiments, the electrolyte comprises a salt having an anion selected from the group consisting of sulfate, carbonate, acetate, citrate, lactate, phosphate, fluoride, chloride, bromide, iodide, and combinations thereof. In some embodiments, the electrolyte is selected from the group consisting of sodium sulfate, sodium chloride, and combinations thereof.

According to the methods of the invention, in some embodiments the genetically modified microorganism is selected from the group consisting of bacteria, cyanobacteria, filamentous fungi, and yeasts. In some embodiments, the bacteria are selected from the group consisting of *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium,* and *Brevibacterium*. In some embodiments the yeast is selected from the group consisting of *Pichia, Candida, Hansenula, Kluyveromyces, Issatchenkia,* and *Saccharomyces*.

According to the methods of the invention, the first extractant may be selected from the group consisting of oleyl alcohol, behenyl alcohol, cetyl alcohol, lauryl alcohol, myristyl alcohol, stearyl alcohol, oleic acid, lauric acid, myristic acid, stearic acid, methyl myristate, methyl oleate, lauric aldehyde, 1-dodecanol, and a combination of these. In some embodiments, the first extractant comprises oleyl alcohol. In some embodiments, the second extractant may be selected from the group consisting of 1-nonanol, 1-decanol, 1-undecanol, 2-undecanol, 1-nonanal, and a combination of these.

In some embodiments, the butanol is 1-butanol. In some embodiments, the butanol is 2-butanol. In some embodiments, the butanol is isobutanol. In some embodiments, the fermentation medium further comprises ethanol, and the butanol-containing organic phase contains ethanol.

In one embodiment of the invention, a method for the production of butanol is provided, the method comprising:

a) providing a genetically modified microorganism that produces butanol from at least one fermentable carbon source;

b) growing the microorganism in a biphasic fermentation medium comprising an aqueous phase and i) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally ii) a second water-immiscible organic extractant selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides, and mixtures thereof, wherein the biphasic fermentation medium further comprises at least one electrolyte at a concentration at least sufficient to increase the butanol partition coefficient relative to that in the presence of the salt concentration of the basal fermentation medium, for a time sufficient to allow extraction of the butanol into the organic extractant to form a butanol-containing organic phase;

c) optionally, separating the butanol-containing organic phase from the aqueous phase; and d) recovering the butanol from the butanol-containing organic phase to produce recovered butanol.

In one embodiment of the invention, a method for the production of butanol is provided, the method comprising:

a) providing a genetically modified microorganism that produces butanol from at least one fermentable carbon source;

b) growing the microorganism in a fermentation medium wherein the microorganism produces the butanol into the fermentation medium to produce a butanol-containing fermentation medium;

c) adding at least one electrolyte to the fermentation medium to provide the electrolyte at a concentration at least sufficient to increase the butanol partition coefficient relative to that in the presence of the salt concentration of the basal fermentation medium;

d) contacting at least a portion of the butanol-containing fermentation medium with i) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally ii) a second water-immiscible organic extractant selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides, and mixtures thereof, to form a two-phase mixture comprising an aqueous phase and a butanol-containing organic phase;

e) optionally, separating the butanol-containing organic phase from the aqueous phase;

f) recovering the butanol from the butanol-containing organic phase; and g) optionally, returning at least a portion of the aqueous phase to the fermentation medium.

In some embodiments, the genetically modified microorganism comprises a modification which inactivates a competing pathway for carbon flow. In some embodiments the genetically modified microorganism does not produce acetone.

BRIEF DESCRIPTION OF THE FIGURES AND SEQUENCE DESCRIPTIONS

FIG. 1 schematically illustrates one embodiment of the methods of the invention, in which the first extractant and the second extractant are combined in a vessel prior to contacting with the fermentation medium in a fermentation vessel.

Figure 2:
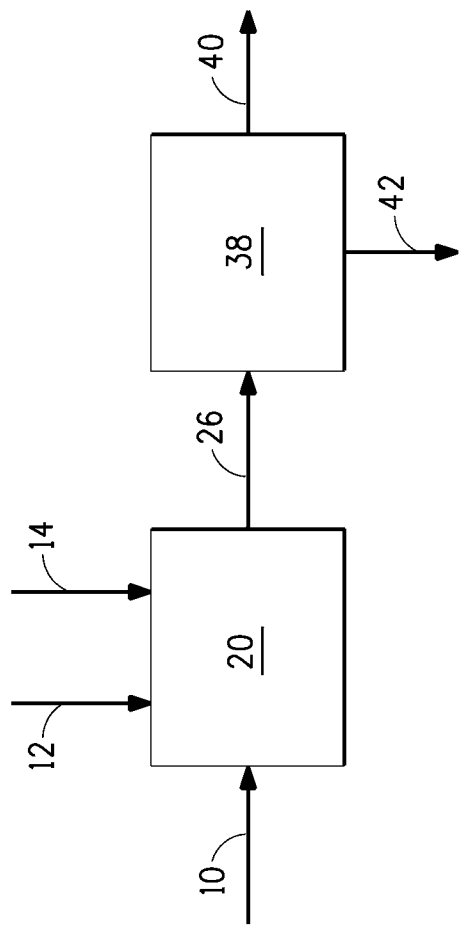

FIG. 2 schematically illustrates one embodiment of the methods of the invention, in which the first extractant and the second extractant are added separately to a fermentation vessel in which the fermentation medium is contacted with the extractants.

Figure 3:
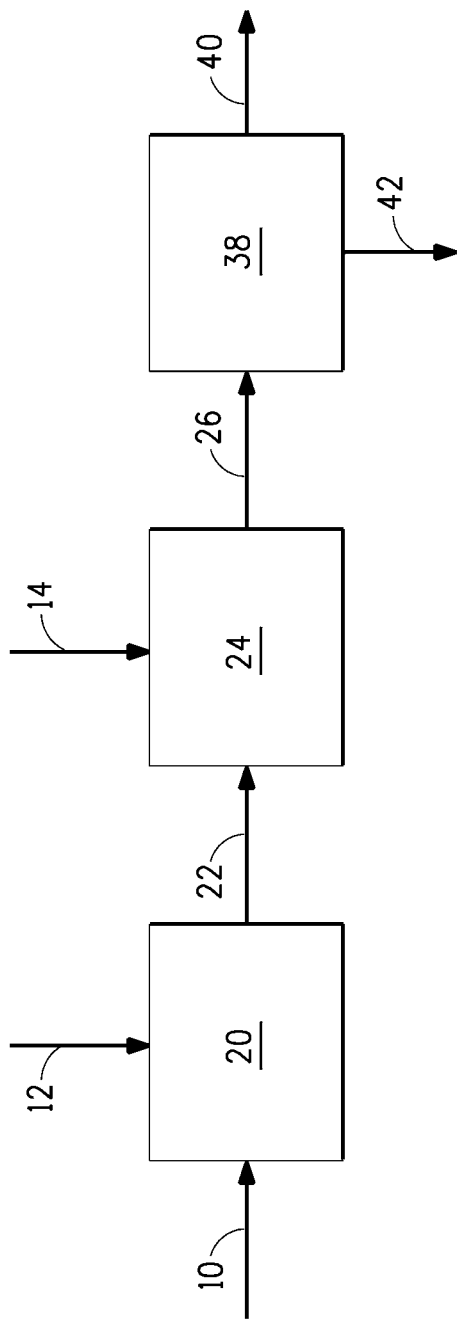

FIG. 3 schematically illustrates one embodiment of the methods of the invention, in which the first extractant and the second extractant are added separately to different fermentation vessels.

Figure 4:
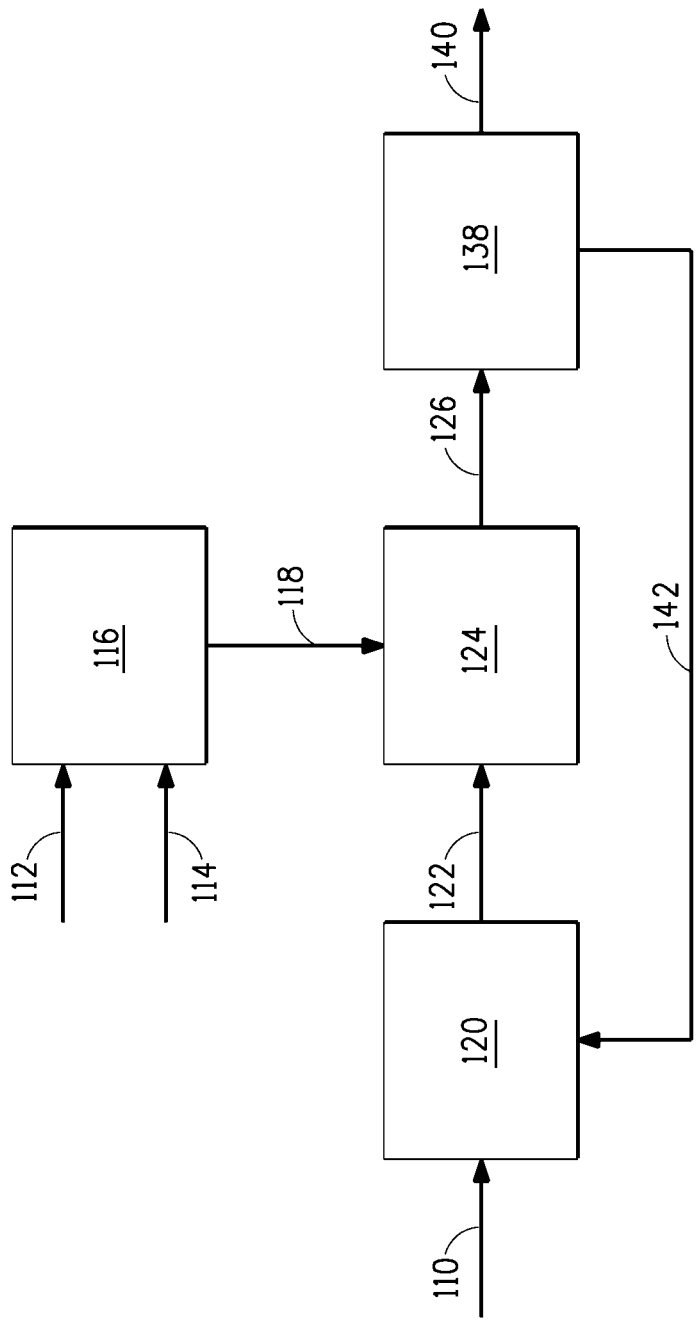

FIG. 4 schematically illustrates one embodiment of the methods of the invention, in which extraction of the product occurs downstream of the fermentor and the first extractant and the second extractant are combined in a vessel prior to contacting the fermentation medium with the extractants in a different vessel.

Figure 5:
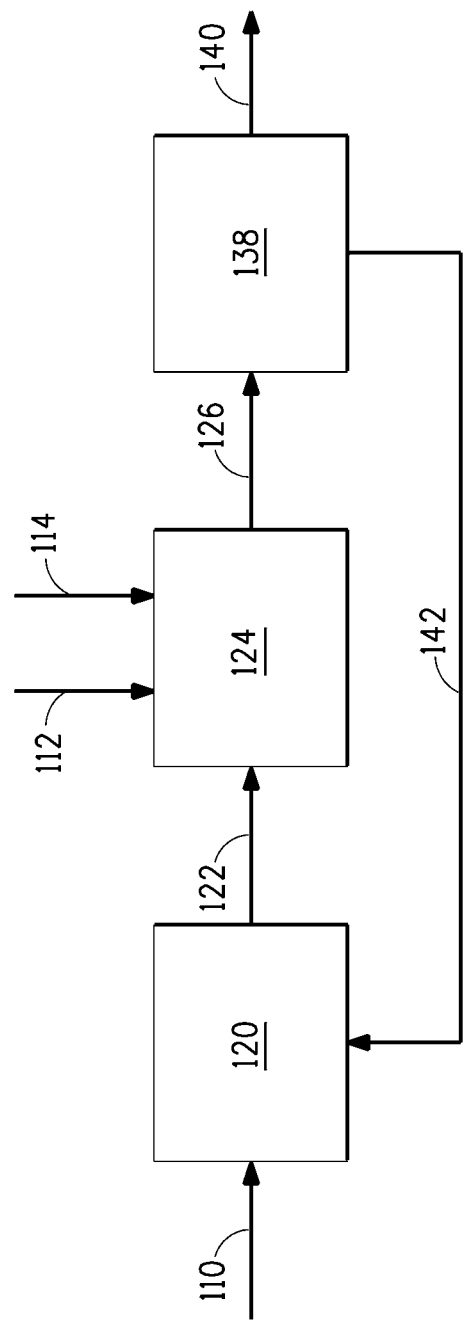

FIG. 5 schematically illustrates one embodiment of the methods of the invention, in which extraction of the product occurs downstream of the fermentor and the first extractant and the second extractant are added separately to a vessel in which the fermentation medium is contacted with the extractants.

Figure 6:
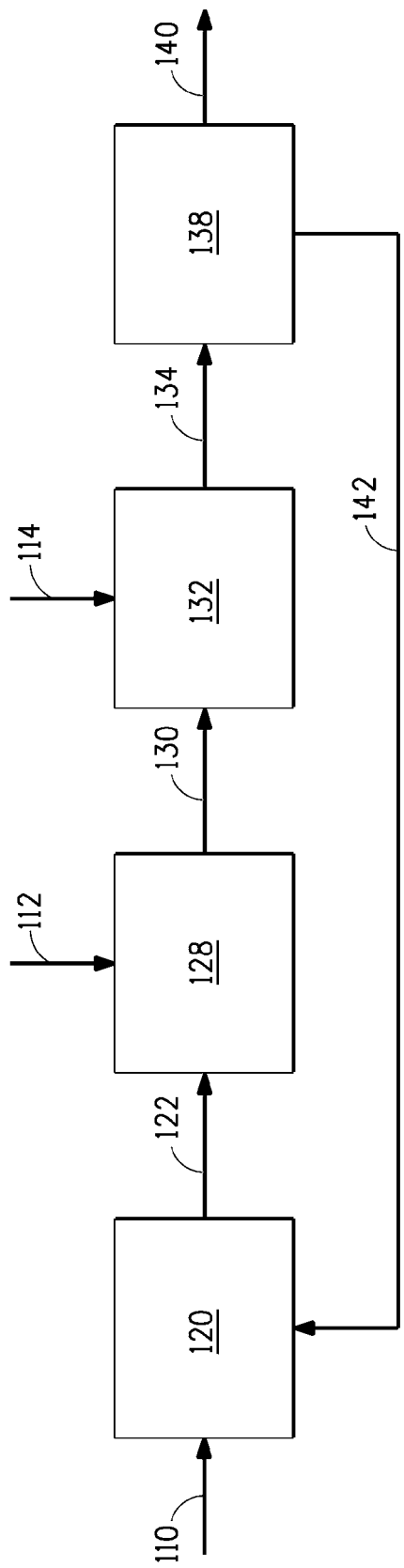

FIG. 6 schematically illustrates one embodiment of the methods of the invention, in which extraction of the product occurs downstream of the fermentor and the first extractant and the second extractant are added separately to different vessels for contacting with the fermentation medium.

FIG. 7 schematically illustrates one embodiment of the methods of the invention, in which extraction of the product occurs in at least one batch fermentor via co-current flow of a water-immiscible organic extractant at or near the bottom of a fermentation mash to fill the fermentor with extractant which flows out of the fermentor at a point at or near the top of the fermentor.

The following sequences conform with 37 C.F.R. 1.821 1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a bis), and Section 208 and Annex C of the Administrative Instructions).

TABLE 1a

SEQ ID Numbers of Coding Sequences and Proteins

| Description | SEQ ID NO: Nucleic acid | SEQ ID NO: Amino acid |
|---|---|---|
| *Klebsiella pneumonias* budB (acetolactate synthase) | 1 | 2 |
| *E. coli* ilvC (acetohydroxy acid reductoisomerase) | 3 | 4 |
| *E. coli* ilvD (acetohydroxy acid dehydratase) | 5 | 6 |
| *Lactococcus lactis* kivD (branched-chain α-keto acid decarboxylase) | 7 (codon optimized) | 8 |
| *Achromobacter xylosoxidans* sadB (butanol dehydrogenase) | 9 | 10 |
| *Bacillus subtilis* alsS (acetolactate synthase) | 11 | 12 |
| *S. cerevisiae* ILV5 (acetohydroxy acid reductoisomerase; "KARI") | 13 | 14 |

TABLE 1a-continued

SEQ ID Numbers of Coding Sequences and Proteins

| Description | SEQ ID NO: Nucleic acid | SEQ ID NO: Amino acid |
|---|---|---|
| Mutant KARI (encoded by Pf5.ilvC-Z4B8) | 15 | 16 |
| *Streptococcus mutans* ilvD (acetohydroxy acid dehydratase) | 17 | 18 |
| *Bacillus subtilis* kivD (branched-chain keto acid decarboxylase) | 19 (codon optimized) | 20 |
| Horse liver alcohol dehydrogenase (HADH) | 56 (codon optimized) | 57 |
| *E. coli* pflB (pyruvate formate lyase) | 71 | 70 |
| *E. coli* frdB (subunit of fumarate reductase enzyme complex) | 73 | 72 |
| *E. coli* ldhA (lactate dehydrogenase) | 77 | 76 |
| *E. coli* adhE (alcohol dehydrogenase) | 75 | 74 |
| *E. coli* frdA (subunit of fumarate reductase enzyme complex) | 91 | 90 |
| *E. coli* frdC (subunit of fumarate reductase enzyme complex) | 93 | 92 |
| *E. coli* frdD (subunit of fumarate reductase enzyme complex) | 95 | 94 |

TABLE 1b

SEQ ID Numbers of Sequences used in construction, Primers and Vectors

| Description | SEQ ID NO: |
|---|---|
| pRS425::GPM-sadB | 63 |
| GPM-sadB-ADHt segment | 21 |
| pUC19-URA3r | 22 |
| 114117-11A | 23 |
| 114117-11B | 24 |
| 114117-11C | 25 |
| 114117-11D | 26 |
| 114117-13A | 27 |
| 114117-13B | 28 |
| 112590-34F | 29 |
| 112590-34G | 30 |
| 112590-34H | 31 |
| 112590-49E | 32 |
| ilvD-FBA1t segment | 33 |
| 114117-27A | 34 |
| 114117-27B | 35 |
| 114117-27C | 36 |
| 114117-27D | 37 |
| 114117-36D | 38 |
| 135 | 39 |
| 112590-30F | 40 |
| URA3r2 template | 41 |
| 114117-45A | 42 |
| 114117-45B | 43 |
| PDC5::KanMXF | 44 |
| PDC5::KanMXR | 45 |
| PDC5kofor | 46 |
| N175 | 47 |
| pLH475-Z4B8 plasmid | 48 |
| CUP1 promoter | 49 |
| CYC1 terminator CYC1-2 | 50 |
| ILV5 promoter | 51 |
| ILV5 terminator | 52 |
| FBA1 promoter | 53 |
| CYC1 terminator | 54 |
| pLH468 plasmid | 55 |
| Vector pNY8 | 58 |
| GPD1 promoter | 59 |
| GPD1 promoter fragment | 60 |
| OT1068 | 61 |
| OT1067 | 62 |
| GPM1 promoter | 64 |
| ADH1 terminator | 65 |
| OT1074 | 66 |
| OT1075 | 67 |
| pRS423 FBA ilvD(*Strep*) | 68 |

TABLE 1b-continued

SEQ ID Numbers of Sequences used in construction, Primers and Vectors

| Description | SEQ ID NO: |
| --- | --- |
| FBA terminator | 69 |
| pflB CkUp | 78 |
| pflB CkDn | 79 |
| frdB CkUp | 80 |
| frdB CkDn | 81 |
| ldhA CkUp | 82 |
| ldhA CkDn | 83 |
| adhE CkUp | 84 |
| adhE CkDn | 85 |
| N473 | 86 |
| N469 | 87 |
| N695A | 88 |
| N695B | 89 |

DETAILED DESCRIPTION

The present invention provides methods for recovering butanol from a microbial fermentation medium comprising at least one electrolyte by extraction into a water-immiscible organic extractant to form a two-phase mixture comprising an aqueous phase and a butanol-containing organic phase. The electrolyte is present in the fermentation medium at a concentration at least sufficient to increase the butanol partition coefficient relative to that in the presence of the salt concentration of the basal fermentation medium. The butanol-containing organic phase is separated from the aqueous phase and the butanol may be recovered. Methods for producing butanol are also provided.

DEFINITIONS

The following definitions are used in this disclosure.

The term "electrolyte" refers to a solute that ionizes or dissociates in an aqueous solution and may function as an ionic conductor.

The term "butanol" refers to 1-butanol, 2-butanol, and/or isobutanol, individually or as mixtures thereof.

The term "water-immiscible" refers to a chemical component, such as an extractant or solvent, which is incapable of mixing with an aqueous solution, such as a fermentation broth, in such a manner as to form one liquid phase.

The term "extractant" as used herein refers to one or more organic solvents which are used to extract butanol from a fermentation broth.

The term "biphasic fermentation medium" refers to a two-phase growth medium comprising a fermentation medium (i.e., an aqueous phase) and a suitable amount of a water-immiscible organic extractant.

The term "organic phase", as used herein, refers to the non-aqueous phase of a biphasic mixture obtained by contacting a fermentation broth with a water-immiscible organic extractant.

The term "aqueous phase", as used herein, refers to the phase of a biphasic mixture, obtained by contacting an aqueous fermentation medium with a water-immiscible organic extractant, which comprises water.

The term "In Situ Product Removal" as used herein means the selective removal of a specific fermentation product from a biological process such as fermentation to control the product concentration in the biological process.

The term "fermentation broth" as used herein means the mixture of water, sugars, dissolved solids, suspended solids, microorganisms producing butanol, product butanol and all other constituents of the material held in the fermentation vessel in which product butanol is being made by the reaction of sugars to butanol, water and carbon dioxide ($CO_2$) by the microorganisms present. The fermentation broth may comprise one or more fermentable carbon sources such as the sugars described herein. The fermentation broth is the aqueous phase in biphasic fermentative extraction. From time to time, as used herein the term "fermentation medium" may be used synonymously with "fermentation broth".

The term "fermentation vessel" as used herein means the vessel in which the fermentation reaction by which product butanol is made from sugars is carried out. The term "fermentor" may be used synonymously herein with "fermentation vessel".

The term "fermentable carbon source" refers to a carbon source capable of being metabolized by the microorganisms disclosed herein. Suitable fermentable carbon sources include, but are not limited to, monosaccharides, such as glucose or fructose; disaccharides, such as lactose or sucrose; oligosaccharides; polysaccharides, such as starch or cellulose; one-carbon substrates; and a combination of these, which may be found in the fermentation medium. Sources of fermentable carbon include renewable carbon, that is non-petroleum-based carbon, including carbon from agricultural feedstocks, algae, cellulose, hemicellulose, lignocellulose, or any combination thereof.

The term "fatty acid" as used herein refers to a carboxylic acid having a long, aliphatic chain of $C_7$ to $C_{22}$ carbon atoms, which is either saturated or unsaturated.

The term "fatty alcohol" as used herein refers to an alcohol having a long, aliphatic chain of $C_7$ to $C_{22}$ carbon atoms, which is either saturated or unsaturated.

The term "fatty aldehyde" as used herein refers to an aldehyde having a long, aliphatic chain of $C_7$ to $C_{22}$ carbon atoms, which is either saturated or unsaturated.

The term "fatty amide" as used herein refers to an amide having a long, aliphatic chain of $C_{12}$ to $C_{22}$ carbon atoms, which is either saturated or unsaturated.

The term "partition coefficient", abbreviated herein as $K_p$, means the ratio of the concentration of a compound in the two phases of a mixture of two immiscible solvents at equilibrium. A partition coefficient is a measure of the differential solubility of a compound between two immiscible solvents. As used herein, the term "partition coefficient for butanol" refers to the ratio of concentrations of butanol between the organic phase comprising the extractant and the aqueous phase comprising the fermentation medium. Partition coefficient, as used herein, is synonymous with the term distribution coefficient.

The term "separation" as used herein is synonymous with "recovery" and refers to removing a chemical compound from an initial mixture to obtain the compound in greater purity or at a higher concentration than the purity or concentration of the compound in the initial mixture.

The term "butanol biosynthetic pathway" as used herein refers to an enzyme pathway to produce 1-butanol, 2-butanol, or isobutanol.

The term "1-butanol biosynthetic pathway" as used herein refers to an enzyme pathway to produce 1-butanol from acetyl-coenzyme A (acetyl-CoA).

The term "2-butanol biosynthetic pathway" as used herein refers to an enzyme pathway to produce 2-butanol from pyruvate.

The term "isobutanol biosynthetic pathway" as used herein refers to an enzyme pathway to produce isobutanol from pyruvate.

The term "effective titer" as used herein, refers to the total amount of butanol produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of butanol produced by fermentation per liter of fermentation medium per hour of fermentation.

The term "effective yield" as used herein, refers to the amount of butanol produced per unit of fermentable carbon substrate consumed by the biocatalyst The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "minimal media" as used herein refers to growth media that contain the minimum nutrients possible for growth, generally without the presence of amino acids. A minimal medium typically contains a fermentable carbon source and various salts, which may vary among microorganisms and growing conditions; these salts generally provide essential elements such as magnesium, nitrogen, phosphorus, and sulfur to allow the microorganism to synthesize proteins and nucleic acids.

The term "defined media" as used herein refers to growth media that have known quantities of all ingredients present, e.g., a defined carbon source and nitrogen source, and trace elements and vitamins required by the microorganism.

The term "biocompatibility" as used herein refers to the measure of the ability of a microorganism to utilize glucose in the presence of an extractant. A biocompatible extractant permits the microorganism to utilize glucose. A non-biocompatible (that is, a biotoxic) extractant does not permit the microorganism to utilize glucose, for example at a rate greater than about 25% of the rate when the extractant is not present.

The term, "° C." means degrees Celsius. The term "OD" means optical density. The term "$OD_{600}$" refers to the optical density at a wavelength of 600 nm. The term ATCC refers to the American Type Culture Collection, Manassas, Va. The term "sec" means second(s). The term "min" means minute(s). The term "h" means hour(s). The term "mL" means milliliter(s). The term "L" means liter. The term "g" means grams. The term "mmol" means millimole(s). The term "M" means molar. The term "µL" means microliter. The term "µg" means microgram. The term "µg/mL" means microgram per liter. The term "mL/min" means milliliters per minute. The term "g/L" means grams per liter. The term "g/L/h" means grams per liter per hour. The term "mmol/min/mg" means millimole per minute per milligram. The term "temp" means temperature. The term "rpm" means revolutions per minute. The term "HPLC" means high pressure gas chromatography. The term "GC" means gas chromatography.

All publications, patents, patent applications, and other references mentioned herein are expressly incorporated by reference in their entireties for all purposes. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Genetically Modified Microorganisms

Microbial hosts for butanol production may be selected from bacteria, cyanobacteria, filamentous fungi and yeasts. The microbial host used should be tolerant to the butanol product produced, so that the yield is not limited by toxicity of the product to the host. The selection of a microbial host for butanol production is described in detail below.

Microbes that are metabolically active at high titer levels of butanol are not well known in the art. Although butanol-tolerant mutants have been isolated from solventogenic *Clostridia*, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by butanol toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of butanol should be tolerant to butanol and should be able to convert carbohydrates to butanol using an introduced biosynthetic pathway, such as the pathway described below. The criteria for selection of suitable microbial hosts include the following: intrinsic tolerance to butanol, high rate of carbohydrate utilization, availability of genetic tools for gene manipulation, and the ability to generate stable chromosomal alterations.

Suitable host strains with a tolerance for butanol may be identified by screening based on the intrinsic tolerance of the strain. The intrinsic tolerance of microbes to butanol may be measured by determining the concentration of butanol that is responsible for 50% inhibition of the growth rate (IC50) when grown in a minimal medium. The IC50 values may be determined using methods known in the art. For example, the microbes of interest may be grown in the presence of various amounts of butanol and the growth rate monitored by measuring the optical density at 600 nanometers. The doubling time may be calculated from the logarithmic part of the growth curve and used as a measure of the growth rate. The concentration of butanol that produces 50% inhibition of growth may be determined from a graph of the percent inhibition of growth versus the butanol concentration. Preferably, the host strain should have an IC50 for butanol of greater than about 0.5%. More suitable is a host strain with an IC50 for butanol that is greater than about 1.5%. Particularly suitable is a host strain with an IC50 for butanol that is greater than about 2.5%.

The microbial host for butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that may be used include by electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also may be manipulated in order to inactivate competing pathways for carbon flow by inactivating various genes. This requires the availability of either transposons or chromosomal integration vectors to direct inactivation. Additionally, production hosts that are amenable to chemical mutagenesis may undergo improvements in intrinsic butanol tolerance through chemical mutagenesis and mutant screening.

As an example of inactivation of competing pathways for carbon flow, pyruvate decarboxylase may be reduced or eliminated (see, for example, US Patent Application Publication No. 20090305363). In embodiments, butanol is the major product of the microorganism. In embodiments, the microorganism does not produce acetone.

Based on the criteria described above, suitable microbial hosts for the production of butanol include, but are not limited to, members of the genera, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula, Kluyveromyces, Issatchenkia, and Saccharomyces. Preferred hosts include: Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Pediococcus pentosaceus, Pediococcus acidilactici, Bacillus subtilis and Saccharomyces cerevisiae.

Microorganisms mentioned above may be genetically modified to convert fermentable carbon sources into butanol, specifically 1-butanol, 2-butanol, or isobutanol, using methods known in the art. Suitable microorganisms include Escherichia, Lactobacillus, and Saccharomyces. Suitable microorganisms include E. coli, L. plantarum and S. cerevisiae. Additionally, the microorganism may be a butanol-tolerant strain of one of the microorganisms listed above that is isolated using the method described by Bramucci et al. (U.S. patent application Ser. No. 11/761,497; and WO 2007/146377). An example of one such strain is Lactobacillus plantarum strain PN0512 (ATCC: PTA-7727, biological deposit made Jul. 12, 2006 for U.S. patent application Ser. No. 11/761,497).

Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Likewise, certain suitable proteins having the ability to catalyze indicated substrate to product conversions are described herein and other suitable proteins are provided in the art. For example, US Patent Application Publication Nos. US20080261230, US20090163376, and US20100197519 describe acetohydroxy acid isomeroreductases as does U.S. application Ser. No. 12/893,077, filed on Sep. 29, 2010; US Patent Application Publication No. 20100081154 describes dihydroxyacid dehydratases; alcohol dehydrogenases are described in US Patent Application Publication No. US20090269823 and U.S. Provisional Patent Application No. 61/290,636.

Microorganisms can be genetically modified to contain a 1-butanol biosynthetic pathway to produce 1-butanol. Suitable modifications include those described by Donaldson et al. in WO 2007/041269. For example, the microorganism may be genetically modified to express a 1-butanol biosynthetic pathway comprising the following enzyme-catalyzed substrate to product conversions:
 a) acetyl-CoA to acetoacetyl-CoA;
 b) acetoacetyl-CoA to 3-hydroxybutyryl-CoA;
 c) 3-hydroxybutyryl-CoA to crotonyl-CoA;
 d) crotonyl-CoA to butyryl-CoA;
 e) butyryl-CoA to butyraldehyde; and
 f) butyraldehyde to a-butanol.

The microorganisms may also be genetically modified to express a 2-butanol biosynthetic pathway to produce 2-butanol. Suitable modifications include those described by Donaldson et al. in U.S. Patent Application Publication Nos. 2007/0259410 and 2007/0292927, and PCT Application Publication Nos. WO 2007/130518 and WO 2007/130521. For example, in one embodiment the microorganism may be genetically modified to express a 2-butanol biosynthetic pathway comprising the following enzyme-catalyzed substrate to product conversions:
 a) pyruvate to alpha-acetolactate;
 b) alpha-acetolactate to acetoin;
 c) acetoin to 2,3-butanediol;
 d) 2,3-butanediol to 2-butanone; and
 e) 2-butanone to 2-butanol.

The microorganisms may also be genetically modified to express an isobutanol biosynthetic pathway to produce isobutanol. Suitable modifications include those described by Donaldson et al. in U.S. Patent Application Publication No. 2007/0092957 and WO 2007/050671. For example, the microorganism may be genetically modified to contain an isobutanol biosynthetic pathway comprising the following enzyme-catalyzed substrate to product conversions:
 a) pyruvate to acetolactate;
 b) acetolactate to 2,3-dihydroxyisovalerate;
 c) 2,3-dihydroxyisovalerate to α-ketoisovalerate;
 d) α-ketoisovalerate to isobutyraldehyde; and
 e) isobutyraldehyde to isobutanol.

The Escherichia coli strain may comprise: (a) an isobutanol biosynthetic pathway encoded by the following genes: budB (SEQ ID NO:1) from Klebsiella pneumoniae encoding acetolactate synthase (given as SEQ ID NO:2), ilvC (given as SEQ ID NO:3) from E. coli encoding acetohydroxy acid reductoisomerase (given as SEQ ID NO:4), ilvD (given as SEQ ID NO:5) from E. coli encoding acetohydroxy acid dehydratase (given as SEQ ID NO:6), kivD (given as SEQ ID NO:7) from Lactococcus lactis encoding the branched-chain keto acid decarboxylase (given as SEQ ID NO:8), and sadB (given as SEQ ID NO:9) from Achromobacter xylosoxidans encoding a butanol dehydrogenase (given as SEQ ID NO:10). The enzymes encoded by the genes of the isobutanol biosynthetic pathway catalyze the substrate to product conversions for converting pyruvate to isobutanol, as described above. Specifically, acetolactate synthase catalyzes the conversion of pyruvate to acetolactate, acetohydroxy acid reductoisomerase catalyzes the conversion of acetolactate to 2,3-dihydroxyisovalerate, acetohydroxy acid dehydratase catalyzes the conversion of 2,3-dihydroxyisovalerate to α-ketoisovalerate, branched-chain keto acid decarboxylase catalyzes the conversion of α-ketoisovalerate to isobutyraldehyde, and butanol dehydrogenase catalyzes the conversion of isobutyraldehyde to isobutanol. This recombinant Escherichia coli strain can be constructed using methods known in the art (see copending U.S. patent application Ser. Nos.

12/478,389 and 12/477,946) and/or described herein below. It is contemplated that suitable strains may be constructed comprising a sequence having at least about 70-75% identity, at least about 75-80%, at least about 80-85% identity, or at least about 85-90% identity to protein sequences described herein.

The *Escherichia coli* strain may comprise deletions of the following genes to eliminate competing pathways that limit isobutanol production, pflB, given as SEQ ID No: 71, (encoding for pyruvate formate lyase) IdhA, given as SEQ IS NO: 73, (encoding for lactate dehydrogenase), adhE, given as SEQ IS NO: 77, (encoding for alcohol dehydrogenase), and at least one gene comprising the frdABCD operon (encoding for fumarate reductase), specifically, frdA, given as SEQ ID NO: 90, frdB, given as SEQ ID NO: 75, frdC, given as SEQ ID NO: 92, and frdD, given as SEQ ID NO: 94.

The *Saccharomyces cerevisiae* strain may comprise: an isobutanol biosynthetic pathway encoded by the following genes: alsS coding region from *Bacillus subtilis* (SEQ ID NO:11) encoding acetolactate synthase (SEQ ID NO:12), ILV5 from *S. cerevisiae* (SEQ ID NO:13) encoding acetohydroxy acid reductoisomerase (KARI; SEQ ID NO:14) and/or a mutant KARI such as encoded by Pf5.IlvC-Z4B8 (SEQ ID NO: 15; protein SEQ ID NO: 16), ilvD from *Streptococcus mutans* (SEQ ID NO: 17) encoding acetohydroxy acid dehydratase (SEQ ID NO: 18), kivD from *Bacillus subtilis* (codon optimized sequence given as SEQ ID NO: 19) encoding the branched-chain keto acid decarboxylase (SEQ ID NO:20), and sadB from *Achromobacter xylosoxidans* (SEQ ID NO:9) encoding a butanol dehydrogenase (SEQ ID NO:10). The enzymes encoded by the genes of the isobutanol biosynthetic pathway catalyze the substrate to product conversions for converting pyruvate to isobutanol, as described herein. It is contemplated that suitable strains may be constructed comprising a sequence having at least about 70-75% identity, at least about 75-80%, at least about 80-85% identity, or at least about 85-90% identity to protein sequences described herein.

A yeast strain expressing an isobutanol pathway with acetolactate synthase (ALS) activity in the cytosol and deletions of the endogenous pyruvate decarboxylase (PDC) genes is described in U.S. patent application Ser. No. 12/477,942. This combination of cytosolic ALS and reduced PDC expression has been found to greatly increase flux from pyruvate to acetolactate, which then flows to the pathway for production of isobutanol. Such a recombinant *Saccharomyces cerevisiae* strain can be constructed using methods known in the art and/or described herein. Other suitable yeast strains are known in the art. Additional examples are provided in U.S. Provisional Application Ser. Nos. 61/379,546, 61/380,563, and U.S. application Ser. No. 12/893,089.

Additional modifications suitable for microorganisms used in conjunction with the processes provided herein include modifications to reduce glycerol-3-phosphate dehydrogenase activity as described in US Patent Application Publication No. 20090305363, modifications to a host cell that provide for increased carbon flux through an Entner-Doudoroff Pathway or reducing equivalents balance as described in US Patent Application Publication No. 20100120105. Yeast strains with increased activity of heterologous proteins that require binding of an Fe—S cluster for their activity are described in US Application Publication No. 20100081179. Other modifications include modifications in an endogenous polynucleotide encoding a polypeptide having dual-role hexokinase activity, described in U.S. Provisional Application No. 61/290,639, integration of at least one polynucleotide encoding a polypeptide that catalyzes a step in a pyruvate-utilizing biosynthetic pathway described in U.S. Provisional Application No. 61/380,563.

Additionally, host cells comprising at least one deletion, mutation, and/or substitution in an endogenous gene encoding a polypeptide affecting Fe—S cluster biosynthesis are described in U.S. Provisional Patent Application No. 61/305,333, and host cells comprising a heterologous polynucleotide encoding a polypeptide with phosphoketolase activity and host cells comprising a heterologous polynucleotide encoding a polypeptide with phosphotransacetylase activity are described in U.S. Provisional Patent Application No. 61/356,379.

Construction of a Suitable Yeast Strain

NGI-049 is an example of a suitable *Saccharomyces cerevisiae* strain. NGI-049 is a strain with insertion-inactivation of endogenous PDC1, PDC5, and PDC6 genes, and containing expression vectors pLH475-Z4B8 and pLH468. PDC1, PDC5, and PDC6 genes encode the three major isozymes of pyruvate decarboxylase. The strain expresses genes encoding enzymes for an isobutanol biosynthetic pathway that are integrated or on plasmids. Construction of the NGI-049 strain is provided herein.

Endogenous pyruvate decarboxylase activity in yeast converts pyruvate to acetaldehyde, which is then converted to ethanol or to acetyl-CoA via acetate. Therefore, endogenous pyruvate decarboxylase activity is a target for reduction or elimination of byproduct formation.

Examples of other yeast strains with reduced pyruvate decarboxylase activity due to disruption of pyruvate decarboxylase encoding genes have been reported such as for *Saccharomyces* in Flikweert et al. (Yeast (1996) 12:247-257), for *Kluyveromyces* in Bianchi et al. (Mol. Microbiol. (1996) 19(1):27-36), and disruption of the regulatory gene in Hohmann, (Mol Gen Genet. (1993) 241:657-666). *Saccharomyces* strains having no pyruvate decarboxylase activity are available from the ATCC (Accession #200027 and #200028).

Construction of pdc6::GPMp1-sadB Integration Cassette and PDC6 Deletion:

A pdc6::GPM1p-sadB-ADH1t-URA3r integration cassette was made by joining the GPM-sadB-ADHt segment (SEQ ID NO:21) from pRS425::GPM-sadB (SEQ ID NO: 63) to the URA3r gene from pUC19-URA3r. pUC19-URA3r (SEQ ID NO:22) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) Gene 77:61-68) using as template pRS425::GPM-sadB and pUC19-URA3r plasmid DNAs, with Phusion DNA polymerase (New England Biolabs Inc., Beverly, Mass.; catalog no. F-540S) and primers 114117-11A through 114117-11D (SEQ ID NOs:23, 24, 25 and 26), and 114117-13A and 114117-13B (SEQ ID NOs:27 and 28).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 112590-34G and 112590-34H (SEQ ID NOs:30 and 31), and 112590-34F and 112590-49E (SEQ ID NOs: 29 and 32) to verify integration at the PDC6 locus with deletion of the PDC6 coding region. The URA3r marker was recycled by plating on synthetic complete media supplemented with 2% glucose and 5-FOA at 30° C.

following standard protocols. Marker removal was confirmed by patching colonies from the 5-FOA plates onto SD-URA media to verify the absence of growth. The resulting identified strain has the genotype: BY4700 pdc6::P$_{GPM1}$-sadB-ADH1t.

Construction of pdc1::PDC1-ilvD Integration Cassette and PDC1 Deletion:

A pdc1::PDC1p-ilvD-FBA1t-URA3r integration cassette was made by joining the ilvD-FBA1t segment (SEQ ID NO:33) from pLH468 to the URA3r gene from pUC19-URA3r by SOE PCR (as described by Horton et al. (1989) Gene 77:61-68) using as template pLH468 and pUC19-URA3r plasmid DNAs, with Phusion DNA polymerase (New England Biolabs Inc., Beverly, Mass.; catalog no. F-540S) and primers 114117-27A through 114117-27D (SEQ ID NOs:34, 35, 36 and 37).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::P$_{GPM1}$-sadB-ADH1t and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 114117-36D and 135 (SEQ ID NOs 38 and 39), and primers 112590-49E and 112590-30F (SEQ ID NOs 32 and 40) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::GPM1p-sadB-ADH1t pdc1::PDC1p-ilvD-FBA1t.

HIS3 Deletion

To delete the endogenous HIS3 coding region, a his3::URA3r2 cassette was PCR-amplified from URA3r2 template DNA (SEQ ID NO; 41). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs: 42 and 43) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics*, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA73" has the genotype: BY4700 pdc6::GPM1p-sadB-ADH1t pdc1::PDC1p-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion DNA polymerase and primers PDC5::KanMXF and PDC5::KanMXR (SEQ ID NOs:44 and 45) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (*Methods in Yeast Genetics*, 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC locus with replacement of the PDC5 coding region using primers PDC5kofor and N175 (SEQ ID NOs: 46 and 47). The identified correct transformants have the genotype: BY4700 pdc6::GPM1p-sadB-ADH1t pdc1::PDC1p-ilvD-FBA1t Δhis3 pdc5::kanMX4.

pLH475-Z4B8 Construction

The pLH475-Z4B8 plasmid (SEQ ID NO:48) was constructed for expression of ALS and KARI in yeast. pLH475-Z4B8 is a pHR81 vector (ATCC #87541) containing the following chimeric genes: 1) the CUP1 promoter (SEQ ID NO: 49), acetolactate synthase coding region from *Bacillus subtilis* (AlsS; SEQ ID NO: 11; protein SEQ ID NO: 12) and CYC1 terminator (CYC1-2; SEQ ID NO: 50); 2) an ILV5 promoter (SEQ ID NO:51), Pf5.IlvC-Z4B8 coding region (SEQ ID NO: 15; protein SEQ ID NO: 16) and ILV5 terminator (SEQ ID NO:52); and 3) the FBA1 promoter (SEQ ID NO: 53), *S. cerevisiae* KARI coding region (ILV5; SEQ ID NO: 13; protein SEQ ID NO:14) and CYC1 terminator (SEQ ID NO: 54).

The Pf5.IlvC-Z4B8 coding region is a sequence encoding KARI derived from *Pseudomonas fluorescens* but containing mutations, that was described in US Patent Application Publication No. US20090163376. The Pf5.IlvC-Z4B8 encoded KARI (SEQ ID NO:16) has the following amino acid changes as compared to the natural *Pseudomonas fluorescens* KARI:

C33L: cysteine at position 33 changed to leucine,
R47Y: arginine at position 47 changed to tyrosine,
S50A: serine at position 50 changed to alanine,
T52D: threonine at position 52 changed to asparagine,
V53A: valine at position 53 changed to alanine,
L61F: leucine at position 61 changed to phenylalanine,
T80I: threonine at position 80 changed to isoleucine,
A156V: alanine at position 156 changed to threonine, and
G170A: glycine at position 170 changed to alanine.

The Pf5.IlvC-Z4B8 coding region was synthesized by DNA 2.0 (Palo Alto, Calif.; SEQ ID NO:15) based on codons that were optimized for expression in *Saccharomyces cerevisiae*.

Expression Vector pLH468

The pLH468 plasmid (SEQ ID NO: 55) was constructed for expression of DHAD, KivD and HADH in yeast.

Coding regions for *B. subtilis* ketoisovalerate decarboxylase (KivD) and Horse liver alcohol dehydrogenase (HADH) were synthesized by DNA2.0 based on codons that were optimized for expression in *Saccharomyces cerevisiae* (SEQ ID NO:19 and 56, respectively) and provided in plasmids pKivDy-DNA2.0 and pHadhy-DNA2.0. The encoded proteins are SEQ ID NOs 20 and 57, respectively. Individual expression vectors for KivD and HADH were constructed. To assemble pLH467 (pRS426::P$_{GPD1}$-kivDy-GPD1t), vector pNY8 (SEQ ID NO:58; also named pRS426.GPD-ald-GPDt, described in US Patent App. Pub. US20080182308, Example 17) was digested with AscI and SfiI enzymes, thus excising the GPD1 promoter (SEQ ID NO: 59) and the ald coding region. A GPD1 promoter fragment (GPD1-2; SEQ ID NO: 60) from pNY8 was PCR amplified to add an AscI site at the 5' end, and an SpeI site at the 3' end, using 5' primer OT1068 and 3' primer OT1067 (SEQ ID NOs: 61 and 62). The AscI/SfiI digested pNY8 vector fragment was ligated with the GPD1 promoter PCR product digested with AscI and SpeI, and the SpeI-SfiI fragment containing the codon optimized kivD coding region isolated from the vector pKivD-DNA2.0. The triple ligation generated vector pLH467 (PRS426::$P_{GPD1}$-kivDy-GPD1t). pLH467 was verified by restriction mapping and sequencing.

pLH435 (pRS425::$P_{GPM1}$-Hadhy-ADH1t) was derived from vector pRS425::GPM-sadB (SEQ ID NO:63) which is described in U.S. patent application Ser. No. 12/477,942, Example 3. pRS425::GPM-sadB is the pRS425 vector (ATCC #77106) with a chimeric gene containing the GPM1 promoter (SEQ ID NO:64), coding region from a butanol dehydrogenase of *Achromobacter xylosoxidans* (sadB; SEQ ID NO: 9; protein SEQ ID NO:10: disclosed in US Patent App. Publication No. US20090269823), and ADH1 terminator (SEQ ID NO:65). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO:66 and 67) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC #87474) was digested with SacI and NotI, and ligated with the SacI-SalI fragment from pLH467 that contains the $P_{GPD1}$-kivDy-GPD1t cassette together with the SalI-NotI fragment from pLH435 that contains the $P_{GPM1}$-Hadhy-ADH1t cassette in a triple ligation reaction. This yielded the vector pRS411::$P_{GPD1}$-kivDy-$P_{GPM1}$-Hadhy (pLH441), which was verified by restriction mapping.

In order to generate a co-expression vector for all three genes in the lower isobutanol pathway: ilvD, kivDy and Hadhy, we used pRS423 FBA ilvD(Strep) (SEQ ID NO:68), which is described in U.S. patent application Ser. No. 12/569,636 as the source of the IlvD gene. This shuttle vector contains an F1 origin of replication (nt 1423 to 1879) for maintenance in *E. coli* and a 2 micron origin (nt 8082 to 9426) for replication in yeast. The vector has an FBA promoter (nt 2111 to 3108; SEQ ID NO: 53;) and FBA terminator (nt 4861 to 5860; SEQ ID NO: 69). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 17; protein SEQ ID NO: 18) from *Streptococcus mutans* UA159 (ATCC #700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::$P_{FBA1}$-ilvD(Strep)Lumio-FBA1t-$P_{GPD1}$-kivDy-GPD1t-$P_{GPM1}$-hadhy-ADH1t), which was confirmed by restriction mapping and sequencing.

Plasmid vectors pLH468 and pLH475-Z4B8 were simultaneously transformed into strain BY4700 pdc6::GPM1p-sadB-ADH1t pdc1::PDC1p-ilvD-FBA1t Δhis3 pdc5::kanMX4 using standard genetic techniques (*Methods in Yeast Genetics*, 2005, Cold Spring Harbor Laboratory Press, Cold Spring Harbor, N.Y.) and the resulting strain was maintained on synthetic complete media lacking histidine and uracil, and supplemented with 1% ethanol at 30° C. The resulting strain was named NGI-049.

Organic Extractants

The extractant is a water-immiscible organic solvent or solvent mixture having characteristics which render it useful for the extraction of butanol from a fermentation broth. A suitable organic extractant should meet the criteria for an ideal solvent for a commercial two-phase extractive fermentation for the production or recovery of butanol. Specifically, the extractant should (i) be biocompatible with the microorganisms, for example *Escherichia coli*, *Lactobacillus plantarum*, and *Saccharomyces cerevisiae*, (ii) be substantially immiscible with the fermentation medium, (iii) have a high partition coefficient ($K_P$) for the extraction of butanol, (iv) have a low partition coefficient for the extraction of nutrients, (v) have a low tendency to form emulsions with the fermentation medium, and (vi) be low cost and nonhazardous. In addition, for improved process operability and economics, the extractant should (vii) have low viscosity ($\mu$), (viii) have a low density ($\rho$) relative to the aqueous fermentation medium, and (ix) have a boiling point suitable for downstream separation of the extractant and the butanol.

In one embodiment, the extractant may be biocompatible with the microorganism, that is, nontoxic to the microorganism or toxic only to such an extent that the microorganism is impaired to an acceptable level, so that the microorganism continues to produce the butanol product into the fermentation medium. The extent of biocompatibility of an extractant can be determined by the glucose utilization rate of the microorganism in the presence of the extractant and the butanol product, as measured under defined fermentation conditions. See, for example, the Examples in U.S. Provisional Patent Application Nos. 61/168,640; 61/168,642; and 61/168,645. While a biocompatible extractant permits the microorganism to utilize glucose, a non-biocompatible extractant does not permit the microorganism to utilize glucose at a rate greater than, for example, about 25% of the rate when the extractant is not present. As the presence of the fermentation product butanol can affect the sensitivity of the microorganism to the extractant, the fermentation product should be present during biocompatibility testing of the extractant. The presence of additional fermentation products, for example ethanol, may similarly affect the biocompatibility of the extractant. Use of a biocompatible extractant is desired for processes in which continued production of butanol is desired after contacting the fermentation broth comprising the microorganism with an organic extractant.

In one embodiment, the extractant may be selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides, and mixtures thereof. Examples of suitable extractants include an extractant comprising at least one solvent selected from the group consisting of oleyl alcohol, behenyl alcohol, cetyl alcohol, lauryl alcohol, myristyl alcohol, stearyl alcohol, oleic acid, lauric acid, myristic acid, stearic acid, methyl myristate, methyl oleate, lauric aldehyde, 1-nonanol, 1-decanol, 1-undecanol, 2-undecanol, 1-nonanal, 2-butyloctanol, 2-butyl-octanoic acid and mixtures thereof. In embodiments, the extractant comprises oleyl alcohol. In embodiments, the extractant comprises a branched chain saturated alcohol, for example, 2-butyloctanol, commercially available as ISOFAL® 12 (Sasol, Houston, Tex.) or Jarcol I-12 (Jarchem Industries, Inc., Newark, N.J.). In embodiments, the extractant comprises a branched chain carboxylic acid, for example, 2-butyl-octanoic acid, 2-hexyl-decanoic acid, or 2-decyl-tetradecanoic acid, commercially available as ISOCARB® 12, ISOCARB® 16, and ISOCARB® 24, respectively (Sasol, Houston, Tex.).

In one embodiment, a first water-immiscible organic extractant may be selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. Suitable first extractants may be further selected from the group consisting of oleyl alcohol, behenyl alcohol, cetyl alcohol, lauryl alcohol also referred to as 1-dodecanol, myristyl alcohol, stearyl alcohol, oleic acid, lauric acid, myristic acid, stearic acid, methyl myristate, methyl oleate, lauric aldehyde, and mixtures thereof. In one embodiment, the extractant may comprise oleyl alcohol.

In one embodiment, an optional second water-immiscible organic extractant may be selected from the group consisting of $C_7$ to $C_{22}$ fatty alcohols, $C_7$ to $C_{22}$ fatty carboxylic acids, esters of $C_7$ to $C_{22}$ fatty carboxylic acids, $C_7$ to $C_{22}$ fatty aldehydes, $C_7$ to $C_{22}$ fatty amides, and mixtures thereof. Suitable second extractants may be further selected from the group consisting of 1-nonanol, 1-decanol, 1-undecanol, 2-undecanol, 1-nonanal, and mixtures thereof. In one embodiment, the second extractant comprises 1-decanol.

In one embodiment, the first extractant comprises oleyl alcohol and the second extractant comprises 1-decanol.

When a first and a second extractant are used, the relative amounts of each can vary within a suitable range. For example, the first extractant may be used in an amount which is about 30 percent to about 90 percent, or about 40 percent to about 80 percent, or about 45 percent to about 75 percent, or about 50 percent to about 70 percent of the combined volume of the first and the second extractants. The optimal range reflects maximization of the extractant characteristics, for example balancing a relatively high partition coefficient for butanol with an acceptable level of biocompatibility. For a two-phase extractive fermentation for the production or recovery of butanol, the temperature, contacting time, butanol concentration in the fermentation medium, relative amounts of extractant and fermentation medium, specific first and second extractants used, relative amounts of the first and second extractants, presence of other organic solutes, the presence and concentration of electrolytes, and the amount and type of microorganism are related; thus these variables may be adjusted as necessary within appropriate limits to optimize the extraction process as described herein.

Suitable organic extractants may be available commercially from various sources, such as Sigma-Aldrich (St. Louis, Mo.), in various grades, many of which may be suitable for use in extractive fermentation to produce or recover butanol. Technical grades of a solvent can contain a mixture of compounds, including the desired component and higher and lower molecular weight components. For example, one commercially available technical grade oleyl alcohol contains about 65% oleyl alcohol and a mixture of higher and lower fatty alcohols.

Electrolyte

According to the present method, the fermentation medium contains at least one electrolyte at a concentration at least sufficient to increase the butanol partition coefficient relative to that in the presence of the salt concentration of the basal fermentation medium. The electrolyte may comprise one or more of the salts contained in the basal fermentation medium, in which case the electrolyte is present at a concentration above that of the concentration of the total salts contained in the basal fermentation medium. The electrolyte may comprise one or more salts which are not present in the basal fermentation medium. The basal fermentation medium may contain, for example, phosphate, magnesium, and/or ammonium salts and is generally tailored to a specific microorganism. Suggested compositions of basal fermentation media may be found in Difco™ & BBL™ manual (Becton Dickinson and Company, Sparks, Md. 21152, USA). Generally, the salts provided by trace elements may be ignored in the calculation of the total salt concentration of the basal fermentation medium due to their extremely low concentrations.

The electrolyte may comprise a salt which dissociates in the fermentation medium, or in the aqueous phase of a biphasic fermentation medium, to form free ions. For example, the electrolyte may comprise a salt having a cation selected from the group consisting of lithium, sodium, potassium, rubidium, cesium, magnesium, calcium, strontium, barium, ammonium, phosphonium, and combinations thereof. For example, the electrolyte may comprise a salt having an anion selected from the group consisting of sulfate, carbonate, acetate, citrate, lactate, phosphate, fluoride, chloride, bromide, iodide, and combinations thereof. The electrolyte may be selected from the group consisting of sodium sulfate, sodium chloride, and combinations thereof.

The electrolyte may be available commercially from various sources, such as Sigma-Aldrich (St. Louis, Mo.), in various grades, many of which may be suitable for use in extractive fermentation to produce or recover butanol by the methods disclosed herein. The electrolyte may be recovered by methods know in the art from a fermentation medium or from an aqueous phase formed by contacting the fermentation medium with an extractant or other physical or chemical methods such as precipitation, crystallization, and/or evaporation. The recovered electrolyte may be used in a subsequent fermentation.

The amount of electrolyte needed to achieve a concentration in the fermentation medium at least sufficient to increase the butanol partition coefficient relative to that in the presence of the salt concentration of the basal fermentation medium can be determined as disclosed, for example, by the procedures of the Examples herein below. The range of electrolyte concentrations which have a positive effect on the partition coefficient is determined, for example by experimentation. The range of electrolyte concentrations which demonstrate acceptable biocompatibility with the microorganism of interest is also determined. The range of suitable electrolyte concentrations are then selected from the overlap of these two ranges, such that the amount of electrolyte required to have a positive effect on the butanol partition coefficient is balanced with the concentration range that provides an acceptable level of biocompatibility with the microorganism. Economic considerations may also be a factor in selecting the amount of osmolyte to use.

In one embodiment, the electrolyte may be present in the fermentation medium at a concentration which is biocompatible with the microorganism, that is, nontoxic to the microorganism or toxic only to such an extent that the microorganism is impaired to an acceptable level, so that the microorganism continues to produce the butanol product into the fermentation medium in the presence of the electrolyte. The extent of biocompatibility of an electrolyte can be determined by the growth rate of the microorganism in the presence of varying concentrations of the electrolyte, as described in Example 2 herein below. While a biocompatible electrolyte concentration permits the microorganism to utilize glucose (or other carbon source) or grow, a non-biocompatible electrolyte concentration does not permit the microorganism to utilize glucose (or other carbon source) or grow at a rate greater than, for example, about 25% of the growth rate when the excess amount of electrolyte is not present. The presence of fermentation products, for example butanol, may also affect the concentration ranges of the electrolyte which have biocompatibility with the microorganism. Use of an electrolyte within concentration ranges having biocompatibility is desired for processes in which continued production of butanol is necessary after contacting the fermentation medium comprising the microorganism with the electrolyte. In processes in which continued production of butanol after contacting the fermentation medium comprising the microorganism with the electrolyte is not required, an electrolyte may be used at concentration ranges which have little, if any, biocompatibility with the microorganism.

To achieve a concentration in the fermentation medium of electrolyte which is at least sufficient to increase the butanol partition coefficient relative to that in the presence of the salt concentration of the basal fermentation medium, the electrolyte may be added to the fermentation medium or to the aqueous phase of a biphasic fermentation medium during the growth phase of the microorganism, during the butanol production phase, when the butanol concentration is inhibitory, or to combinations thereof. The electrolyte may be added to the first extractant, to the second extractant, or to combinations thereof. The electrolyte may be added as a solid, as a slurry, or as an aqueous solution. Optionally, the electrolyte may be added to both the fermentation medium and the extractant(s). The electrolyte may be added in a continuous, semi-continuous, or batch manner. The electrolyte may be added to the entire stream to which it is introduced, for example to the entire fermentation medium in a fermentor, or to a partial stream taken from one or more vessels, for example to a partial stream taken from a fermentor.

In embodiments, the total concentration of electrolyte in the fermentation medium is greater than about 0.05M, 0.1M, 0.2M, 0.3M, 0.4M, 0.5M, 0.6M, 0.7M, 0.8M, or 1M. In some embodiments, the concentration of electrolyte in the fermentation is less than about 1M, and in some embodiments, the concentration of electrolyte in the fermentation is less than 2M.

Fermentation

The microorganism may be cultured in a suitable fermentation medium in a suitable fermentor to produce butanol. Any suitable fermentor may be used including a stirred tank fermentor, an airlift fermentor, a bubble fermentor, or any combination thereof. Materials and methods for the maintenance and growth of microbial cultures are well known to those skilled in the art of microbiology or fermentation science (see for example, Bailey et al., *Biochemical Engineering Fundamentals*, second edition, McGraw Hill, New York, 1986). Consideration must be given to appropriate fermentation medium, pH, temperature, and requirements for aerobic, microaerobic, or anaerobic conditions, depending on the specific requirements of the microorganism, the fermentation, and the process. The fermentation medium used is not critical, but it must support growth of the microorganism used and promote the biosynthetic pathway necessary to produce the desired butanol product. A conventional fermentation medium may be used, including, but not limited to, complex media containing organic nitrogen sources such as yeast extract or peptone and at least one fermentable carbon source; minimal media; and defined media. Suitable fermentable carbon sources include, but are not limited to, monosaccharides, such as glucose or fructose; disaccharides, such as lactose or sucrose; oligosaccharides; polysaccharides, such as starch or cellulose; one carbon substrates; and mixtures thereof. In addition to the appropriate carbon source, the fermentation medium may contain a suitable nitrogen source, such as an ammonium salt, yeast extract or peptone, minerals, salts, cofactors, buffers and other components, known to those skilled in the art (Bailey et al., supra). Suitable conditions for the extractive fermentation depend on the particular microorganism used and may be readily determined by one skilled in the art using routine experimentation.

Methods for Recovering Butanol Using Extractive Fermentation with Added Electrolyte Butanol may be recovered from a fermentation medium containing butanol, water, at least one electrolyte at a concentration at least sufficient to increase the butanol partition coefficient relative to that in the presence of the salt concentration of the basal fermentation medium, optionally at least one fermentable carbon source, and a microorganism that has been genetically modified (that is, genetically engineered) to produce butanol via a biosynthetic pathway from at least one carbon source. Such genetically modified microorganisms can be selected from bacteria, cyanobacteria, filamentous fungi and yeasts and include *Escherichia coli, Lactobacillus plantarum*, and *Saccharomyces cerevisiae*, for example. One step in the process is contacting the fermentation medium with a first water-immiscible organic extractant and optionally a second water-immiscible organic extractant to form a two-phase mixture comprising an aqueous phase and a butanol-containing organic phase. "Contacting" means the fermentation medium and the organic extractant or its solvent components are brought into physical contact at any time during the fermentation process. The electrolyte may be added to the fermentation medium, to the first extractant, to the optional second extractant, or to combinations thereof. In one embodiment, the fermentation medium further comprises ethanol, and the butanol-containing organic phase can contain ethanol.

When a first and a second extractant are used, the contacting may be performed with the first and second extractants having been previously combined. For example, the first and second extractants may be combined in a vessel such as a mixing tank, and the combined extractants may then be added to a vessel containing the fermentation medium. Alternatively, the contacting may be performed with the first and second extractants becoming combined during the contacting. For example, the first and second extractants may be added separately to a vessel which contains the fermentation medium. In one embodiment, contacting the fermentation medium with the organic extractant further comprises contacting the fermentation medium with the first extractant prior to contacting the fermentation medium and the first extractant with the second extractant. In one embodiment, the contacting with the second extractant may occur in the same vessel as the contacting with the first extractant. In one embodiment, the contacting with the second extractant may occur in a different vessel from the contacting with the first extractant. For example, the first extractant may be contacted with the fermentation medium in one vessel, and the contents transferred to another vessel in which contacting with the second extractant occurs. In these embodiments, the electrolyte may be added to the fermentation medium, to the first extractant, to the optional second extractant, or to combinations thereof.

The organic extractant may contact the fermentation medium at the start of the fermentation forming a biphasic fermentation medium. Alternatively, the organic extractant may contact the fermentation medium after the microorganism has achieved a desired amount of growth, which can be determined by measuring the optical density of the culture. In one embodiment, the first extractant may contact the fermentation medium in one vessel, and the second extractant may contact the fermentation medium and the first extractant in the same vessel. In another embodiment, the second extractant may contact the fermentation medium and the first extractant in a different vessel from that in which the first extractant contacts the fermentation medium. In these embodiments, the electrolyte may be added to the fermentation medium, to the first extractant, to the optional second extractant, or to combinations thereof.

Further, the organic extractant may contact the fermentation medium at a time at which the butanol level in the fermentation medium reaches a preselected level, for example, before the butanol concentration reaches a toxic or an inhibitory level. The butanol concentration may be monitored during the fermentation using methods known in the art, such as by gas chromatography or high performance liquid chromatography. The electrolyte may be added to the fermentation medium before or after the butanol concentration reaches a toxic or an inhibitory level. In embodiments, the organic extractant comprises fatty acids. In embodiments, processes described herein can be used in conjunction with processes described in U.S. Provisional Patent Application Nos. 61/368,429 and 61/379,546 wherein butanol is esterified with an organic acid such as fatty acid using a catalyst such as a lipase to form butanol esters.

Fermentation may be run under aerobic conditions for a time sufficient for the culture to achieve a preselected level of growth, as determined by optical density measurement. The electrolyte may be added to the fermentation broth before or after the preselected level of growth is achieved. An inducer may then be added to induce the expression of the butanol biosynthetic pathway in the modified microorganism, and fermentation conditions are switched to microaerobic or anaerobic conditions to stimulate butanol production, as described in detail in Example 6 of U.S. patent application Ser. No. 12/478,389. The extractant may be added after the switch to microaerobic or anaerobic conditions. The electrolyte may be added before or after the switch to microaerobic or anaerobic conditions. In one embodiment, the first extractant may contact the fermentation medium prior to the contacting of the fermentation medium and the first extractant with the second extractant. For example, in a batch fermentation process, a suitable period of time may be allowed to elapse between contacting the fermentation medium with the first and the second extractants. In a continuous fermentation process, contacting the fermentation medium with the first extractant may occur in one vessel, and contacting of that vessel's contents with the second extractant may occur in a second vessel. In these embodiments, the electrolyte may be added to the fermentation medium, to the first extractant, to the optional second extractant, or to combinations thereof.

After contacting the fermentation medium with the organic extractant in the presence of the electrolyte, the butanol product partitions into the organic extractant, decreasing the concentration in the aqueous phase containing the microorganism, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, the electrolyte concentration, and the fermentation mode chosen, as described below. The volume of the organic extractant may be about 3% to about 60% of the fermentor working volume. The ratio of the extractant to the fermentation medium is from about 1:20 to about 20:1 on a volume:volume basis, for example from about 1:15 to about 15:1, or from about 1:12 to about 12:1, or from about 1:10 to about 10:1, or from about 1:9 to about 9:1, or from about 1:8 to about 8:1.

The amount of the electrolyte to be added depends on a number of factors, including the effect of the added electrolyte on the growth properties of the butanol producing microorganism and the effect of the added electrolyte on the Kp of butanol in a two phase fermentation. The optimum amount of electrolyte to be added may also be dependent on the composition of the initial basal fermentation medium. Too high a concentration of an electrolyte, although possibly increasing the Kp of butanol and alleviating the toxicity effects of butanol on the microorganism, can itself be inhibitory to the microorganism. On the other hand, too low a concentration of electrolyte might not increase the Kp of butanol sufficiently to alleviate the inhibitory effect of butanol on the microorganism. Therefore, a balance needs to be found through experimentation to ensure that the net effect of adding excess electrolyte to the fermentation medium results in an overall increase in the rate and titer of butanol production. In addition, one could modulate the biocompatibility of the salts to the microorganism by addition of osmoprotectants or osmolytes either exogenously to the medium or by genetically modifying the microorganism to endogenously produce the osmolyte(s). In embodiments, the Kp is increased by about 10%, about 20%, about 30%, about 40%, about 50%, about 60%, about 70%, about 80%, about 90%, about 100%, about 150%, or about 200% as compared to the Kp without added electrolyte. In embodiments, the Kp is increased by at least about 2-fold, at least about 3-fold, at least about 4 fold, at least about 5-fold, or at least about 6-fold. In embodiments, the total concentration of electrolyte is selected to increase the Kp by an amount while maintaining the growth rate of the microorganism at a level that is at least about 25%, at least about 50%, at least about 80%, or at least about 90% of the growth rate in the absence of added electrolyte. In embodiments, the total concentration of electrolyte in the fermentation medium is sufficient to increase the effective rate of butanol production by at least about 10%, at least about 20%, at least about 30%, at least about 40%, at least about 50%, at least about 60%, at least about 70%, at least about 80%, at least about 90%, or at least about 100% as compared to the rate without added electrolyte. In embodiments, the total concentration of electrolyte in the fermentation medium is sufficient to increase the effective yield of butanol by at least about 10%, at least about 20%, at least about 30%, at least about 40%, at least about 50%, at least about 60%, at least about 70%, at least about 80%, at least about 90%, or at least about 100% as compared to the effective yield without added electrolyte. In embodiments, the total concentration of electrolyte in the fermentation medium is sufficient to increase the effective titer of butanol by at least about 10%, at least about 20%, at least about 30%, at least about 40%, at least about 50%, at least about 60%, at least about 70%, at least about 80%, at least about 90%, or at least about 100% as compared to the effective titer without added electrolyte.

In embodiments, the amount of added electrolyte is sufficient to result in an effective titer of at least about 7 g/L, at least about 10 g/L, at least about 15 g/L, at least about 20 g/L, at least about 25 g/L, at least about 30 g/L, or at least about 40 g/L. In embodiments, the amount of added electrolyte is sufficient to result in an effective yield of at least about 0.12, at least about 0.15, at least about 0.2, at least about 0.25, or at least about 0.3. In embodiments, the amount of added electrolyte is sufficient to result in an effective rate of at least about 0.1 g/L/h, at least about 0.15 g/L/h, at least about 0.2 g/L/h, at least about 0.3 g/L/h, at least about 0.4 g/L/h, at least about 0.6 g/L/h, at least about 0.8 g/L/h, at least about 1 g/L/h, or at least about 1.2 g/L/h. In some embodiments, the effective rate is about 1.3 g/L/h.

The next step is optionally separating the butanol-containing organic phase from the aqueous phase using methods known in the art, including but not limited to, siphoning, decantation, centrifugation, using a gravity settler, and membrane-assisted phase splitting.

Recovery of the butanol from the butanol-containing organic phase may be done using methods known in the art, including but not limited to, distillation, adsorption by resins, separation by molecular sieves, and pervaporation. Specifically, distillation may be used to recover the butanol from the butanol-containing organic phase. The extractant may be recycled to the butanol production and/or recovery process.

The electrolyte may be recovered from the fermentation medium or from the aqueous phase of a two phase mixture by methods known in the art. For example, the aqueous phase or fermentation medium may be concentrated by distillation, stripping, pervaporation, or other methods to obtain a concentrated aqueous mixture comprising the electrolyte. Optionally, the electrolyte may be returned to a fermentation medium and thus be recycled within the fermentation process. Optionally, the electrolyte obtained from a fermentation medium may be added to a fermentation medium to provide a concentration at least sufficient to increase the butanol partition coefficient relative to that in the presence of the salt concentration of the basal fermentation medium.

Gas stripping may be used concurrently with the organic extractant and the addition of electrolyte to remove the butanol product from the fermentation medium. Gas stripping may be done by passing a gas such as air, nitrogen, or carbon dioxide through the fermentation medium, thereby forming a butanol-containing gas phase. The butanol product may be recovered from the butanol-containing gas phase using methods known in the art, such as using a chilled water trap to condense the butanol, or scrubbing the gas phase with a solvent.

Any butanol remaining in the fermentation medium after the fermentation run is completed may be recovered by continued extraction using fresh or recycled organic extractant. Alternatively, the butanol can be recovered from the fermentation medium using methods known in the art, such as distillation, azeotropic distillation, liquid-liquid extraction, adsorption, gas stripping, membrane evaporation, pervaporation, and the like. In the case where the fermentation medium is not recycled to the process, additional electrolyte may be added to further increase the butanol partition coefficient and improve the efficiency of butanol recovery.

The two-phase extractive fermentation method may be carried out in a continuous mode in a stirred tank fermentor. In this mode, the mixture of the fermentation medium and the butanol-containing organic extractant is removed from the fermentor. The two phases are separated by means known in the art including, but not limited to, siphoning, decantation, centrifugation, using a gravity settler, membrane-assisted phase splitting, and the like, as described above. After separation, the fermentation medium and the electrolyte therein may be recycled to the fermentor or may be replaced with fresh medium, to which additional electrolyte is added. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant is required enabling a larger volume of the fermentation medium to be used. This results in higher production yields. The volume of the organic extractant may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. The apparatus that may be used to carryout these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, the desired amount of supplemental electrolyte and a volume of organic extractant are added to the fermentor and the extractant is not removed during the process. The organic extractant may be formed in the fermentor by separate addition of the first and the optional second extractants, or the first and second extractants may be combined to form the extractant prior to the addition of any extractant to the fermentor. The electrolyte may be added to the fermentation medium, to the first extractant, to the optional second extractant, or to combinations thereof. Although this fermentation mode is simpler than the continuous or the entirely continuous modes described above, it requires a larger volume of organic extractant to minimize the concentration of the inhibitory butanol product in the fermentation medium. Consequently, the volume of the fermentation medium is less and the amount of product produced is less than that obtained using the continuous mode. The volume of the organic extractant in the batchwise mode may be 20% to about 60% of the fermentor working volume; or 30% to about 60% of the fermentor working volume. It is beneficial to use the smallest volume of extractant in the fermentor as possible, for the reason described above.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic extractant used and its methods of addition in this mode is the same as that used in the batchwise mode, described above. The amount of added electrolyte may be the same as in other fermentation modes.

Extraction of the product may be done downstream of the fermentor, rather than in situ. In this external mode, the extraction of the butanol product into the organic extractant is carried out on the fermentation medium removed from the fermentor. The electrolyte may be added to the fermentation medium removed from the fermentor. The amount of extractant used is about 20% to about 60% of the fermentor working volume; or 30% to about 60% of the fermentor working volume. The fermentation medium may be removed from the fermentor continuously or periodically, and the extraction of the butanol product by the organic extractant may be done with or without the removal of the cells from the fermentation medium. The cells may be removed from the fermentation medium by means known in the art including, but not limited to, filtration or centrifugation. The electrolyte may be added to the fermentation medium before or after removal of the cells. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant may be recycled for use in the extraction process. Alternatively, fresh extractant may be used. In this mode the extractant is not present in the fermentor, so the toxicity of the extractant is much less of a problem. If the cells are separated from the fermentation medium before contacting with the extractant, the problem of extractant toxicity may be further reduced. Furthermore, using this external mode there is less chance of forming an emulsion and evaporation of the extractant is minimized, alleviating environmental concerns.

Methods for Production of Butanol Using Extractive Fermentation with Added Electrolyte An improved method for the production of butanol is provided, wherein a microorganism that has been genetically modified to produce butanol via a biosynthetic pathway from at least one fermentable carbon source is grown in a biphasic fermentation medium comprising an aqueous phase and i) a first water-immiscible organic extractant and optionally ii) a second water-immiscible organic extractant, and the biphasic fermentation medium further comprises at least one electrolyte at a concentration at least sufficient to increase the butanol partition coefficient relative to that in the presence of the salt concentration of the basal fermentation medium. Such genetically modified microorganisms can be selected from bacteria, cyanobacteria, filamentous fungi and yeasts and include *Escherichia coli, Lactobacillus plantarum*, and *Saccharomyces cerevisiae*, for example The first water-immiscible organic extractant may be selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof, and the optional second water-immiscible organic extractant may be selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides, and mixtures thereof, wherein the biphasic fermentation medium comprises from about 10% to about 90% by volume of the organic extractant. Alternatively, the biphasic fermentation medium may comprise from about 3% to about 60% by volume of the organic extractant, or from about 15% to about 50%. The microorganism is grown in the biphasic fermentation medium for a time sufficient to extract butanol into the extractant to form a butanol-containing organic phase. The at least sufficient concentration of the electrolyte in the fermentation medium may be achieved by adding electrolyte to the aqueous phase during the growth phase of the microorganism, to the aqueous phase during the butanol production phase, to the aqueous phase when the butanol concentration in the aqueous phase is inhibitory, to the first extractant, to the second extractant, or to combinations thereof.

In one embodiment, the fermentation medium further comprises ethanol, and the butanol-containing organic phase can contain ethanol. The butanol-containing organic phase is then separated from the aqueous phase, as described above. Subsequently, the butanol is recovered from the butanol-containing organic phase, as described above.

Also provided is an improved method for the production of butanol wherein a microorganism that has been genetically modified to produce butanol via a biosynthetic pathway from at least one carbon source is grown in a fermentation medium wherein the microorganism produces the butanol into the fermentation medium to produce a butanol-containing fermentation medium. Such genetically modified microorganisms can be selected from bacteria, cyanobacteria, filamentous fungi and yeasts and include *Escherichia coli, Lactobacillus plantarum*, and *Saccharomyces cerevisiae*, for example. At least one electrolyte is added to the fermentation medium to provide the electrolyte at a concentration at least sufficient to increase the butanol partition coefficient relative to that in the presence of the salt concentration of the basal fermentation medium. In one embodiment, the electrolyte may be added to the fermentation medium when the microorganism growth phase slows. In one embodiment, the electrolyte may be added to the fermentation medium when the butanol production phase is complete. At least a portion of the butanol-containing fermentation medium is contacted with a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof, and optionally ii) a second water-immiscible organic extractant selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides and mixtures thereof, to form a two-phase mixture comprising an aqueous phase and a butanol-containing organic phase. The butanol-containing organic phase is then separated from the aqueous phase, as described above. Subsequently, the butanol is recovered from the butanol-containing organic phase, as described above. At least a portion of the aqueous phase is returned to the fermentation medium. In one embodiment, the fermentation medium further comprises ethanol, and the butanol-containing organic phase can contain ethanol.

Isobutanol may be produced by extractive fermentation with the use of a modified *Escherichia coli* strain in combination with an oleyl alcohol as the organic extractant, as disclosed in U.S. patent application Ser. No. 12/478,389. The method yields a higher effective titer for isobutanol (i.e., 37 g/L) compared to using conventional fermentation techniques (see Example 6 of U.S. patent application Ser. No. 12/478,389). For example, Atsumi et al. (*Nature* 451(3):86-90, 2008) report isobutanol titers up to 22 g/L using fermentation with an *Escherichia coli* that was genetically modified to contain an isobutanol biosynthetic pathway. The higher butanol titer obtained with the extractive fermentation method disclosed in U.S. patent application Ser. No. 12/478,389 results at least in part from the removal of the toxic butanol product from the fermentation medium, thereby keeping the level below that which is toxic to the microorganism. It is reasonable to assume that the present extractive fermentation method employing the use of at least one electrolyte at a concentration in the fermentation medium at least sufficient to increase the butanol partition coefficient relative to that in the presence of the salt concentration of the basal fermentation medium as defined herein would be used in a similar way and provide similar results.

Butanol produced by the methods disclosed herein may have an effective titer of greater than 22 g per liter of the fermentation medium. Alternatively, the butanol produced by methods disclosed may have an effective titer of at least 25 g per liter of the fermentation medium. Alternatively, the butanol produced by methods described herein may have an effective titer of at least 30 g per liter of the fermentation medium. Alternatively, the butanol produced by methods described herein may have an effective titer of at least 37 g per liter of the fermentation medium.

The present methods are generally described below with reference to FIG. 1 through FIG. 7.

Referring now to FIG. 1, there is shown a schematic representation of one embodiment of processes for producing and recovering butanol using in situ extractive fermentation. An aqueous stream 10 of at least one fermentable carbon source, optionally containing electrolyte, is introduced into a fermentor 20, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 12 and a stream of the optional second extractant 14 are introduced to a vessel 16, in which the first and second extractants are combined to form the combined extractant 18. Optionally, electrolyte may be added (not shown) to stream 18, to vessel 16, to the stream of the first extractant 12, to the stream of the second extractant 14, or to a combination thereof. A stream of the extractant 18 is introduced into the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42. Optionally, at least a portion of the aqueous phase 42 containing electrolyte is returned (not shown) to fermentor 20 or another fermentor (not shown). The point(s) of addition of the electrolyte to the process are selected such that the concentration of electrolyte in the aqueous phase 42 is at least sufficient to increase the butanol partition coefficient relative to that in the presence of the salt concentration of the basal fermentation medium.

Referring now to FIG. 2, there is shown a schematic representation of one embodiment of processes for producing and recovering butanol using in situ extractive fermentation. An aqueous stream 10 of at least one fermentable carbon source, optionally containing electrolyte, is introduced into a fermentor 20, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 12 and a stream of the optional second extractant 14 are introduced separately to the fermentor 20, in which contacting of the fermentation medium with the extractant to form a two-phase mixture comprising an aqueous phase and a butanol-containing organic phase occurs. Optionally, electrolyte may be added (not shown) to stream 12, to stream 14, or to a combination thereof. A stream 26 comprising both the aqueous and organic phases is introduced into a vessel 38, in which separation of the aqueous and organic phases is performed to produce a butanol-containing organic phase 40 and an aqueous phase 42. Optionally, at least a portion of the aqueous phase 42 containing electrolyte is returned (not shown) to fermentor 20 or another fermentor (not shown). The point(s) of addition of the electrolyte to the process are selected such that the concentration of electrolyte in the aqueous phase 42 is at least sufficient to increase the butanol partition coefficient relative to that in the presence of the salt concentration of the basal fermentation medium.

Referring now to FIG. 3, there is shown a schematic representation of one embodiment of processes for producing and recovering butanol using in situ extractive fermentation. An aqueous stream 10 of at least one fermentable carbon source, optionally containing electrolyte, is introduced into a first fermentor 20, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 12 is introduced to the fermentor 20, and a stream 22 comprising a mixture of the first extractant and the contents of fermentor 20 is introduced into a second fermentor 24. A stream of the optional second extractant 14 is introduced into the second fermentor 24, in which contacting of the fermentation medium with the extractant to form a two-phase mixture comprising an aqueous phase and a butanol-containing organic phase occurs. Optionally, electrolyte may be added (not shown) to stream 12, to stream 22, to stream 14, to vessel 24, or to a combination thereof. A stream 26 comprising both the aqueous and organic phases is introduced into a vessel 38, in which separation of the aqueous and organic phases is performed to produce a butanol-containing organic phase 40 and an aqueous phase 42. Optionally, at least a portion of the aqueous phase 42 containing electrolyte is returned (not shown) to fermentor 20 or another fermentor (not shown). The point(s) of addition of the electrolyte to the process are selected such that the concentration of electrolyte in the aqueous phase 42 is at least sufficient to increase the butanol partition coefficient relative to that in the presence of the salt concentration of the basal fermentation medium.

Referring now to FIG. 4, there is shown a schematic representation of one embodiment of processes for producing and recovering butanol in which extraction of the product is performed downstream of the fermentor, rather than in situ. An aqueous stream 110 of at least one fermentable carbon source, optionally containing electrolyte, is introduced into a fermentor 120, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 112 and a stream of the optional second extractant 114 are introduced to a vessel 116, in which the first and second extractants are combined to form the combined extractant 118. At least a portion, shown as stream 122, of the fermentation medium in fermentor 120 is introduced into vessel 124. Optionally, electrolyte may be added (not shown) to stream 112, to stream 114, to vessel 116, to stream 118, to vessel 124, or to a combination thereof. A stream of the extractant 118 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142. At least a portion of the aqueous phase 142 containing electrolyte is returned to fermentor 120, or optionally to another fermentor (not shown). The point(s) of addition of the electrolyte to the process are selected such that the concentration of electrolyte in the aqueous phase 142 is at least sufficient to increase the butanol partition coefficient relative to that in the presence of the salt concentration of the basal fermentation medium.

Referring now to FIG. 5, there is shown a schematic representation of one embodiment of processes for producing and recovering butanol in which extraction of the product is performed downstream of the fermentor, rather than in situ. An aqueous stream 110 of at least one fermentable carbon source, optionally containing electrolyte, is introduced into a fermentor 120, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 112 and a stream of the second extractant 114 are introduced separately to a vessel 124, in which the first and second extractants are combined to form the combined extractant. Optionally, electrolyte may be added (not shown) to stream 112, to stream 114, to stream 122, to vessel 124, or to combinations thereof. At least a portion, shown as stream 122, of the fermentation medium in fermentor 120 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142. At least a portion of the aqueous phase 142 containing electrolyte is returned to fermentor 120, or optionally to another fermentor (not shown). The point(s) of addition of the electrolyte to the process are selected such that the concentration of electrolyte in the aqueous phase 142 is at least sufficient to increase the butanol partition coefficient relative to that in the presence of the salt concentration of the basal fermentation medium.

Referring now to FIG. 6, there is shown a schematic representation of one embodiment of processes for producing and recovering butanol in which extraction of the product is performed downstream of the fermentor, rather than in situ. An aqueous stream 110 of at least one fermentable carbon source, optionally containing electrolyte, is introduced into a fermentor 120, which contains at least one genetically modified microorganism (not shown) that produces butanol from a fermentation medium comprising at least one fermentable carbon source. Optionally, electrolyte may be added as a separate stream (not shown) to the fermentor. A stream of the first extractant 112 is introduced to a vessel 128, and at least a portion, shown as stream 122, of the fermentation medium in fermentor 120 is also introduced into vessel 128. Optionally, electrolyte may be added (not shown) to stream 122, to stream 112, to vessel 128, or to a combination thereof. A stream 130 comprising a mixture of the first extractant and the contents of fermentor 120 is introduced into a second vessel 132. Optionally, electrolyte may be added (not shown) to stream 130, to stream 114, to vessel 132, or to a combination thereof. A stream of the optional second extractant 114 is introduced into the second vessel 132, in which contacting of the fermentation medium with the extractant to form a two-phase mixture comprising an aqueous phase and a butanol-containing organic phase occurs. A stream 134 comprising both the aqueous and organic phases is introduced into a vessel 138, in which separation of the aqueous and organic phases is performed to produce a butanol-containing organic phase 140 and an aqueous phase 142. At least a portion of the aqueous phase 142 containing electrolyte is returned to fermentor 120, or optionally to another fermentor (not shown). The point(s) of addition of the electrolyte to the process are selected such that the concentration of electrolyte in the aqueous phase 142 is at least sufficient to increase the butanol partition coefficient relative to that in the presence of the salt concentration of the basal fermentation medium.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation can increase effective rate, titer and yield.

In yet another embodiment, it is also possible to operate the liquid-liquid extraction in a flexible co-current or, alternatively, counter-current way that accounts for the difference in batch operating profiles when a series of batch fermentors are used. In this scenario the fermentors are filled with fermentable mash which provides at least one fermentable carbon source and microorganism in a continuous fashion one after another for as long as the plant is operating. Referring to FIG. 7, once Fermentor F100 fills with mash and microorganism, the mash and microorganism feeds advance to Fermentor F101 and then to Fermentor F102 and then back to Fermentor F100 in a continuous loop. Electrolyte may be added (not shown) to one or more Fermentors, to the stream entering the Fermentor, to the stream exiting the fermentor, or a combination thereof. The fermentation in any one fermentor begins once mash and microorganism are present together and continues until the fermentation is complete. The mash and microorganism fill time equals the number of fermentors divided by the total cycle time (fill, ferment, empty and clean). If the total cycle time is 60 hours and there are 3 fermentors then the fill time is 20 hours. If the total cycle time is 60 hours and there are 4 fermentors then the fill time is 15 hours.

Adaptive co-current extraction follows the fermentation profile assuming the fermentor operating at the higher broth phase titer can utilize the extracting solvent stream richest in butanol concentration and the fermentor operating at the lowest broth phase titer will benefit from the extracting solvent stream leanest in butanol concentration. For example, referring again to FIG. 7, consider the case where Fermentor F100 is at the start of a fermentation and operating at relatively low butanol broth phase (B) titer, Fermentor F101 is in the middle of a fermentation operating at relatively moderate butanol broth phase titer and Fermentor F102 is near the end of a fermentation operating at relatively high butanol broth phase titer. In this case, lean extracting solvent (S), with minimal or no extracted butanol, can be fed to Fermentor F100, the "solvent out" stream (S') from Fermentor F100 having an extracted butanol component can then be fed to Fermentor F101 as its "solvent in" stream and the solvent out stream from F101 can then be fed to Fermentor F102 as its solvent in stream. The solvent out stream from F102 can then be sent to be processed to recover the butanol present in the stream. The processed solvent stream from which most of the butanol is removed can be returned to the system as lean extracting solvent and would be the solvent in feed to Fermentor F100 above.

As the fermentations proceed in an orderly fashion the valves in the extracting solvent manifold can be repositioned to feed the leanest extracting solvent to the fermentor operating at the lowest butanol broth phase titer. For example, assume (a) Fermentor F102 completes its fermentation and has been reloaded and fermentation begins anew, (b) Fermentor F100 is in the middle of its fermentation operating at moderate butanol broth phase titer and (c) Fermentor F101 is near the end of its fermentation operating at relatively higher butanol broth phase titer. In this scenario the leanest extracting solvent would feed F102, the extracting solvent leaving F102 would feed Fermentor F100 and the extracting solvent leaving Fermentor F100 would feed Fermentor F101.

The advantage of operating this way can be to maintain the broth phase butanol titer as low as possible for as long as possible to realize improvements in productivity. Additionally, it can be possible to drop the temperature in the other fermentors that have progressed further into fermentation that are operating at higher butanol broth phase titers. The drop in temperature can allow for improved tolerance to the higher butanol broth phase titers.

Advantages of the Present Methods

The present extractive fermentation methods provide butanol known to have an energy content similar to that of gasoline and which can be blended with any fossil fuel. Butanol is favored as a fuel or fuel additive as it yields only $CO_2$ and little or no $SO_X$ or $NO_X$ when burned in the standard internal combustion engine. Additionally, butanol is less corrosive than ethanol, the most preferred fuel additive to date.

In addition to its utility as a biofuel or fuel additive, the butanol produced according to the present methods has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles. Furthermore, the present methods produce butanol from plant derived carbon sources, avoiding the negative environmental impact associated with standard petrochemical processes for butanol production.

Advantages of the present methods include the feasibility of producing butanol at net effective rate, titer, and yield that are significantly higher and more economical than the threshold levels of butanol obtained by a two phase extractive fermentation process without the addition of at least one electrolyte at a concentration at least sufficient to increase the butanol partition coefficient relative to that in the presence of the salt concentration of the basal fermentation medium. The present method can also reduce the net amount of fresh or recycled extractant needed to achieve a desired level of butanol production from a batch fermentation.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials

The following materials were used in the examples. All commercial reagents were used as received.

All solvents were obtained from Sigma-Aldrich (St. Louis, Mo.) and were used without further purification. The oleyl alcohol used was technical grade, which contained a mixture of oleyl alcohol (65%) and higher and lower fatty alcohols. Isobutanol (purity 99.5%) was obtained from Sigma-Aldrich and was used without further purification. Sodium sulfate ($Na_2SO_4$, CAS 7757-82-6, greater than 99% purity) was obtained from Sigma-Aldrich (St. Louis, Mo.). Sodium chloride (NaCl, CAS 7647-14-5, Technical grade) was purchased from EMD Chemicals, Inc. (Gibbstown, N.J.).

General Methods

Optical density reading for measuring microorganism cell concentration was done using a Thermo Electron Corporation Helios Alpha spectrophotometer. Measurements were typically done using a wavelength of 600 nanometers.

Glucose concentration in the culture broth was measured rapidly using a 2700 Select Biochemistry Analyzer (YSI Life Sciences, Yellow Springs, Ohio). Culture broth samples were centrifuged at room temperature for 2 minutes at 13,200 rpm in 1.8 mL Eppendorf tubes, and the aqueous supernatant analyzed for glucose concentration. The analyzer performed a self-calibration with a known glucose standard before assaying each set of fermentor samples; an external standard was also assayed periodically to ensure the integrity of the culture broth assays. The analyzer specifications for the analysis were as follows:

Sample size: 15 µL
Black probe chemistry: dextrose
White probe chemistry: dextrose Isobutanol and glucose concentrations in the aqueous phase were measured by HPLC (Waters Alliance Model, Milford, Mass. or Agilent 1200 Series, Santa Clara, Calif.) using a BioRad Aminex HPX-87H column, 7.8 mm×300 mm, (Bio-Rad laboratories, Hercules, Calif.) with appropriate guard columns, using 0.01 N aqueous sulfuric acid, isocratic, as the eluant. The sample was passed through a 0.2 µm centrifuge filter (Nanosep MF modified nylon) into an HPLC vial. The HPLC run conditions were as follows:

Injection volume: 10 µL
Flow rate: 0.60 mL/minute
Run time: 40 minutes
Column Temperature: 40° C.
Detector: refractive index
Detector temperature: 35° C.
UV detection: 210 nm, 8 nm bandwidth After the run, concentrations in the sample were determined from standard curves for each of the compounds. The retention times were 32.6 and 9.1 minutes for isobutanol and glucose, respectively.

Isobutanol and ethanol in the organic extractant phase was measured using Gas Chromatography (GC) as described below.

The following GC method was used to determine the amount of isobutanol and ethanol in the organic phase. The GC method utilized a J&W Scientific DB-WAXETR column (50 m×0.32 mm ID, 1 µm film) from Agilent Technologies (Santa Clara, Calif.). The carrier gas was helium at a flow rate of 4 mL/min with constant head pressure; injector split was 1:5 at 250° C.; oven temperature was 40° C. for 5 min, 40° C. to 230° C. at 10° C./min, and 230° C. for 5 min. Flame ionization detection was used at 250° C. with 40 mL/min helium makeup gas. Culture broth samples were centrifuged before injection. The injection volume was 1.0 µL. Calibrated standard curves were generated for ethanol and isobutanol.

Under these conditions, the isobutanol retention time was 9.9 minutes, and the retention time for ethanol was 8.7 minutes.

Construction of an *E. coli* Strain Having Deletions of pflB, frdB, ldhA, and adhE Genes Provided herein is a suitable method for deleting pflB, frdB, ldhA, and adhE genes from *E. coli*. The Keio collection of *E. coli* strains (Baba et al., Mol. Syst. Biol., 2:1-11, 2006) was used for production of eight of the knockouts. The Keio collection (available from NBRP at the National Institute of Genetics, Japan) is a library of single gene knockouts created in strain *E. coli* BW25113 by the method of Datsenko and Wanner (Datsenko, K. A. & Wanner, B. L., Proc Natl Acad. Sci., USA, 97: 6640-6645, 2000). In the collection, each deleted gene was replaced with a FRT-flanked kanamycin marker that was removable by Flp recombinase. The *E. coli* strain carrying multiple knockouts was constructed by moving the knockout-kanamycin marker from the Keio donor strain by bacteriophage P1 transduction to a recipient strain. After each P1 transduction to produce a knockout, the kanamycin marker was removed by Flp recombinase. This markerless strain acted as the new recipient strain for the next P1 transduction. One of the described knockouts was constructed directly in the strain using the method of Datsenko and Wanner (supra) rather than by P1 transduction.

The 4KO *E. coli* strain was constructed in the Keio strain JW0886 by P1$_{vir}$ transductions with P1 phage lysates prepared from three Keio strains. The Keio strains used are listed below:

JW0886: the kan marker is inserted in the pflB
JW4114: the kan marker is inserted in the frdB
JW1375: the kan marker is inserted in the ldhA
JW1228: the kan marker is inserted in the adhE

[Sequences corresponding to the inactivated genes are: pflB (SEQ ID NO: 71), frdB (SEQ ID NO: 73), ldhA (SEQ ID NO: 77), adhE (SEQ ID NO: 75).]

Removal of the FRT-flanked kanamycin marker from the chromosome was performed by transforming the kanamycin-resistant strain with pCP20 an ampicillin-resistant plasmid (Cherepanov and Wackernagel, supra). Transformants were spread onto LB plates containing 100 µg/mL ampicillin. Plasmid pCP20 carries the yeast FLP recombinase under the control of the $\lambda_{PR}$ promoter and expression from this promoter is controlled by the cI857 temperature-sensitive repressor residing on the plasmid. The origin of replication of pCP20 is also temperature-sensitive.

Removal of the loxP-flanked kanamycin marker from the chromosome was performed by transforming the kanamycin-resistant strain with pJW168 an ampicillin-resistant plasmid (Wild et al., Gene. 223:55-66, 1998) harboring the bacteriophage P1 Cre recombinase. Cre recombinase (Hoess, R. H. & Abremski, K., supra) mediates excision of the kanamycin resistance gene via recombination at the loxP sites. The origin of replication of pJW168 is the temperature-sensitive pSC101. Transformants were spread onto LB plates containing 100 µg/mL ampicillin.

Strain JW0886 (ΔpflB::kan) was transformed with plasmid pCP20 and spread on the LB plates containing 100 µg/mL ampicillin at 30° C. Ampicillin resistant transformants were then selected, streaked on the LB plates and grown at 42° C. Isolated colonies were patched onto the ampicillin and kanamycin selective medium plates and LB plates. Kanamycin-sensitive and ampicillin-sensitive colonies were screened by colony PCR with primers pflB CkUp (SEQ ID NO: 78) and pflB CkDn (SEQ ID NO: 79). A 10 µL aliquot of the PCR reaction mix was analyzed by gel electrophoresis. The expected approximate 0.4 kb PCR product was observed confirming removal of the marker and creating the "JW0886 markerless" strain. This strain has a deletion of the pflB gene.

The "JW0886 markerless" strain was transduced with a P1$_{vir}$ lysate from JW4114 (frdB::kan) and streaked onto the LB plates containing 25 µg/mL kanamycin. The kanamycin-resistant transductants were screened by colony PCR with primers frdB CkUp (SEQ ID NO: 80) and frdB CkDn (SEQ ID NO: 81). Colonies that produced the expected approximate 1.6 kb PCR product were made electrocompetent and transformed with pCP20 for marker removal as described above. Transformants were first spread onto the LB plates containing 100 µg/mL ampicillin at 30° C. and ampicillin resistant transformants were then selected and streaked on LB plates and grown at 42° C. Isolated colonies were patched onto ampicillin and the kanamycin selective medium plates and LB plates. Kanamycin-sensitive, ampicillin-sensitive colonies were screened by PCR with primers frdB CkUp (SEQ ID NO: 80) and frdB CkDn (SEQ ID NO: 81). The expected approximate 0.4 kb PCR product was observed confirming marker removal and creating the double knockout strain, "ΔpflB frdB".

The double knockout strain was transduced with a P1$_{vir}$ lysate from JW1375 (ΔldhA::kan) and spread onto the LB plates containing 25 µg/mL kanamycin. The kanamycin-resistant transductants were screened by colony PCR with primers ldhA CkUp (SEQ ID NO: 82) and ldhA CkDn (SEQ ID NO: 83). Clones producing the expected 1.5 kb PCR product were made electrocompetent and transformed with pCP20 for marker removal as described above. Transformants were spread onto LB plates containing 100 µg/mL ampicillin at 30° C. and ampicillin resistant transformants were streaked on LB plates and grown at 42° C. Isolated colonies were patched onto ampicillin and kanamycin selective medium plates and LB plates. Kanamycin-sensitive, ampicillin-sensitive colonies were screened by PCR with primers ldhA CkUp (SEQ ID NO: 82) and ldhA CkDn (SEQ ID NO: 83) for a 0.3 kb product. Clones that produced the expected approximate 0.3 kb PCR product confirmed marker removal and created the triple knockout strain designated "3KO" (ΔpflB frdB ldhA).

Strain "3 KO" was transduced with a P1$_{vir}$ lysate from JW1228 (ΔadhE::kan) and spread onto the LB plates containing 25 µg/mL kanamycin. The kanamycin-resistant transductants were screened by colony PCR with primers adhE CkUp (SEQ ID NO: 84) and adhE CkDn (SEQ ID NO: 85). Clones that produced the expected 1.6 kb PCR product were named 3KO adhE::kan. Strain 3KO adhE::kan was made electrocompetent and transformed with pCP20 for marker removal. Transformants were spread onto the LB plates containing 100 µg/mL ampicillin at 30° C. Ampicillin resistant transformants were streaked on the LB plates and grown at 42° C. Isolated colonies were patched onto ampicillin and kanamycin selective plates and LB plates. Kanamycin-sensitive, ampicillin-sensitive colonies were screened by PCR with the primers adhE CkUp (SEQ ID NO: 84) and adhE CkDn (SEQ ID NO: 85). Clones that produced the expected approximate 0.4 kb PCR product were named "4KO" (ΔpflB frdB ldhA adhE).

Construction of an *E. Coli* Production Host (Strain NGCI-031) Containing an Isobutanol Biosynthetic Pathway and Deletions of pflB, frdB, ldhA, and adhE Genes A DNA fragment encoding sadB, a butanol dehydrogenase, (DNA SEQ ID NO:9; protein SEQ ID NO: 10) from *Achromobacter xylosoxidans* was amplified from *A. xylosoxidans* genomic DNA using standard conditions. The DNA was prepared using a Gentra Puregene kit (Gentra Systems, Inc., Minneapolis, Minn.; catalog number D-5500A) following the recommended protocol for gram negative organisms. PCR amplification was done using forward and reverse primers N473 and N469 (SEQ ID NOs: 86 and 87), respectively with Phusion High Fidelity DNA Polymerase (New England Biolabs, Beverly, Mass.). The PCR product was TOPO-Blunt cloned into pCR4 BLUNT (Invitrogen) to produce pCR4Blunt::sadB, which was transformed into *E. coli* Mach-1 cells. Plasmid was subsequently isolated from four clones, and the sequence verified.

The sadB coding region was then cloned into the vector pTrc99a (Amann et al., Gene 69: 301-315, 1988). The pCR4Blunt::sadB was digested with EcoRI, releasing the sadB fragment, which was ligated with EcoRI-digested pTrc99a to generate pTrc99a::sadB. This plasmid was transformed into *E. coli* Mach 1 cells and the resulting transformant was named Mach1/pTrc99a::sadB. The activity of the enzyme expressed from the sadB gene in these cells was determined to be 3.5 mmol/min/mg protein in cell-free extracts when analyzed using isobutyraldehyde as the standard.

The sadB gene was then subcloned into pTrc99A::budB-ilvC-ilvD-kivD as described below. The pTrc99A::budB-ilvC-ilvD-kivD is the pTrc-99a expression vector carrying an operon for isobutanol expression (described in Examples 9-14 the of U.S. Patent Application Publication No. 20070092957). The first gene in the pTrc99A::budB-ilvC-ilvD-kivD isobutanol operon is budB encoding acetolactate synthase from *Klebsiella pneumoniae* ATCC 25955, followed by the ilvC gene encoding acetohydroxy acid reductoisomerase from *E. coli*. This is followed by ilvD encoding acetohydroxy acid dehydratase from *E. coli* and lastly the kivD gene encoding the branched-chain keto acid decarboxylase from *L. lactis*.

The sadB coding region was amplified from pTrc99a::sadB using primers N695A (SEQ ID NO: 88) and N696A (SEQ ID NO: 89) with Phusion High Fidelity DNA Polymerase (New England Biolabs, Beverly, Mass.). Amplification was carried out with an initial denaturation at 98 C. for 1 min, followed by 30 cycles of denaturation at 98° C. for 10 sec, annealing at 62° C. for 30 sec, elongation at 72° C. for 20 sec and a final elongation cycle at 72° C. for 5 min, followed by a 4° C. hold. Primer N695A contained an AvrII restriction site for cloning and a RBS upstream of the ATG start codon of the sadB coding region. The N696A primer included an XbaI site for cloning. The 1.1 kb PCR product was digested with AvrII and XbaI (New England Biolabs, Beverly, Mass.) and gel purified using a Qiaquick Gel Extraction Kit (Qiagen Inc., Valencia, Calif.)). The purified fragment was ligated with pTrc99A::budB-ilvC-ilvD-kivD, that had been cut with the same restriction enzymes, using T4 DNA ligase (New England Biolabs, Beverly, Mass.). The ligation mixture was incubated at 16° C. overnight and then transformed into *E. coli* Mach 1™ competent cells (Invitrogen) according to the manufacturer's protocol. Transformants were obtained following growth on the LB agar with 100 µg/ml ampicillin. Plasmid DNA from the transformants was prepared with QIAprep Spin Miniprep Kit (Qiagen Inc., Valencia, Calif.) according to manufacturer's protocols. The resulting plasmid was called pTrc99A::budB-ilvC-ilvD-kivD-sadB.

Electrocompetent cells of the 4KO strains were prepared as described and transformed with pTrc99A::budB-ilvC-ilvD-kivD-sadB ("pBCDDB"). Transformants were streaked onto LB agar plates containing 100 µg/mL ampicillin. The resulting strain carrying plasmid pTrc99A::budB-ilvC-ilvD-kivD-sadB with 4KO (designated strain NGCI-031) was used for fermentation studies in the indicated Examples.

Example 1

Effect of Electrolyte Concentration on the Partition Coefficient ($K_p$)

The purpose of this Example was to evaluate the effect of electrolyte concentrations in the fermentation medium on the partition coefficient ($K_p$) of isobutanol when oleyl alcohol was used as the extractant. The basal fermentation medium (BFM) typically used in *E. coli* fermentations was used as the fermentation medium in this Example. The BFM composition is shown in Table 2.

TABLE 2

| BFM Composition | | |
|---|---|---|
| Components | Concentration (g/L) or as indicated | Concentration (millimoles/L; mM) |
| Potassium phosphate monobasic | 13.3 | 97.73 |
| Ammonium phosphate dibasic | 4.0 | 30.28 |
| Citric acid monohydrate | 1.7 | 8.09 |
| Magnesium sulfate heptahydrate | 2.0 | 8.11 |
| Trace Elements (mL/L) | 10.0 | — |
| Thiamine Hydrochloride (mg/L) | 4.5 | — |
| Yeast Extract | 5.0 | — |
| Sigma Antifoam 204 (mL/L) | 0.20 | — |
| Glucose | 30.0 | — |

The trace elements solution used in the above medium was prepared as follows. Ingredients listed below were added in the order listed and the solution is heated to 50-60° C. until all the components are completely dissolved. Ferric citrate was added slowly after other ingredients were in solution. The solution was filter sterilized using 0.2 micron filters.

| | |
|---|---|
| EDTA (Ethylenediaminetetra acetic acid) | 0.84 g/L |
| Cobalt dichloride hexahydrate (cobalt chloride 6-hydrate) | 0.25 g/L |
| Manganese dichloride tetrahydrate (manganese chloride 4-hydrate) | 1.5 g/L |
| Cupric chloride dihydrate | 0.15 g/L |
| Boric acid ($H_3BO_3$) | 0.30 g/L |
| Sodium molybdate dihydrate | 0.25 g/L |
| Zinc acetate dihydrate | 1.30 g/L |
| Ferric citrate | 10.0 g/L |

The initial level of total salts (sum of potassium phosphate monobasic, ammonium phosphate dibasic, citric acid monohydrate, and magnesium sulfate heptahydrate) in BFM as shown in Table 2 is calculated to be about 144.2 mM. Since an *E. coli* biocatalyst was used in the Examples shown below, betaine hydrochloride (Sigma-Aldrich) at 0.31 g/L (2 mmoles/L) was added to the basal fermentation medium since it is reported in the literature (Cosquer A, et al; 1999; Appl Environ Microbiol 65:3304-3311) to improve the salt tolerance of *E. coli*.

The following experimental procedure was used to generate the data in Tables 3 and 4. In these $K_p$ measurement experiments, a specified amount of electrolyte as sodium sulfate ($Na_2SO_4$) or sodium chloride (NaCl) was added to the basal fermentation medium. To 30 mL of the electrolyte-supplemented BFM, 10 mL of isobutanol rich oleyl alcohol (OA) extractant containing 168 g/L of isobutanol was added and mixed vigorously for about 4-8 hours at 30° C. with shaking at 250 rpm in a table top shaker (Innova 4230, New Brunswick scientific, Edison, N.J.) to reach equilibrium between the two phases. The aqueous and organic phases in each flask were separated by decantation. The aqueous phase was centrifuged (2 minutes on 13,000 rpm with an Eppendorf centrifuge model 5415R) to remove residual extractant phase and the supernatant analyzed for glucose and isobutanol by HPLC. Analysis of isobutanol levels in the aqueous phase after 4 hrs of shaking was similar to that obtained following 8 hrs of mixing suggesting that equilibrium between the two phases was attained within 4 hours. The intent was to show that further mixing beyond 4 hours did not change $K_p$.

Partition coefficients ($K_p$) for the isobutanol distribution between the organic and aqueous phases were calculated from the known amount of isobutanol added to the flask and the isobutanol concentration data measured for the aqueous phase. The concentration of isobutanol in the extractant phase was determined by the mass balance. The partition coefficient was determined as the ratio of the isobutanol concentrations in the organic and the aqueous phases, i.e., $K_p=$ [Isobutanol]$_{Organic\ phase}$/[isobutanol]$_{Aqueous\ phase}$. Each data point corresponding to a specified level of electrolyte as shown in Table 3 and Table 4 was repeated twice and values for $K_p$ reported as the average of the two flasks.

TABLE 3

Effect of Sodium Sulfate (Na$_2$SO$_4$) Concentration on $K_p$ of isobutanol

| Total initial concentration of salts in BFM (Table 2) moles/L (a) | Amount of sodium sulfate added to BFM Na$_2$SO$_4$ (moles/L) (b) | Total amount of salts in experiment moles/L (a) + (b) | $K_p$ |
|---|---|---|---|
| 0.14 | 0.00 | 0.14 | 4.80 |
| 0.14 | 0.03 | 0.17 | 5.03 |
| 0.14 | 0.07 | 0.21 | 5.25 |
| 0.14 | 0.15 | 0.29 | 5.78 |
| 0.14 | 0.22 | 0.36 | 6.37 |
| 0.14 | 0.29 | 0.43 | 7.12 |
| 0.14 | 0.44 | 0.58 | 8.34 |
| 0.14 | 0.67 | 0.81 | 10.50 |
| 0.14 | 1.00 | 1.14 | 15.95 |
| 0.14 | 1.33 | 1.47 | 24.68 |
| 0.14 | 2.00 | 2.14 | 60.99 |

TABLE 4

Effect of Sodium Chloride (NaCl) Concentration on $K_p$ of isobutanol

| Total initial concentration of salts in BFM (Table 2) moles/L (a) | Amount of sodium chloride added to BFM NaCl (moles/L) (b) | Total amount of salt in experiment moles/L (a) + (b) | $K_p$ |
|---|---|---|---|
| 0.14 | 0.00 | 0.14 | 4.87 |
| 0.14 | 0.01 | 0.15 | 4.87 |
| 0.14 | 0.04 | 0.18 | 4.89 |
| 0.14 | 0.07 | 0.21 | 4.95 |
| 0.14 | 0.11 | 0.25 | 5.00 |
| 0.14 | 0.14 | 0.28 | 5.00 |
| 0.14 | 0.21 | 0.35 | 5.22 |
| 0.14 | 0.33 | 0.47 | 5.04 |
| 0.14 | 0.67 | 0.81 | 5.91 |
| 0.14 | 1.00 | 1.14 | 6.88 |
| 0.14 | 1.33 | 1.47 | 8.06 |

Results from Table 3 and 4 demonstrate that supplementation of the aqueous fermentation medium with the electrolytes Na$_2$SO$_4$ and NaCl resulted in higher $K_p$ for isobutanol in a two phase system with oleyl alcohol as the extractant phase.

Example 2

Effect of Electrolyte Supplementation on Growth Rate of E. Coli

To evaluate the effect of electrolytes such as Na$_2$SO$_4$ on growth properties of the biocatalyst, 4KO E. coli strain, was grown in shake flasks in BFM medium supplemented with 0.31 g/l of betaine hydrochloride and different levels of Na$_2$SO$_4$ (0-284 g/L) at 30° C., 250 RPM in Innova table top shakers. From a frozen vial, 25 mL of seed culture was grown in Difco LB broth, Miller medium, purchased from BD Laboratories (Becton & Dickinson and Company, Sparks, Md., 21152, USA) at 30° C., 200 RPM. 1 mL of this seed culture was added to shake flasks containing 30 mL of BFM medium supplemented with 0.31 g/L of betaine hydrochloride and varying levels of Na$_2$SO$_4$. Samples were withdrawn at defined time points to monitor biomass growth as measured by OD$_{600}$. Growth rates were calculated from the biomass time profiles by fitting exponential growth rate equations.

TABLE 5

Effect of Na$_2$SO$_4$ on growth rate of 4KO E. coli strain

| Total initial concentration of salts in BFM (Table 2) moles/L (a) | Concentration of Na$_2$SO$_4$ (mole/L) added to BFM (b) | Total amount of salts in experiment moles/L (a) + (b) | E. coli Growth Rate (μ) hr$^{-1}$ |
|---|---|---|---|
| 0.14 | 0.00 | 0.14 | 0.79 |
| 0.14 | 0.03 | 0.17 | 0.79 |
| 0.14 | 0.07 | 0.21 | 0.79 |
| 0.14 | 0.15 | 0.29 | 0.79 |
| 0.14 | 0.22 | 0.36 | 0.74 |
| 0.14 | 0.29 | 0.43 | 0.69 |
| 0.14 | 0.44 | 0.58 | 0.60 |
| 0.14 | 0.67 | 0.81 | 0.55 |
| 0.14 | 1.00 | 1.14 | 0.14 |
| 0.14 | 1.33 | 1.47 | Negligible growth |
| 0.14 | 2.00 | 2.14 | Negligible Growth |

The growth rate data shown in Table 5 suggest that the biocatalyst can tolerate salt levels as high as about 0.67 M Na$_2$SO$_4$ (total salt level of 0.81 M) with a 30% loss of growth rate compared to no electrolyte control. However, there is a significant drop (greater than about 80%) in growth rate at 1M salt concentration. Data in Table 3 shows that at 0.67 M concentration of Na$_2$SO$_4$, $K_p$ for butanol increases by twofold compared to no salt addition control when oleyl-alcohol is present as the extractant phase. Thus the net overall effect of electrolyte addition to a 2-phase extractive fermentation using a recombinant butanol producing microorganism can be unpredictable since electrolytes on one hand can inhibit cell growth (Table 3) but on the other can increase the partitioning coefficient of toxic butanol product which could alleviate its toxic effects on the microorganism.

Example 3

Effect of Electrolyte Addition on Rate, Titer, and Yield of Butanol Production in a Two Phase Extractive Fermentation Process The purpose of this example was to demonstrate the advantages of the addition of at least a sufficient amount of electrolyte to the aqueous phase of a two-phase extractive fermentation in which butanol is produced by a recombinant microorganism, a strain of Escherichia coli (NGCI-031) that contains an isobutanol biosynthetic pathway. The extractive fermentation uses oleyl alcohol as the water-immiscible, organic extractant.

The Escherichia coli strain NGCI-031 was constructed as described in the General Methods Section herein above. All seed cultures for inoculum preparation were grown in Luria-Bertani (LB) medium with ampicillin (100 mg/L) as the selection antibiotic. The fermentation medium used was a semi-synthetic medium supplemented with 2 mmoles/L of betaine hydrochloride, the composition of which is given in Table 6.

TABLE 6

Fermentation Medium Composition

| Ingredient | Amount/L | Amount (mmoles/L) |
|---|---|---|
| Phosphoric Acid 85% | 0.75 mL | 14.4 |
| Sulfuric Acid (18M) | 0.30 mL | 5.60 |
| Balch's w/Cobalt - 1000X (composition given in Table 7) | 1.00 mL | NA |
| Potassium Phosphate Monobasic | 1.40 g | 10.30 |
| Citric Acid Monohydrate | 2 g | 9.50 |
| Magnesium Sulfate, heptahydrate | 2 g | 8.10 |
| Ferric Ammonium Citrate | 0.33 g | 1.25 |
| Calcium chloride, dihydrate | 0.20 g | 1.36 |
| Yeast Extract[a] | 5.00 g | |
| Antifoam 204[b] | 0.20 mL | |
| Betaine Hydrochloride | 0.32 g | |
| Thiamince•HCl, 5 g/L stock | 1.00 mL | |
| Ampicillin, 25 mg/mL stock | 4.00 mL | |
| Glucose 50 wt % stock | 33.3 mL | |

[a]Obtained from BD Diagnostic Systems, Sparks, MD
[b]Obtained from Sigma-Aldrich

TABLE 7

Balch's Modified Trace Metals - 1000X

| Ingredient | Concentration (g/L) |
|---|---|
| Citric Acid Monohydrate | 40.0 |
| $MnSO_4 \cdot H_2O$ | 30.0 |
| NaCl | 10.0 |
| $FeSO_4 \cdot 7H_2O$ | 1.0 |
| $CoCl_2 \cdot 6H_2O$ | 1.0 |
| $ZnSO_4 \cdot 7H_2O$ | 1.5 |
| $CuSO_4 \cdot 5H_2O$ | 0.1 |
| Boric Acid ($H_3BO_3$) | 0.1 |
| Sodium Molybnate ($NaMoO_4 \cdot 2H_2O$) | 0.1 |

Ingredients 1-11 from Table 6 were added to water at the prescribed concentration to make a final volume of 0.4 L in the fermentor. The contents of the fermentor were sterilized by autoclaving. Components 12-14 were mixed, filter sterilized and added to the fermentor after the autoclaved medium had cooled. The total final volume of the fermentation medium (the aqueous phase) was about 0.5 L following addition of 50 ml of seed inoculum.

Electrolyte in the form of $Na_2SO_4$ was added at 0 g/L, 40 g/L or 60 g/L concentrations to the medium before sterilization. Filter sterilized solutions of ampicillin, thiamine hydrochloride, and glucose were added to the fermentor medium, post sterilization, to a final concentration of 100 mg/L, 5 mg/L and 20 g/L respectively. Fermentations were run using a 1 L autoclavable bioreactor, Bio Console ADI 1025 (Applikon, Inc, Holland) with a working volume of 900 mL. The temperature was maintained at 30° C. during the entire fermentation and the pH was maintained at 6.8 using ammonium hydroxide. Following inoculation of the sterile fermentation medium with seed culture (2-10 vol %), the fermentor was operated aerobically at a 30% dissolved oxygen (DO) set point with 0.3 vvm of air flow by automatic control of the agitation rate (rpm). Once the desired optical density ($OD_{600}$) was reached (i.e., $OD_{600}=10$), the culture was induced with the addition of 0.4-0.5 mM isopropyl beta-D-1 thiogalactopyranoside to overexpress the isobutanol biosynthetic pathway. Four hours post induction, fermentation conditions were switched to microaerobic conditions by decreasing the airflow to 0.13 slpm and setting the DO set point to 3-5%. The shift to microaerobic conditions initiated isobutanol production while minimizing the amount of carbon going to biomass production, thereby uncoupling biomass formation from isobutanol production. Oleyl alcohol (about 250 mL) was added during the isobutanol production phase to alleviate the problem of inhibition due to build up of isobutanol in the aqueous phase. Glucose was added as a bolus (50 wt % stock solution) to the fermentor on a need basis to keep levels of glucose between 20 g/L and 2 g/L.

Because efficient production of isobutanol requires microaerobic conditions to enable redox balance in the biosynthetic pathway, air was continuously supplied to the fermentor at 0.3 vvm. Continuous aeration led to significant stripping of isobutanol from the aqueous phase of the fermentor. To quantify the loss of isobutanol due to stripping, the off-gas from the fermentor was directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 were monitored continuously to quantify the amount of isobutanol in the gas stream.

For isobutanol production, the effective titer, the effective rate, and the effective yield, all corrected for the isobutanol lost due to stripping, are shown below in tabular form (Table 8). Isobutanol in the aqueous phase was measured using the HPLC method described above herein. Isobutanol in the oleyl-alcohol extractant phase was measured using the GC method described above herein. Glucose levels were monitored using HPLC and YSI as described above herein.

As can be seen from the results in Table 8, the use of electrolytes in an extractive fermentation for isobutanol production results in significantly higher effective titer, effective rate, and effective yield compared to the case where no salt is added. The isobutanol product, which is toxic to the bacterial host, is continuously extracted into the oleyl alcohol phase, decreasing its concentration in the aqueous phase, thereby reducing its toxicity to the microorganism. Additionally, unexpected improvement in the effective rate, effective titer, and effective yield is observed when salt is added to the medium. Addition of salts in principle could not only have a deleterious effect on the metabolism of the butanol producing biocatalyst but also alleviate the inhibitory effect of butanol by increasing Kp of butanol compared to no salt addition control. The net effect of addition of salts in our 2-phase extractive system favors increased production and recovery of butanol.

TABLE 8

Effect of Salts on Rate, Titer, and Yield of Butanol Production in Example 3.

| $Na_2SO_4$ concentration added to fermentation medium in Table 6 (moles/L) | Total amount of salts in experiment (Table 6 + $Na_2SO_4$) moles/L | Effective Rate (g/L/hr) | Effective Titer (g/L) | Effective Yield (g/g) | Kp [Conc in OA phase]/[Conc in Aq Phase] |
|---|---|---|---|---|---|
| 0 | 0.05 | 0.09 | 6 | 0.06 | 3.1 |
| 0.28 | 0.33 | 0.14 | 9 | 0.10 | 4.5 |
| 0.42 | 0.47 | 0.14 | 9.4 | 0.12 | 5.4 |

Initial amount of salts in fermentation medium (Table 6) was about 0.05 moles/L.

Example 4

Effect of Electrolyte Addition on Rate, Titer, and Yield of Butanol Production Coupled with Gas Stripping of Butanol During Fermentation In order to evaluate the effect of electrolyte addition on butanol production during aqueous phase fermentation without the addition of oleyl alcohol extractant, Example 3 was repeated, except that oleyl-alcohol was not added to any of the fermentors. In this Example, gas stripping of butanol from the aqueous phase was prevalent due to air sparging of the fermentors. The amount of butanol stripped to the off-gas was quantified as in Example 3 by using a mass-spec. Effective rate, titer, and yield, all corrected for butanol lost due to stripping are shown below in Table 9.

TABLE 9

Effect of salts on rate, titer, and yield of butanol production coupled with gas stripping of butanol during fermentation for Example 4

| $Na_2SO_4$ concentration added to fermentation medium in Table 6 (moles/L) | Total amount of salts in experiment (Table 6 + $Na_2SO_4$) moles/L | Effective Rate (g/l/hr) | Effective Titer (g/L) | Effective Yield (g/g) | "grams" of isobutanol lost due to stripping |
|---|---|---|---|---|---|
| 0 | 0.05 | 0.08 | 6.0 | 0.11 | 2.55 |
| 0.28 | 0.33 | 0.16 | 10.6 | 0.17 | 4.25 |
| 0.42 | 0.47 | 0.17 | 10.9 | 0.14 | 5.01 |

[Initial amount of salts in fermentation medium (Table 9) was about 0.05 moles/L]

Results from Table 9 show that addition of electrolyte to the aqueous phase increases rate, titer and yield of butanol production in the absence of oleyl alcohol by increasing the stripping rate of isobutanol. Grams of butanol stripped are almost two fold higher in the presence of salt compared to the case with no addition of electrolyte.

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specification, as indicating the scope of the invention.

What is claimed is:

1. A method for the production of butanol comprising:
   a) providing a genetically modified microorganism that produces butanol from at least one fermentable carbon source;
   b) growing the microorganism in a biphasic fermentation medium comprising an aqueous phase and i) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally ii) a second water-immiscible organic extractant selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides, and mixtures thereof, wherein the biphasic fermentation medium further comprises at least one electrolyte at a concentration at least sufficient to increase the butanol partition coefficient relative to that in the presence of the salt concentration of the basal fermentation medium, for a time sufficient to allow extraction of the butanol into the organic extractant to form a butanol-containing organic phase;
   c) separating the butanol-containing organic phase from the aqueous phase; and
   d) optionally, recovering the butanol from the butanol-containing organic phase to produce recovered butanol.

2. The method of claim 1, wherein the electrolyte is added to the aqueous phase during the growth phase of the microorganism, to the aqueous phase during the butanol production phase, to the aqueous phase when the butanol concentration in the aqueous phase is inhibitory, to the first extractant, to the optional second extractant, or to combinations thereof.

3. The method of claim 1, wherein the electrolyte is obtained from a fermentation medium.

4. A method for the production of butanol comprising:
   a) providing a genetically modified microorganism that produces butanol from at least one fermentable carbon source;
   b) growing the microorganism in a fermentation medium wherein the microorganism produces the butanol into the fermentation medium to produce a butanol-containing fermentation medium;
   c) adding at least one electrolyte to the fermentation medium to provide the electrolyte at a concentration at least sufficient to increase the butanol partition coefficient relative to that in the presence of the salt concentration of the basal fermentation medium;
   d) contacting at least a portion of the butanol-containing fermentation medium with i) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof, and optionally ii) a second water-immiscible organic extractant selected from the group consisting of $C_7$ to $C_{22}$ alcohols, $C_7$ to $C_{22}$ carboxylic acids, esters of $C_7$ to $C_{22}$ carboxylic acids, $C_7$ to $C_{22}$ aldehydes, $C_7$ to $C_{22}$ fatty amides, and mixtures thereof, to form a two-phase mixture comprising an aqueous phase and a butanol-containing organic phase;
   e) optionally, recovering the butanol from the butanol-containing organic phase; and
   f) optionally, returning at least a portion of the aqueous phase to the fermentation medium.

5. The method of claim 4, wherein the electrolyte is added to the fermentation medium in step (c) when the microorganism growth phase slows.

6. The method of claim 4, wherein the electrolyte is added to the fermentation medium in step (c) when the butanol production phase is complete.

7. The method of claim 1, wherein said at least one fermentable carbon source is present in the fermentation medium and comprises renewable carbon from agricultural feedstocks, algae, cellulose, hemicellulose, lignocellulose, or any combination thereof.

8. A composition comprising
   (a) a fermentation medium comprising butanol, water, at least one electrolyte at a concentration at least sufficient to increase the butanol partition coefficient ion medium, and a genetically modified microorganism that produces butanol from least one fermentable carbon source;
   b) a first water-immiscible organic extractant selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides and mixtures thereof; and
   c) optionally a second water-immiscible organic extractant selected from the group consisting of $C_7$ to $C_{22}$ fatty alcohols, $C_7$ to $C_{22}$ fatty acids, esters of $C_7$ to $C_{22}$ fatty acids, $C_7$ to $C_{22}$ fatty aldehydes, $C_7$ to $C_{22}$ fatty amides and mixtures thereof;
   wherein said composition forms a two-phase mixture comprising an aqueous phase and a butanol-containing organic phase whereby butanol may be separated from the fermentation medium of (a).

9. The method of claim 1, wherein the electrolyte comprises a salt having a cation selected from the group consisting of lithium, sodium, potassium, rubidium, cesium, magnesium, calcium, strontium, barium, ammonium, phosphonium, and combinations thereof.

10. The method of claim 1, wherein the electrolyte comprises a salt having an anion selected from the group consisting of sulfate, carbonate, acetate, citrate, lactate, phosphate, fluoride, chloride, bromide, iodide, and combinations thereof.

11. The method of claim 1, wherein the electrolyte is selected from the group consisting of sodium sulfate, sodium chloride, and combinations thereof.

12. The method of claim 1, wherein the first extractant is selected from the group consisting of oleyl alcohol, behenyl alcohol, cetyl alcohol, lauryl alcohol, myristyl alcohol, stearyl alcohol, oleic acid, lauric acid, myristic acid, stearic acid, methyl myristate, methyl oleate, lauric aldehyde, 1-dodecanol, and mixtures thereof.

13. The method of claim 1, wherein the butanol is 1-butanol, 2-butanol, isobutanol, or mixtures thereof.

14. The method of claim 1, wherein the fermentation medium further comprises ethanol, and the butanol-containing organic phase contains ethanol.

15. The method of claim 1, wherein the genetically modified microorganism comprises a modification which inactivates a competing pathway for carbon flow.

16. The method of claim 1, wherein the genetically modified microorganism does not produce acetone.

17. The method of claim 1, wherein a portion of the butanol is concurrently removed from the fermentation medium by a process comprising the steps of:
 a) stripping butanol from the fermentation medium with a gas to form a butanol-containing gas phase; and
 b) recovering butanol from the butanol-containing gas phase.

18. The method of claim 1, wherein the genetically modified microorganism is selected from the group consisting of bacteria, cyanobacteria, filamentous fungi, and yeast.

19. The method of claim 18, wherein the microorganism is selected from the group consisting of *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula, Kluyveromyces, Issatchenkia,* and *Saccharomyces*.

* * * * *

SEQUENCE LISTING

```
<160> NUMBER OF SEQ ID NOS: 95

<210> SEQ ID NO 1
<211> LENGTH: 1680
<212> TYPE: DNA
<213> ORGANISM: Klebsiella pneumoniae

<400> SEQUENCE: 1
atggacaaac agtatccggt acgccagtgg gcgcacggcg ccgatctcgt cgtcagtcag      60
ctggaagctc agggagtacg ccaggtgttc ggcatccccg gcgccaaaat cgacaaggtc     120
tttgattcac tgctggattc ctccattcgc attattccgg tacgccacga agccaacgcc     180
gcatttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata aagcgaagca ggtccaccag     360
agtatggata cggtggcgat gttcagcccg gtcaccaaat acgccatcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gcccggtcag cggcaaagtg     540
ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct gcgccgtttg ctggagacca gccatattcc agtcaccagc     720
acctatcagg ccgccggagc ggtgaatcag gataacttct ctcgcttcgc cggccgggtt     780
```

```
gggctgttta acaaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctcaa ccagtttgcc ctgcatcccc tgcgcatcgt tcgcgccatg   1140
caggatatcg tcaacagcga cgtcacgttg accgtggaca tgggcagctt ccatatctgg   1200
attgcccgct acctgtacac gttccgcgcc cgtcaggtga tgatctccaa cggccagcag   1260
accatgggcg tcgccctgcc ctgggctatc ggcgcctggc tggtcaatcc tgagcgcaaa   1320
gtggtctccg tctccggcga cggcggcttc ctgcagtcga gcatggagct ggagaccgcc   1380
gtccgcctga agccaacgt gctgcatctt atctgggtcg ataacggcta acacatggtc   1440
gctatccagg aagagaaaaa atatcagcgc ctgtccggcg tcgagtttgg gccgatggat   1500
tttaaagcct atgccgaatc cttcggcgcg aaagggtttg ccgtggaaag cgccgaggcg   1560
ctggagccga ccctgcgcgc ggcgatggac gtcgacggcc cggcggtagt ggccatcccg   1620
gtggattatc gcgataaccc gctgctgatg ggccagctgc atctgagtca gattctgtaa   1680
```

<210> SEQ ID NO 2
<211> LENGTH: 559
<212> TYPE: PRT
<213> ORGANISM: Klebsiella pneumoniae

<400> SEQUENCE: 2

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
                100                 105                 110

Asp Lys Ala Lys Gln Val His Gln Ser Met Asp Thr Val Ala Met Phe
            115                 120                 125

Ser Pro Val Thr Lys Tyr Ala Ile Glu Val Thr Ala Pro Asp Ala Leu
        130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
                180                 185                 190

Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
```

```
                210               215                 220
Lys Ala Leu Arg Arg Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
            275                 280                 285

Glu Pro Ala Met Trp Asn Ser Gly Asn Ala Thr Leu Val His Ile Asp
        290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
            435                 440                 445

Gly Phe Leu Gln Ser Ser Met Glu Leu Glu Thr Ala Val Arg Leu Lys
        450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
            515                 520                 525

Met Asp Val Asp Gly Pro Ala Val Val Ala Ile Pro Val Asp Tyr Arg
        530                 535                 540

Asp Asn Pro Leu Leu Met Gly Gln Leu His Leu Ser Gln Ile Leu
545                 550                 555

<210> SEQ ID NO 3
<211> LENGTH: 1476
<212> TYPE: DNA
<213> ORGANISM: Escherichia coli

<400> SEQUENCE: 3
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
```

```
ctcgatatct cctacgctct gcgtaaagaa gcgattgccg agaagcgcgc gtcctggcgt      240
aaagcgaccg aaaatggttt taaagtgggt acttacgaag aactgatccc acaggcggat      300
ctggtgatta acctgacgcc ggacaagcag cactctgatg tagtgcgcac cgtacagcca      360
ctgatgaaag acggcgcggc gctgggctac tcgcacggtt tcaacatcgt cgaagtgggc      420
gagcagatcc gtaaagatat caccgtagtg atggttgcgc cgaaatgccc aggcaccgaa      480
gtgcgtgaag agtacaaacg tgggttcggc gtaccgacgc tgattgccgt tcacccggaa      540
aacgatccga aaggcgaagg catggcgatt gccaaagcct gggcggctgc aaccggtggt      600
caccgtgcgg gtgtgctgga atcgtccttc gttgcggaag tgaaatctga cctgatgggc      660
gagcaaacca tcctgtgcgg tatgttgcag gctggctctc tgctgtgctt cgacaagctg      720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag agatcatggc acccctgttc      900
cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccggaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476
```

```
<210> SEQ ID NO 4
<211> LENGTH: 491
<212> TYPE: PRT
<213> ORGANISM: Escherichia coli

<400> SEQUENCE: 4
```

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140
```

| Lys | Asp | Ile | Thr | Val | Val | Met | Val | Ala | Pro | Lys | Cys | Pro | Gly | Thr | Glu |
| --- | --- | --- | --- | --- | --- | --- | --- | --- | --- | --- | --- | --- | --- | --- | --- |
| 145 | | | | 150 | | | | 155 | | | | | 160 | | |

Val Arg Glu Glu Tyr Lys Arg Gly Phe Gly Val Pro Thr Leu Ile Ala
                  165                    170                    175

Val His Pro Glu Asn Asp Pro Lys Gly Glu Gly Met Ala Ile Ala Lys
              180                      185                    190

Ala Trp Ala Ala Ala Thr Gly Gly His Arg Ala Gly Val Leu Glu Ser
    195                        200                    205

Ser Phe Val Ala Glu Val Lys Ser Asp Leu Met Gly Glu Gln Thr Ile
    210                        215                    220

Leu Cys Gly Met Leu Gln Ala Gly Ser Leu Leu Cys Phe Asp Lys Leu
225                230                    235              240

Val Glu Glu Gly Thr Asp Pro Ala Tyr Ala Glu Lys Leu Ile Gln Phe
              245                      250                    255

Gly Trp Glu Thr Ile Thr Glu Ala Leu Lys Gln Gly Gly Ile Thr Leu
              260                      265                    270

Met Met Asp Arg Leu Ser Asn Pro Ala Lys Leu Arg Ala Tyr Ala Leu
        275                    280                    285

Ser Glu Gln Leu Lys Glu Ile Met Ala Pro Leu Phe Gln Lys His Met
    290                      295                    300

Asp Asp Ile Ile Ser Gly Glu Phe Ser Ser Gly Met Met Ala Asp Trp
305                310                    315              320

Ala Asn Asp Asp Lys Lys Leu Leu Thr Trp Arg Glu Thr Gly Lys
              325                      330                    335

Thr Ala Phe Glu Thr Ala Pro Gln Tyr Glu Gly Lys Ile Gly Glu Gln
            340                      345                    350

Glu Tyr Phe Asp Lys Gly Val Leu Met Ile Ala Met Val Lys Ala Gly
        355                    360                    365

Val Glu Leu Ala Phe Glu Thr Met Val Asp Ser Gly Ile Ile Glu Glu
    370                      375                    380

Ser Ala Tyr Tyr Glu Ser Leu His Glu Leu Pro Leu Ile Ala Asn Thr
385                390                    395              400

Ile Ala Arg Lys Arg Leu Tyr Glu Met Asn Val Val Ile Ser Asp Thr
              405                      410                    415

Ala Glu Tyr Gly Asn Tyr Leu Phe Ser Tyr Ala Cys Val Pro Leu Leu
            420                      425                    430

Lys Pro Phe Met Ala Glu Leu Gln Pro Gly Asp Leu Gly Lys Ala Ile
        435                    440                  445

Pro Glu Gly Ala Val Asp Asn Gly Gln Leu Arg Asp Val Asn Glu Ala
    450                      455                    460

Ile Arg Ser His Ala Ile Glu Gln Val Gly Lys Lys Leu Arg Gly Tyr
465                470                    475              480

Met Thr Asp Met Lys Arg Ile Ala Val Ala Gly
            485                      490

<210> SEQ ID NO 5
<211> LENGTH: 1851
<212> TYPE: DNA
<213> ORGANISM: Escherichia coli

<400> SEQUENCE: 5
atgcctaagt accgttccgc caccaccact catggtcgta atatggcggg tgctcgtgcg    60
ctgtggcgcg ccaccggaat gaccgacgcc gatttcggta agccgattat cgcggttgtg  120
aactcgttca cccaatttgt accgggtcac gtccatctgc gcgatctcgg taaactggtc  180

-continued

```
gccgaacaaa ttgaagcggc tggcggcgtt gccaaagagt tcaacaccat tgcggtggat      240
gatgggattg ccatgggcca cgggggggatg ctttattcac tgccatctcg cgaactgatc     300
gctgattccg ttgagtatat ggtcaacgcc cactgcgccg acgccatggt ctgcatctct     360
aactgcgaca aaatcacccc ggggatgctg atggcttccc tgcgcctgaa tattccggtg     420
atctttgttt ccggcggccc gatggaggcc gggaaaacca actttccga tcagatcatc      480 aagctcgatc tggttgatgc gatgatccag ggcgcagacc cgaaagtatc tgactcccag     540
agcgatcagg ttgaacgttc cgcgtgtccg acctgcggtt cctgctccgg atgtttacc     600 gctaactcaa tgaactgcct gaccgaagcg ctgggcctgt cgcagccggg caacggctcg     660
ctgctggcaa cccacgccga ccgtaagcag ctgttcctta atgctggtaa acgcattgtt     720
gaattgacca aacgttatta cgagcaaaac gacgaaagtg cactgccgcg taatatcgcc     780
agtaaggcgg cgtttgaaaa cgccatgacg ctggatatcg cgatgggtgg atcgactaac     840
accgtacttc acctgctggc ggcggcgcag gaagcggaaa tcgacttcac catgagtgat     900
atcgataagc tttcccgcaa ggttccacag ctgtgtaaag ttgcgccgag cacccagaaa     960
taccatatgg aagatgttca ccgtgctggt ggtgttatcg gtattctcgg cgaactggat    1020 cgcgcgggt tactgaaccg tgatgtgaaa acgtacttg gcctgacgtt gccgcaaacg      1080
ctggaacaat acgacgttat gctgacccag gatgacgcgg taaaaatat gttccgcgca     1140 ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgg tgctctacgg taactttgcg gaaaacggct gcatcgtgaa aacggcaggc    1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc    1560 tctggtcttt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactgcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tgggggggtta a            1851
```

<210> SEQ ID NO 6
<211> LENGTH: 616
<212> TYPE: PRT
<213> ORGANISM: Escherichia coli

<400> SEQUENCE: 6

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
                20                  25                  30

Gly Lys Pro Ile Ile Ala Val Val Asn Ser Phe Thr Gln Phe Val Pro
            35                  40                  45

Gly His Val His Leu Arg Asp Leu Gly Lys Leu Val Ala Glu Gln Ile
        50                  55                  60

Glu Ala Ala Gly Gly Val Ala Lys Glu Phe Asn Thr Ile Ala Val Asp
65                  70                  75                  80

-continued

```
Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495
```

```
Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615
```

<210> SEQ ID NO 7
<211> LENGTH: 1647
<212> TYPE: DNA
<213> ORGANISM: Lactococcus lactis

<400> SEQUENCE: 7

```
atgtatactg tggggattta cctgctggat cgcctgcacg aactggggat tgaagaaatt      60
ttcggtgtgc aggcgattta taacctgcag ttcctggacc agattatctc gcacaaagat     120
atgaagtggg tcggtaacgc caacgaactg aacgcgagct atatggcaga tggttatgcc     180
cgtaccaaaa aagctgctgc gtttctgacg acctttggcg ttggcgaact gagcgccgtc     240
aacggactgg caggaagcta cgccgagaac ctgccagttg tcgaaattgt tgggtcgcct     300
acttctaagg ttcagaatga aggcaaattt gtgcaccata ctctggctga tgggattttt     360
aaacatttta tgaaaatgca tgaaccggtt actgcgcccc gcacgctgct gacagcagag     420
aatgctacgg ttgagatcga ccgcgtcctg tctgcgctgc tgaaagagcg caagccggta     480
tatatcaatc tgcctgtcga tgttgccgca gcgaaagccg aaaagccgtc gctgccactg     540
aaaaaagaaa acagcaccct caatacatcg gaccaggaaa ttctgaataa atccaggaa      600
tcactgaaga atgcgaagaa accgatcgtc atcaccggac atgagatcat ctcttttggc     660
ctggaaaaaa cggtcacgca gttcatttct aagaccaaac tgcctatcac caccctgaac     720
ttcggcaaat ctagcgtcga tgaagcgctg ccgagttttc tgggtatcta atatggtacc     780
ctgtccgaac cgaacctgaa agaattcgtc gaaagcgcgg actttatcct gatgctgggc     840
gtgaaactga cggatagctc cacaggcgca tttacccacc atctgaacga gaataaaatg     900
atttccctga atatcgacga aggcaaaatc tttaacgagc gcatccagaa cttcgatttt     960
gaatctctga ttagttcgct gctggatctg tccgaaattg agtataaagg taaatatatt    1020
gataaaaaac aggaggattt tgtgccgtct aatgcgctgc tgagtcagga tcgtctgtgg    1080
caagccgtag aaaacctgac acagtctaat gaaacgattg ttgcggaaca gggaacttca    1140
tttttcggcg cctcatccat ttttctgaaa tccaaaagcc atttcattgg ccaaccgctg    1200
tgggggagta ttggttatac ctttccggcg gcgctgggtt cacagattgc agataaggaa    1260
tcacgccatc tgctgttttat tggtgacggc agcctgcagc tgactgtcca ggaactgggg    1320
ctggcgatcc gtgaaaaaat caatccgatt tgctttatca tcaataacga cggctacacc    1380
gtcgaacgcg aaattcatgg accgaatcaa agttacaatg acatcccgat gtggaactat    1440
```

-continued

```
agcaaactgc cggaatcctt tggcgcgaca gaggatcgcg tggtgagtaa aattgtgcgt    1500
acggaaaacg aatttgtgtc ggttatgaaa gaagcgcagg ctgacccgaa tcgcatgtat    1560
tggattgaac tgatcctggc aaaagaaggc gcaccgaaag ttctgaaaaa gatggggaaa    1620
ctgtttgcgg agcaaaataa aagctaa                                        1647
```

<210> SEQ ID NO 8
<211> LENGTH: 548
<212> TYPE: PRT
<213> ORGANISM: Lactococcus lactis

<400> SEQUENCE: 8

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335
```

```
Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 9
<211> LENGTH: 1047
<212> TYPE: DNA
<213> ORGANISM: Achromobacter xyloxidans

<400> SEQUENCE: 9
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180 gaagggtag cgtcatcga ggaagtgggc gagagtgtca cgcagttcaa gaaaggcgac      240
aaggtcctga tttcctgcgt cacttcttgc ggctcgtgcg actactgcaa gaagcagctt     300
tactcccatt gccgcgacgg cggtggatc ctgggttaca tgatcgatgg cgtgcaggcc      360
gaatacgtcc gcatcccgca tgccgacaac agcctctaca gatcccccca gacaattgac     420
gacgaaatcg ccgtcctgct gagcgacatc ctgcccaccg ccacgaaat cggcgtccag      480 tatgggaatg tccagccggg cgatgcggtg gctattgtcg gcgcgggccc cgtcggcatg     540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg gagtcgatgt tgcgatcgag     720
gcggtgggca taccgcgac ttgggacatc tgccaggaga tcgtcaagcc cggcgcgcac      780
atcgccaacg tcggcgtgca tggcgtcaag gttgacttcg agattcagaa gctctggatc     840
```

```
aagaaccTga cgaTcaccac gggacTggTg aacacgaaca cgacgcccaT gcTgaTgaag    900
gTcgccTcga ccgacaagcT TccgTTgaag aagaTgaTTa cccaTcgcTT cgagcTggcc    960
gagaTcgagc acgccTaTca ggTaTTccTc aaTggcgcca aggagaaggc gaTgaagaTc   1020
aTccTcTcga acgcaggcgc TgccTga                                      1047
```

<210> SEQ ID NO 10
<211> LENGTH: 348
<212> TYPE: PRT
<213> ORGANISM: Achromobacter xyloxidans

<400> SEQUENCE: 10

```
Met Lys Ala Leu Val Tyr His Gly Asp His Lys Ile Ser Leu Glu Asp
1               5                  10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
            35                  40                  45

Asn Pro Glu Val Ala Asp Gly Arg Ile Leu Gly His Glu Gly Val Gly
        50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335
```

Ala Met Lys Ile Ile Leu Ser Asn Ala Gly Ala Ala
            340                 345

<210> SEQ ID NO 11
<211> LENGTH: 1713
<212> TYPE: DNA
<213> ORGANISM: Bacillus subtilis

<400> SEQUENCE: 11

```
ttgacaaaag caacaaaaga acaaaaatcc cttgtgaaaa acagagggggc ggagcttgtt      60
gttgattgct tagtggagca aggtgtcaca catgtatttg cattccagg tgcaaaaatt      120
gatgcggtat ttgacgcttt acaagataaa ggacctgaaa ttatcgttgc ccggcacgaa      180
caaaacgcag cattcatggc ccaagcagtc ggccgtttaa ctggaaaacc gggagtcgtg      240
ttagtcacat caggaccggg tgcctctaac ttggcaacag gctgctgac agcgaacact      300
gaaggagacc ctgtcgttgc gcttgctgga aacgtgatcc gtgcagatcg tttaaaacgg      360
acacatcaat ctttggataa tgcggcgcta ttccagccga ttacaaaata cagtgtagaa      420
gttcaagatg taaaaaatat accggaagct gttacaaatg catttaggat agcgtcagca      480
gggcaggctg gggccgcttt tgtgagcttt ccgcaagatg ttgtgaatga agtcacaaat      540
acgaaaaacg tgcgtgctgt tgcagcgcca aaactcggtc ctgcagcaga tgatgcaatc      600
agtgcggcca tagcaaaaat ccaaacagca aaacttcctg tcgttttggt cggcatgaaa      660
ggcggaagac cggaagcaat taaagcggtt cgcaagcttt tgaaaaaggt tcagcttcca      720
tttgttgaaa catatcaagc tgccggtacc ctttctagag atttagagga tcaatatttt      780
ggccgtatcg gtttgttccg caaccagcct ggcgatttac tgctagagca ggcagatgtt      840
gttctgacga tcggctatga cccgattgaa tatgatccga aattctggaa tatcaatgga      900
gaccggacaa ttatccattt agacgagatt atcgctgaca ttgatcatgc ttaccagcct      960
gatcttgaat tgatcggtga cattccgtcc acgatcaatc atatcgaaca cgatgctgtg     1020
aaagtggaat ttgcagagcg tgagcagaaa atcctttctg atttaaaaca atatatgcat     1080
gaaggtgagc aggtgcctgc agattggaaa tcagacagag cgcaccctct tgaaatcgtt     1140
aaaagagttgc gtaatgcagt cgatgatcat gttacagtaa cttgcgatat cggttcgcac     1200
gccatttgga tgtcacgtta tttccgcagc tacgagccgt taacattaat gatcagtaac     1260
ggtatgcaaa cactcggcgt tgcgcttcct tgggcaatcg gcgcttcatt ggtgaaaccg     1320
ggagaaaaag tggtttctgt ctctggtgac ggcggttttct tattctcagc aatggaatta     1380
gagacagcag ttcgactaaa agcaccaatt gtacacattg tatggaacga cagcacatat     1440
gacatggttg cattccagca attgaaaaaa tataaccgta catctgcggt cgatttcgga     1500
aatatcgata tcgtgaaata tgcggaaagc ttcggagcaa ctggcttgcg cgtagaatca     1560
ccagaccagc tggcagatgt tctgcgtcaa ggcatgaacg ctgaaggtcc tgtcatcatc     1620
gatgtcccgg ttgactacag tgataacatt aatttagcaa gtgacaagct tccgaaagaa     1680
ttcggggaac tcatgaaaac gaaagctctc tag                                 1713
```

<210> SEQ ID NO 12
<211> LENGTH: 570
<212> TYPE: PRT
<213> ORGANISM: Bacillus subtilis

<400> SEQUENCE: 12

Met Thr Lys Ala Thr Lys Glu Gln Lys Ser Leu Val Lys Asn Arg Gly
1               5                   10                  15

```
Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
 50                  55                  60

Phe Met Ala Gln Ala Val Gly Arg Leu Thr Gly Lys Pro Gly Val Val
 65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
            115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
            165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
            195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
            245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
    275                 280                 285

Ile Glu Tyr Asp Pro Lys Phe Trp Asn Ile Asn Gly Asp Arg Thr Ile
    290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
            325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
    355                 360                 365

Trp Lys Ser Asp Arg Ala His Pro Leu Glu Ile Val Lys Glu Leu Arg
    370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
            405                 410                 415

Met Ile Ser Asn Gly Met Gln Thr Leu Gly Val Ala Leu Pro Trp Ala
            420                 425                 430
```

```
Ile Gly Ala Ser Leu Val Lys Pro Gly Glu Lys Val Val Ser Val Ser
            435                 440                 445
Gly Asp Gly Gly Phe Leu Phe Ser Ala Met Glu Leu Glu Thr Ala Val
        450                 455                 460
Arg Leu Lys Ala Pro Ile Val His Ile Val Trp Asn Asp Ser Thr Tyr
465                 470                 475                 480
Asp Met Val Ala Phe Gln Gln Leu Lys Lys Tyr Asn Arg Thr Ser Ala
                485                 490                 495
Val Asp Phe Gly Asn Ile Asp Ile Val Lys Tyr Ala Glu Ser Phe Gly
            500                 505                 510
Ala Thr Gly Leu Arg Val Glu Ser Pro Asp Gln Leu Ala Asp Val Leu
        515                 520                 525
Arg Gln Gly Met Asn Ala Glu Gly Pro Val Ile Ile Asp Val Pro Val
530                 535                 540
Asp Tyr Ser Asp Asn Ile Asn Leu Ala Ser Asp Lys Leu Pro Lys Glu
                545                 550                 555                 560
Phe Gly Glu Leu Met Lys Thr Lys Ala Leu
            565                 570

<210> SEQ ID NO 13
<211> LENGTH: 1188
<212> TYPE: DNA
<213> ORGANISM: Saccharomyces cerevisiae

<400> SEQUENCE: 13
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc caggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccgtaaggc tcacgaaaag gcccaagctt tggccgttgc cattggttcc     720
ggttacgttt accaaaccac tttcgaaaga gaagtcaact ctgacttgta cggtgaaaga     780
ggttgtttaa tgggtggtat ccacggtatg ttcttggctc aatacgacgt cttgagagaa     840
aacggtcact cccccatctga agctttcaac gaaaccgtcg aagaagctac ccaatctcta     900
tacccattga tcgtaagta cggtatggat tacatgtacg atgcttgttc caccaccgcc     960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
tggaaggttg gtaaggaagt cagaaagttg agaccagaaa ccaataa                  1188

<210> SEQ ID NO 14
<211> LENGTH: 395
<212> TYPE: PRT
```

<213> ORGANISM: Saccharomyces cerevisiae

<400> SEQUENCE: 14

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Tyr Ser
            20                  25                  30

Arg Pro Ala Ala Arg Phe Val Lys Pro Met Ile Thr Thr Arg Gly Leu
            35                  40                  45

Lys Gln Ile Asn Phe Gly Gly Thr Val Glu Thr Val Tyr Glu Arg Ala
        50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
370                 375                 380

Lys Glu Val Arg Lys Leu Arg Pro Glu Asn Gln
385                 390                 395
```

<210> SEQ ID NO 15
<211> LENGTH: 1014
<212> TYPE: DNA
<213> ORGANISM: artificial sequence
<220> FEATURE:
<223> OTHER INFORMATION: Mutant of Pseudomonas fluorescens ilvC coding region

<400> SEQUENCE: 15

```
atgaaggtgt tttacgataa agactgcgat ctgagcatca tccagggaaa gaaggttgct      60
attataggat atggttccca aggacacgca caagccttga acttgaaaga ttctggggtc     120
gacgtgacag taggtctgta taaaggtgct gctgatgcag caaaggctga agcacatggc     180
tttaaagtca cagatgttgc agcggctgtt gctggcgctg atttagtcat gattttaatt     240
ccagatgaat tcaatcgca attgtacaaa aatgaaatag aaccaaacat taagaagggc     300
gctaccttgg ccttcagtca tggatttgcc attcattaca atcaagtagt ccccagggca     360
gatttggacg ttattatgat tgcacctaag gctccggggc atactgttag gagcgaattt     420
gttaagggtg gtggtattcc agatttgatc gctatatacc aagacgttag cggaaacgct     480
aagaatgtag ctttaagcta cgcagcagga gttggtggcg ggagaacggg tataatagaa     540
accacttta aagacgagac tgagacagat ttatttggag aacaagcggt tctgtgcgga     600
ggaactgttg aattggttaa agcaggcttt gagacgcttg tcgaagcagg gtacgctccc     660
gaaatggcat acttcgaatg tctacatgaa ttgaagttga tagtagactt aatgtatgaa     720
ggtggtatag ctaatatgaa ctattccatt tcaaataatg cagaatatgg tgagtatgtc     780
accggacctg aagtcattaa cgcagaatca agacaagcca tgagaaatgc cttgaaacgt     840
atccaggacg gtgaatacgc taagatgttc ataagtgaag gcgctacggg ttacccgagt     900
atgactgcta aaagaagaaa caatgcagca catggtatcg aaattattgg tgaacagtta     960
aggtctatga tgccctggat cggtgctaat aagatcgtag acaaggcgaa aaat         1014
```

<210> SEQ ID NO 16
<211> LENGTH: 338
<212> TYPE: PRT
<213> ORGANISM: artificial sequence
<220> FEATURE:
<223> OTHER INFORMATION: mutant of Pseudomonas fluorescens protein

<400> SEQUENCE: 16

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125
```

```
Pro Lys Ala Pro Gly His Thr Val Arg Ser Glu Phe Val Lys Gly Gly
    130                 135                 140
Gly Ile Pro Asp Leu Ile Ala Ile Tyr Gln Asp Val Ser Gly Asn Ala
145                 150                 155                 160
Lys Asn Val Ala Leu Ser Tyr Ala Ala Ala Val Gly Gly Gly Arg Thr
                165                 170                 175
Gly Ile Ile Glu Thr Thr Phe Lys Asp Glu Thr Glu Thr Asp Leu Phe
            180                 185                 190
Gly Glu Gln Ala Val Leu Cys Gly Gly Thr Val Glu Leu Val Lys Ala
        195                 200                 205
Gly Phe Glu Thr Leu Val Glu Ala Gly Tyr Ala Pro Glu Met Ala Tyr
    210                 215                 220
Phe Glu Cys Leu His Glu Leu Lys Leu Ile Val Asp Leu Met Tyr Glu
225                 230                 235                 240
Gly Gly Ile Ala Asn Met Asn Tyr Ser Ile Ser Asn Ala Glu Tyr
                245                 250                 255
Gly Glu Tyr Val Thr Gly Pro Glu Val Ile Asn Ala Glu Ser Arg Gln
            260                 265                 270
Ala Met Arg Asn Ala Leu Lys Arg Ile Gln Asp Gly Glu Tyr Ala Lys
        275                 280                 285
Met Phe Ile Ser Glu Gly Ala Thr Gly Tyr Pro Ser Met Thr Ala Lys
    290                 295                 300
Arg Arg Asn Asn Ala Ala His Gly Ile Glu Ile Ile Gly Glu Gln Leu
305                 310                 315                 320
Arg Ser Met Met Pro Trp Ile Gly Ala Asn Lys Ile Val Asp Lys Ala
                325                 330                 335
Lys Asn
```

<210> SEQ ID NO 17
<211> LENGTH: 1713
<212> TYPE: DNA
<213> ORGANISM: Streptococcus mutans

<400> SEQUENCE: 17

```
atgactgaca aaaaaactct aaagactta  agaaatcgta gttctgttta cgattcaatg      60
gttaaatcac ctaatcgtgc tatgttgcgt gcaactggta tgcaagatga agactttgaa     120
aaacctatcg tcggtgtcat ttcaacttgg gctgaaaaca caccttgtaa tatccactta     180
catgactttg gtaaactagc caaagtcggt gttaaggaag ctggtgcttg gccagttcag     240
ttcggaacaa tcacggtttc tgatggaatc gccatgggaa cccaaggaat gcgtttctcc     300
ttgacatctc gtgatattat tgcagattct attgaagcag ccatgggagg tcataatgcg     360
gatgcttttg tagccattgg cggttgtgat aaaaacatgc cggttctgt  tatcgctatg     420
gctaacatgg atatcccagc cattttgct  tacggcggaa caattgcacc tggtaattta     480
gacggcaaag atatcgattt agtctctgtc tttgaaggtg tcggccattg gaaccacggc     540
gatatgacca agaagaagt  taaagctttg aatgtaatg  cttgtcccgg tcctggaggc     600
tgcggtggta tgtatactgc taacacaatg gcgacagcta ttgaagtttt gggacttagc     660
cttccgggtt catcttctca cccggctgaa tccgcagaaa agaaagcaga tattgaagaa     720
gctggtcgcg ctgttgtcaa aatgctcgaa atgggcttaa accttctga  cattttaacg     780
cgtgaagctt ttgaagatgc tattactgta actatggctc tgggaggttc aaccaactca     840
acccttcacc tcttagctat tgcccatgct gctaatgtgg aattgacact tgatgatttc     900
```

```
aatactttcc aagaaaaagt tcctcatttg gctgatttga aaccttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc agacggtgc cgttgccaaa    1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caagggcgg tcctggtatg cctgaaatgc tttcccttc atcaatgatt     1380
gttggtaaag ggcaaggtga aaagttgcc cttctgacag atggccgctt ctcaggtggt     1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gactttttgga agcctgaaga aactggcaaa aaa                                1713

<210> SEQ ID NO 18
<211> LENGTH: 571
<212> TYPE: PRT
<213> ORGANISM: Streptococcus mutans

<400> SEQUENCE: 18

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
                20                  25                  30

Gly Met Gln Asp Glu Asp Phe Glu Lys Pro Ile Val Gly Val Ile Ser
            35                  40                  45

Thr Trp Ala Glu Asn Thr Pro Cys Asn Ile His Leu His Asp Phe Gly
        50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
210                 215                 220

Ser Ser His Pro Ala Glu Ser Ala Glu Lys Lys Ala Asp Ile Glu Glu
```

```
                        225                 230                 235                 240
    Ala Gly Arg Ala Val Val Lys Met Leu Glu Met Gly Leu Lys Pro Ser
                    245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
        290                 295                 300

Glu Lys Val Pro His Leu Ala Asp Leu Lys Pro Ser Gly Gln Tyr Val
    305                 310                 315                 320

Phe Gln Asp Leu Tyr Lys Val Gly Val Pro Ala Val Met Lys Tyr
                    325                 330                 335

Leu Leu Lys Asn Gly Phe Leu His Gly Asp Arg Ile Thr Cys Thr Gly
                340                 345                 350

Lys Thr Val Ala Glu Asn Leu Lys Ala Phe Asp Asp Leu Thr Pro Gly
            355                 360                 365

Gln Lys Val Ile Met Pro Leu Glu Asn Pro Lys Arg Glu Asp Gly Pro
        370                 375                 380

Leu Ile Ile Leu His Gly Asn Leu Ala Pro Asp Gly Ala Val Ala Lys
    385                 390                 395                 400

Val Ser Gly Val Lys Val Arg Arg His Val Gly Pro Ala Lys Val Phe
                    405                 410                 415

Asn Ser Glu Glu Glu Ala Ile Glu Ala Val Leu Asn Asp Asp Ile Val
                420                 425                 430

Asp Gly Asp Val Val Val Arg Phe Val Gly Pro Lys Gly Gly Pro
            435                 440                 445

Gly Met Pro Glu Met Leu Ser Leu Ser Ser Met Ile Val Gly Lys Gly
        450                 455                 460

Gln Gly Glu Lys Val Ala Leu Leu Thr Asp Gly Arg Phe Ser Gly Gly
    465                 470                 475                 480

Thr Tyr Gly Leu Val Val Gly His Ile Ala Pro Glu Ala Gln Asp Gly
                    485                 490                 495

Gly Pro Ile Ala Tyr Leu Gln Thr Gly Asp Ile Val Thr Ile Asp Gln
                500                 505                 510

Asp Thr Lys Glu Leu His Phe Asp Ile Ser Asp Glu Glu Leu Lys His
            515                 520                 525

Arg Gln Glu Thr Ile Glu Leu Pro Pro Leu Tyr Ser Arg Gly Ile Leu
        530                 535                 540

Gly Lys Tyr Ala His Ile Val Ser Ser Ala Ser Arg Gly Ala Val Thr
    545                 550                 555                 560

Asp Phe Trp Lys Pro Glu Glu Thr Gly Lys Lys
                    565                 570

<210> SEQ ID NO 19
<211> LENGTH: 1644
<212> TYPE: DNA
<213> ORGANISM: artificial sequence
<220> FEATURE:
<223> OTHER INFORMATION: Bacillus subtilis kivD coding region codon
      optimized for expression is S. cerevisiae

<400> SEQUENCE: 19
atgtatacag taggtgacta tctgttggac agattacacg aattaggtat agaagaaata        60
ttcggagtac caggtgacta caatttgcaa tttctagatc aaattatttc acacaaagat       120
```

```
atgaaatggg tgggaaatgc taatgagtta aatgcctcct atatggccga cgggtacgca      180
agaacgaaaa aggctgcggc attcttgact acatttggtg ttggcgaatt atccgcagtt      240
aatggcttag cgggctccta tgctgagaac ctgcctgttg ttgagatcgt gggatctcct      300
acctcgaaag tgcagaacga aggtaagttt gttcaccata cgttggctga tggtgatttc      360
aagcacttta tgaagatgca cgaaccggtt actgctgcca ggactttatt gacagccgag      420
aatgcaactg ttgaaattga tagtgtgttg tctgccttac taaaggaaag aaagccggtt      480
tacatcaatt tacctgtaga tgtagctgcc gctaaggctg aaaaaccatc cttgcctctt      540
aagaaggaaa attccacgtc gaatacatct gatcaagaga ttctgaacaa atacaggaa       600 agtctgaaga atgccaagaa accaattgta atcacaggcc atgaaattat atcgttcggc      660
ctagagaaga ctgttactca gtttatttca aagactaagt tacctattac tactttgaac      720
tttggtaaat catctgttga tgaagcattg ccctcatttt tggggattta caacggtact      780
ctgtcagagc caaacttgaa ggaatttgtg aatctgctg attttattct tatgttgggt       840
gtaaagctta ccgattctag tacgggtgca tttactcacc atcttaatga aaataaaatg      900
atttccttga atatcgatga aggtaaaatt tcaacgaaa gaatccaaaa tttcgacttc       960
gaatccctga tatcatctct tcttgacttg tccgaaattg aatataaagg caagtacata     1020
gataaaaagc aagaagattt tgtaccttct aacgcgctgt tgtcacaaga tagactgtgg     1080
caagctgtcg aaaatttgac ccaaagtaat gagacgatcg tggctgaaca aggcacttct     1140
ttcttcggtg cctcatctat atttctgaaa tcgaaatcac attttattgg tcaacccttg     1200
tggggatcta taggatacac tttccccgca gctctaggca gccaaattgc agataaagaa     1260
tctagacatt tattgtttat cggagatgga tcattgcaac tgactgtcca agaattagga     1320
ctagccatta gagagaagat aaacccaatc tgctttatca ttaataacga tggttacacg     1380
gttgagaggg aaattcatgg tccgaaccag agttataatg acattcctat gtggaattac     1440
tcaaaactgc cagaaagttt cggggcaacg gaagacagag ttgtgtccaa aattgtgaga     1500
acagaaaatg aattcgtatc cgtgatgaaa gaagctcaag cagatccaaa taggatgtat     1560
tggatagaac ttattctagc aaaggagggt gcacctaaag ttttgaaaaa gatgggtaag     1620
ttatttgcag aacaaaacaa gagc                                            1644
```

<210> SEQ ID NO 20
<211> LENGTH: 548
<212> TYPE: PRT
<213> ORGANISM: Bacillus subtilis

<400> SEQUENCE: 20

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

-continued

```
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
        115                 120                 125
Pro Val Thr Ala Ala Arg Thr Leu Leu Thr Ala Glu Asn Ala Thr Val
    130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Lys Ala Glu Lys Pro
                165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
        195                 200                 205
Ile Val Ile Thr Gly His Glu Ile Ile Ser Phe Gly Leu Glu Lys Thr
    210                 215                 220
Val Thr Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
                245                 250                 255
Tyr Asn Gly Thr Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
        275                 280                 285
Gly Ala Phe Thr His His Leu Asn Glu Asn Lys Met Ile Ser Leu Asn
    290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
                325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Ser Lys Ser His Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
        435                 440                 445
Pro Ile Cys Phe Ile Ile Asn Asn Asp Gly Tyr Thr Val Glu Arg Glu
    450                 455                 460
Ile His Gly Pro Asn Gln Ser Tyr Asn Asp Ile Pro Met Trp Asn Tyr
465                 470                 475                 480
Ser Lys Leu Pro Glu Ser Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Pro Asn Arg Met Tyr Trp Ile Glu Leu Ile Leu Ala Lys
```

```
              515                 520                 525
Glu Gly Ala Pro Lys Val Leu Lys Lys Met Gly Lys Leu Phe Ala Glu
      530                 535                 540

Gln Asn Lys Ser
545

<210> SEQ ID NO 21
<211> LENGTH: 2145
<212> TYPE: DNA
<213> ORGANISM: artificial sequence
<220> FEATURE:
<223> OTHER INFORMATION: constructed chimeric gene

<400> SEQUENCE: 21
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatatatata     300
tatagccata gtgatgtcta agtaaccttt atggtatatt tcttaatgtg aaagatact      360 agcgcgcgca cccacacaca agcttcgtct tttcttgaag aaaagaggaa gctcgctaaa     420
tgggattcca ctttccgttc cctgccagct gatggaaaaa ggttagtgga acgatgaaga     480 ataaaagag agatccactg aggtgaaatt tcagctgaca gcgagtttca tgatcgtgat     540
gaacaatggt aacgagttgt ggctgttgcc agggagggtg gttctcaact tttaatgtat     600
ggccaaatcg ctacttgggt ttgttatata caaagaaga ataatgaac tgattctctt      660 cctccttctt gtcctttctt aattctgttg taattacctt cctttgtaat ttttttttgta    720 attattcttc ttaataatcc aaacaaacac acatattaca atagctagct gaggatgaag     780
gcattagttt atcatgggga tcacaaaatt tcgttagaag acaaaccaaa acccactctg     840
cagaaaccaa cagacgttgt ggttagggtg ttgaaaacaa caatttgcgg tactgacttg     900
ggaatataca aagtaagaa tcctgaagtg cagatggca gaatcctggg tcatgagggc       960
gttggcgtca ttgaagaagt gggcgaatcc gtgacacaat tcaaaagggg ggataaagtt    1020
ttaatctcct gcgttactag ctgtggatcg tgtgattatt gcaagaagca actgtattca    1080
cactgtagag acggtggctg gatttaggt tacatgatcg acggtgtcca agccgaatac    1140
gtcagaatac cacatgctga caattcattg tataagatcc cgcaaactat cgatgatgaa    1200
attgcagtac tactgtccga tattttacct actggacatg aaattggtgt tcaatatggt    1260
aacgttcaac caggcgatgc tgtagcaatt gtaggagcag gtcctgttgg aatgtcagtt    1320
ttgttaactg ctcaatttta ctcgcctagt accattattg ttatcgacat ggacgaaaac    1380
cgtttacaat tagcgaagga gcttggggcc acacacacta ttaactccgg tactgaaaat    1440
gttgtcgaag ctgtgcatcg tatagcagcc gaaggagtgg atgtagcaat agaagctgtt    1500 ggtataccog caacctggga catctgtcag gaaattgtaa acccggcgc tcatattgcc    1560 aacgtgggag ttcatggtgt taaggtggac tttgaaattc aaaagttgtg gattaagaat    1620
ctaaccatca ccactggttt ggttaacact aatactaccc caatgttgat gaaggtagcc    1680
tctactgata aattgccttt aaagaaaatg attactcaca ggtttgagtt agctgaaatc    1740
gaacacgcat atcaggtttt cttgaatggc gctaaagaaa aagctatgaa gattattcta    1800
tctaatgcag gtgccgccta attaattaag agtaagcgaa tttcttatga tttatgattt    1860
```

```
ttattattaa ataagttata aaaaaaataa gtgtatacaa attttaaagt gactcttagg   1920
ttttaaaacg aaaattctta ttcttgagta actctttcct gtaggtcagg ttgctttctc   1980
aggtatagca tgaggtcgct cttattgacc acacctctac cggcatgccg agcaaatgcc   2040
tgcaaatcgc tccccatttc acccaattgt agatatgcta actccagcaa tgagttgatg   2100
aatctcggtg tgtattttat gtcctcagag gacaacacct gtggt                   2145
```

<210> SEQ ID NO 22
<211> LENGTH: 4280
<212> TYPE: DNA
<213> ORGANISM: artificial sequence
<220> FEATURE:
<223> OTHER INFORMATION: vector

<400> SEQUENCE: 22

```
ggggatcctc tagagtcgac ctgcaggcat gcaagcttgg cgtaatcatg gtcatagctg     60
tttcctgtgt gaaattgtta tccgctcaca attccacaca catacgagc cggaagcata    120 aagtgtaaag cctggggtgc ctaatgagtg agctaactca cattaattgc gttgcgctca    180
ctgcccgctt tccagtcggg aaacctgtcg tgccagctgc attaatgaat cggccaacgc    240
gcggggagag gcggtttgcg tattgggcgc tcttccgctt cctcgctcac tgactcgctg    300
cgctcggtcg ttcggctgcg gcgagcggta tcagctcact caaaggcggt aatacggtta    360
tccacagaat caggggataa cgcaggaaag aacatgtgag caaaaggcca gcaaaaggcc    420
aggaaccgta aaaaggccgc gttgctggcg ttttttccata ggctccgccc ccctgacgag    480
catcacaaaa atcgacgctc aagtcagagg tggcgaaacc cgacaggact ataaagatac    540
caggcgtttc ccctggaag ctccctcgtg cgctctcctg ttccgaccct gccgcttacc     600
ggatacctgt ccgcctttct cccttcggga agcgtggcgc tttctcatag ctcacgctgt    660
aggtatctca gttcggtgta ggtcgttcgc tccaagctgg gctgtgtgca cgaaccccccc   720 gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
```

```
agatgctttt ctgtgactgg tgagtactca accaagtcat tctgagaata gtgtatgcgg    1800
cgaccgagtt gctcttgccc ggcgtcaata cgggataata ccgcgccaca tagcagaact    1860
ttaaaagtgc tcatcattgg aaaacgttct tcggggcgaa aactctcaag gatcttaccg    1920
ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040
ataagggcga cacggaaatg ttgaatactc atactcttcc tttttcaata ttattgaagc    2100
atttatcagg gttattgtct catgagcgga tacatatttg aatgtattta gaaaaataaa    2160
caaatagggg ttccgcgcac atttccccga aaagtgccac ctgacgtcta agaaaccatt    2220
attatcatga cattaaccta taaaaatagg cgtatcacga ggccctttcg tctcgcgcgt    2280
ttcggtgatg acggtgaaaa cctctgacac atgcagctcc cggagacggt cacagcttgt    2340
ctgtaagcgg atgccgggag cagacaagcc cgtcagggcg cgtcagcggg tgttggcggg    2400
tgtcggggct ggcttaacta tgcggcatca gagcagattg tactgagagt gcaccatatg    2460
cggtgtgaaa taccgcacag atgcgtaagg agaaaatacc gcatcaggcg ccattcgcca    2520
ttcaggctgc gcaactgttg ggaagggcga tcggtgcggg cctcttcgct attacgccag    2580
ctggcgaaag gggatgtgc tgcaaggcga ttaagttggg taacgccagg ttttcccag    2640
tcacgacgtt gtaaaacgac ggccagtgaa ttcgagctcg gtaccccgg ctctgagaca    2700
gtagtaggtt agtcatcgct ctaccgacgc gcaggaaaag aaagaagcat tgcggattac    2760
gtattctaat gttcagcccg cggaacgcca gcaaatcacc acccatgcgc atgatactga    2820
gtcttgtaca cgctgggctt ccagtgtact gagagtgcac cataccacag cttttcaatt    2880
caattcatca tttttttttt attctttttt ttgatttcgg tttctttgaa attttttga    2940
ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata atcatgtcg aaagctacat ataaggaacg    3120
tgctgctact catcctagtc ctgttgctgc caagctattt aatatcatgc acgaaaagca    3180
aacaaacttg tgtgcttcat tggatgttcg taccaccaag gaattactgg agttagttga    3240
agcattaggt cccaaaattt gtttactaaa aacacatgtg gatatcttga ctgatttttc    3300
catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg gcccaggtat    3480
tgttagcggt ttgaagcagg cggcagaaga agtaacaaag gaacctagag gccttttgat    3540
gttagcagaa ttgtcatgca agggctccct atctactgga gaatatacta agggtactgt    3600
tgacattgcg aagagcgaca aagattttgt tatcggcttt attgctcaaa gagacatggg    3660
tggaagagat gaaggttacg attggttgat tatgacaccc ggtgtgggtt tagatgacaa    3720
gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta taagtaaatg catgtatact aaactcacaa attagagctt caatttaatt    3960
atatcagtta ttaccctatg cggtgtgaaa taccgcacag atgcgtaagg agaaaatacc    4020
gcatcaggaa attgtaaacg ttaatatttt gttaaaattc gcgttaaatt tttgttaaat    4080
cagctcattt tttaaccaat aggccgaaat cggcaaaatc ttcagcccgc ggaacgccag    4140
```

| caaatcacca cccatgcgca tgatactgag tcttgtacac gctgggcttc cagtgatgat | 4200 |
| acaacgagtt agccaaggtg agcacggatg tctaaattag aattacgttt taatatcttt | 4260 |
| ttttccatat ctagggctag | 4280 |

```
<210> SEQ ID NO 23
<211> LENGTH: 30
<212> TYPE: DNA
<213> ORGANISM: artificial sequence
<220> FEATURE:
<223> OTHER INFORMATION: primer

<400> SEQUENCE: 23
```

| gcatgcttgc atttagtcgt gcaatgtatg | 30 |

```
<210> SEQ ID NO 24
<211> LENGTH: 54
<212> TYPE: DNA
<213> ORGANISM: artificial sequence
<220> FEATURE:
<223> OTHER INFORMATION: primer

<400> SEQUENCE: 24
```

| gaacattaga atacgtaatc cgcaatgcac tagtaccaca ggtgttgtcc tctg | 54 |

```
<210> SEQ ID NO 25
<211> LENGTH: 54
<212> TYPE: DNA
<213> ORGANISM: artificial sequence
<220> FEATURE:
<223> OTHER INFORMATION: primer

<400> SEQUENCE: 25
```

| cagaggacaa cacctgtggt actagtgcat tgcggattac gtattctaat gttc | 54 |

```
<210> SEQ ID NO 26
<211> LENGTH: 28
<212> TYPE: DNA
<213> ORGANISM: artificial sequence
<220> FEATURE:
<223> OTHER INFORMATION: primer

<400> SEQUENCE: 26
```

| caccttggct aactcgttgt atcatcac | 28 |

```
<210> SEQ ID NO 27
<211> LENGTH: 100
<212> TYPE: DNA
<213> ORGANISM: artificial sequence
<220> FEATURE:
<223> OTHER INFORMATION: primer

<400> SEQUENCE: 27
```

| ttttaagccg aatgagtgac agaaaaagcc cacaacttat caagtgatat tgaacaaagg | 60 |
| gcgaaacttc gcatgcttgc atttagtcgt gcaatgtatg | 100 |

```
<210> SEQ ID NO 28
<211> LENGTH: 98
<212> TYPE: DNA
<213> ORGANISM: artificial sequence
<220> FEATURE:
<223> OTHER INFORMATION: primer

<400> SEQUENCE: 28
```

```
cccaattggt aaatattcaa caagagacgc gcagtacgta acatgcgaat tgcgtaattc    60
acggcgataa caccttggct aactcgttgt atcatcac                            98

<210> SEQ ID NO 29
<211> LENGTH: 28
<212> TYPE: DNA
<213> ORGANISM: artificial sequence
<220> FEATURE:
<223> OTHER INFORMATION: primer

<400> SEQUENCE: 29 tcggttttg caatatgacc tgtgggcc                                        28

<210> SEQ ID NO 30
<211> LENGTH: 29
<212> TYPE: DNA
<213> ORGANISM: artificial sequence
<220> FEATURE:
<223> OTHER INFORMATION: primer

<400> SEQUENCE: 30
caaaagccca tgtcccacac caaaggatg                                      29

<210> SEQ ID NO 31
<211> LENGTH: 26
<212> TYPE: DNA
<213> ORGANISM: artificial sequence
<220> FEATURE:
<223> OTHER INFORMATION: primer

<400> SEQUENCE: 31
caccatcgcg cgtgcatcac tgcatg                                         26

<210> SEQ ID NO 32
<211> LENGTH: 22
<212> TYPE: DNA
<213> ORGANISM: artificial sequence
<220> FEATURE:
<223> OTHER INFORMATION: primer

<400> SEQUENCE: 32
gagaagatgc ggccagcaaa ac                                             22

<210> SEQ ID NO 33
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 33
atgactgaca aaaaaactct taaagactta agaaatcgta gttctgttta cgattcaatg    60
gttaaatcac ctaatcgtgc tatgttgcgt gcaactggta tgcaagatga agactttgaa   120
aaacctatcg tcggtgtcat ttcaacttgg gctgaaaaca caccttgtaa tatccactta   180
catgactttg gtaaactagc caaagtcggt gttaaggaag ctggtgcttg gccagttcag   240
ttcggaacaa tcacggtttc tgatggaatc gccatgggaa cccaaggaat gcgtttctcc   300
ttgacatctc gtgatattat tgcagattct attgaagcag ccatgggagg tcataatgcg   360
gatgcttttg tagccattgg cggttgtgat aaaaacatgc ccggttctgt tatcgctatg   420
gctaacatgg atatcccagc cattttttgct tacggcggaa caattgcacc tggtaattta   480
gacggcaaag atatcgattt agtctctgtc tttgaaggtg tcggccattg gaaccacggc   540
```

```
gatatgacca aagaagaagt taaagctttg aatgtaatg cttgtcccgg tcctggaggc      600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg   780
cgtgaagctt ttgaagatgc tattactgta actatggctc tgggaggttc aaccaactca    840
acccttcacc tcttagctat tgcccatgct gctaatgtgg aattgacact tgatgatttc   900
aatactttcc aagaaaaagt tcctcatttg gctgatttga aaccttctgg tcaatatgta   960
ttccaagacc tttacaaggt cggagggta ccagcagtta tgaaatatct ccttaaaaat    1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttcccttc atcaatgatt    1380 gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca    1680
gacttttgga agcctgaaga aactggcaaa aaatgttgtc ctggttgctg tggttaagcg   1740
gccgcgttaa ttcaaattaa ttgatatagt ttttaatga gtattgaatc tgtttagaaa    1800
taatggaata ttattttat ttatttattt atattattgg tcggctcttt tcttctgaag    1860
gtcaatgaca aaatgatatg aaggaaataa tgatttctaa aattttacaa cgtaagatat    1920
ttttacaaaa gcctagctca tcttttgtca tgcactattt tactcacgct tgaaattaac   1980
ggccagtcca ctgcggagtc atttcaaagt catcctaatc gatctatcgt ttttgatagc    2040
tcattttgga gttcgcgatt gtcttctgtt attcacaact gttttaattt ttatttcatt    2100
ctggaactct tcgagttctt tgtaaagtct ttcatagtag cttactttat cctccaacat    2160
atttaacttc atgtcaattt cggctcttaa attttccaca tcatcaagtt caacatcatc    2220
ttttaacttg aatttattct ctagctcttc caaccaagcc tcattgctcc ttgatttact    2280
ggtgaaaagt gatacactt gcgcgcaatc caggtcaaaa cttcctgca aagaattcac      2340 caatttctcg acatcatagt acaatttgtt ttgttctccc atcacaattt aatatacctg    2400
atggattctt atgaagcgct gggtaatgga cgtgtcactc tacttcgcct ttttccctac    2460 tcctttagt acggaagaca atgctaataa ataagagggt aataataata ttattaatcg    2520 gcaaaaaga ttaaacgcca agcgtttaat tatcagaaag caaacgtcgt accaatcctt     2580
gaatgcttcc caattgtata ttaagagtca tcacagcaac atattcttgt tattaaatta    2640
attattattg attttgata ttgtataaaa aaaccaaata tgtataaaaa aagtgaataa     2700
aaaataccaa gtatggagaa atatattaga agtctatacg ttaaa                   2745

<210> SEQ ID NO 34
<211> LENGTH: 99
<212> TYPE: DNA
```

```
<213> ORGANISM: artificial sequence
<220> FEATURE:
<223> OTHER INFORMATION: primer

<400> SEQUENCE: 34
tcctttctca attattattt tctactcata acctcacgca aataacaca gtcaaatcaa    60 tcaaagtatg actgacaaaa aaactcttaa agacttaag                          99

<210> SEQ ID NO 35
<211> LENGTH: 77
<212> TYPE: DNA
<213> ORGANISM: artificial sequence
<220> FEATURE:
<223> OTHER INFORMATION: primer

<400> SEQUENCE: 35
gaacattaga atacgtaatc cgcaatgctt ctttcttttc cgtttaacgt atagacttct    60
aatatatttc tccatac                                                  77

<210> SEQ ID NO 36
<211> LENGTH: 45
<212> TYPE: DNA
<213> ORGANISM: artificial sequence
<220> FEATURE:
<223> OTHER INFORMATION: primer

<400> SEQUENCE: 36
aaacggaaaa gaaagaagca ttgcggatta cgtattctaa tgttc                   45

<210> SEQ ID NO 37
<211> LENGTH: 88
<212> TYPE: DNA
<213> ORGANISM: artificial sequence
<220> FEATURE:
<223> OTHER INFORMATION: primer

<400> SEQUENCE: 37 tattttcgt tacataaaaa tgcttataaa actttaacta ataattagag attaaatcgc     60
caccttggct aactcgttgt atcatcac                                      88

<210> SEQ ID NO 38
<211> LENGTH: 27
<212> TYPE: DNA
<213> ORGANISM: artificial sequence
<220> FEATURE:
<223> OTHER INFORMATION: primer

<400> SEQUENCE: 38
gacttttgga agcctgaaga aactggc                                       27

<210> SEQ ID NO 39
<211> LENGTH: 20
<212> TYPE: DNA
<213> ORGANISM: artificial sequence
<220> FEATURE:
<223> OTHER INFORMATION: primer

<400> SEQUENCE: 39
cttggcagca acaggactag                                               20

<210> SEQ ID NO 40
<211> LENGTH: 26
<212> TYPE: DNA
<213> ORGANISM: artificial sequence
```

```
<220> FEATURE:
<223> OTHER INFORMATION: primer

<400> SEQUENCE: 40
ccaggccaat tcaacagact gtcggc                                        26

<210> SEQ ID NO 41
<211> LENGTH: 2347
<212> TYPE: DNA
<213> ORGANISM: artificial sequence
<220> FEATURE:
<223> OTHER INFORMATION: constructed URA3 marker with flanking
      homologous repeat sequences for HIS gene replacement and marker
      excision

<400> SEQUENCE: 41
gcattgcgga ttacgtattc taatgttcag gtgctggaag aagagctgct taaccgccgc      60
gcccagggtg aagatccacg ctactttacc ctgcgtcgtc tggatttcgg cggctgtcgt     120
cttttcgctg gcaacgccggt tgatgaagcc tgggacggtc cgctctcctt aaacggtaaa    180
cgtatcgcca cctcttatcc tcacctgctc aagcgttatc tcgaccagaa aggcatctct    240
tttaaatcct gcttactgaa cggttctgtt gaagtcgccc cgcgtgccgg actggcggat    300
gcgatttgcg atctggtttc caccggtgcc acgctggaag ctaacggcct gcgcgaagtc    360
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac cataccacag ctttccaatt caattcatca ttttttttt attcttttt    600 ttgatttcgg tttctttgaa atttttttga ttcggtaatc tccgaacaga aggaagaacg    660
aaggaaggag cacagactta gattggtata tatacgcata tgtagtgttg aagaaacatg    720
aaattgccca gtattcttaa cccaactgca cagaacaaaa acctgcagga acgaagata    780 aatcatgtcg aaagctacat ataaggaacg tgctgctact catcctagtc ctgttgctgc    840
caagctattt aatatcatgc acgaaaagca aacaaacttg tgtgcttcat tggatgttcg    900
taccaccaag gaattactgg agttagttga agcattaggt cccaaaattt gtttactaaa    960
aacacatgtg gatatcttga ctgattttc catggagggc acagttaagc cgctaaaggc    1020
attatccgcc aagtacaatt ttttactctt cgaagacaga aaatttgctg acattggtaa    1080
tacagtcaaa ttgcagtact ctgcgggtgt atacagaata gcagaatggg cagacattac    1140
gaatgcacac ggtgtggtgg cccaggtat tgttagcggt ttgaagcagg cggcagaaga    1200
agtaacaaag gaacctagag gccttttgat gttagcagaa ttgtcatgca agggctccct    1260
atctactgga gaatatacta agggtactgt tgacattgcg aagagcgaca agatttttgt    1320
tatcggcttt attgctcaaa gagacatggg tggaagagat gaaggttacg attggttgat    1380
tatgacaccc ggtgtgggtt tagatgacaa gggagacgca ttgggtcaac agtatagaac    1440
cgtggatgat gtggtctcta caggatctga cattattatt gttggaagag gactatttgc    1500
aaagggaagg gatgctaagg tagagggtga acgttacaga aaagcaggct gggaagcata    1560
tttgagaaga tgcggccagc aaaactaaaa aactgtatta taagtaaatg catgtatact    1620
aaactcacaa attagagctt caatttaatt atatcagtta ttaccctatg cggtgtgaaa    1680
taccgcacag atgcgtaagg agaaaatacc gcatcaggaa attgtaaacg ttaatatttt    1740
gttaaaattc gcgttaaatt tttgttaaat cagctcattt tttaaccaat aggccgaaat    1800
```

| | | |
|---|---|---|
| cggcaaaatc tctagagtgc tggaagaaga gctgcttaac cgccgcgccc agggtgaaga | 1860 | |
| tccacgctac tttaccctgc gtcgtctgga tttcggcggc tgtcgtcttt cgctggcaac | 1920 | |
| gccggttgat gaagcctggg acggtccgct ctccttaaac ggtaaacgta tcgccacctc | 1980 | |
| ttatcctcac ctgctcaagc gttatctcga ccagaaaggc atctctttta aatcctgctt | 2040 | |
| actgaacggt tctgttgaag tcgccccgcg tgccggactg gcggatgcga tttgcgatct | 2100 | |
| ggtttccacc ggtgccacgc tggaagctaa cggcctgcgc gaagtcgaag ttatctatcg | 2160 | |
| ctcgaaagcc tgcctgattc aacgcgatgg cgaaatggaa gaatccaaac agcaactgat | 2220 | |
| cgacaaactg ctgacccgta ttcagggtgt gatccaggcg cgcgaatcaa aatacatcat | 2280 | |
| gatgcacgca ccgaccgaac gtctggatga agtcatccag tgatgataca acgagttagc | 2340 | |
| caaggtg | 2347 | |

<210> SEQ ID NO 42
<211> LENGTH: 80
<212> TYPE: DNA
<213> ORGANISM: artificial sequence
<220> FEATURE:
<223> OTHER INFORMATION: primer

<400> SEQUENCE: 42

| | |
|---|---|
| cttcgaagaa tatactaaaa aatgagcagg caagataaac gaaggcaaag gcattgcgga | 60 |
| ttacgtattc taatgttcag | 80 |

<210> SEQ ID NO 43
<211> LENGTH: 80
<212> TYPE: DNA
<213> ORGANISM: artificial sequence
<220> FEATURE:
<223> OTHER INFORMATION: primer

<400> SEQUENCE: 43

| | |
|---|---|
| cttcgaagaa tatactaaaa aatgagcagg caagataaac gaaggcaaag gcattgcgga | 60 |
| ttacgtattc taatgttcag | 80 |

<210> SEQ ID NO 44
<211> LENGTH: 26
<212> TYPE: DNA
<213> ORGANISM: artificial sequence
<220> FEATURE:
<223> OTHER INFORMATION: primer

<400> SEQUENCE: 44

| | |
|---|---|
| gacttgaata atgcagcggc gcttgc | 26 |

<210> SEQ ID NO 45
<211> LENGTH: 30
<212> TYPE: DNA
<213> ORGANISM: artificial sequence
<220> FEATURE:
<223> OTHER INFORMATION: primer

<400> SEQUENCE: 45

| | |
|---|---|
| ccaccctctt caattagcta agatcatagc | 30 |

<210> SEQ ID NO 46
<211> LENGTH: 25
<212> TYPE: DNA
<213> ORGANISM: artificial sequence
<220> FEATURE:
<223> OTHER INFORMATION: primer

<400> SEQUENCE: 46
aaaaattgat tctcatcgta aatgc 25

<210> SEQ ID NO 47
<211> LENGTH: 20
<212> TYPE: DNA
<213> ORGANISM: artificial sequence
<220> FEATURE:
<223> OTHER INFORMATION: primer

<400> SEQUENCE: 47
ctgcagcgag gagccgtaat 20

<210> SEQ ID NO 48
<211> LENGTH: 16387
<212> TYPE: DNA
<213> ORGANISM: artificial sequence
<220> FEATURE:
<223> OTHER INFORMATION: plasmid construct

<400> SEQUENCE: 48

```
tcccattacc gacatttggg cgctatacgt gcatatgttc atgtatgtat ctgtatttaa      60
aacactttg tattattttt cctcatatat gtgtataggt ttatacggat gatttaatta     120
ttacttcacc acccttttatt tcaggctgat atcttagcct tgttactagt tagaaaaga    180
cattttttgct gtcagtcact gtcaagagat tcttttgctg gcatttcttc tagaagcaaa   240
aagagcgatg cgtctttttcc gctgaaccgt tccagcaaaa aagactacca acgcaatatg   300
gattgtcaga atcatataaa agagaagcaa ataactcctt gtcttgtatc aattgcatta   360
taatatcttc ttgttagtgc aatatcatat agaagtcatc gaaatagata ttaagaaaaa   420
caaactgtac aatcaatcaa tcaatcatcg ctgaggatgt tgacaaaagc aacaaaagaa   480
caaaaatccc ttgtgaaaaa cagaggggcg gagcttgttg ttgattgctt agtggagcaa   540
ggtgtcacac atgtatttgg cattccaggt gcaaaaattg atgcggtatt tgacgcttta   600
caagataaag gacctgaaat tatcgttgcc cggcacgaac aaaacgcagc attcatggcc   660
caagcagtcg gccgtttaac tggaaaaccg ggagtcgtgt tagtcacatc aggaccgggt   720
gcctctaact tggcaacagg cctgctgaca gcgaacactg aaggagaccc tgtcgttgcg   780
cttgctggaa acgtgatccg tgcagatcgt ttaaaacgga cacatcaatc tttgataat   840
gcggcgctat tccagccgat tacaaaatac agtgtagaag ttcaagatgt aaaaaatata   900
ccggaagctg ttacaaatgc atttaggata gcgtcagcag gcaggctgg ggccgctttt   960
gtgagctttc gcaagatgt tgtgaatgaa gtcacaaata cgaaaaacgt gcgtgctgtt  1020
gcagcgccaa aactcggtcc tgcagcagat gatgcaatca gtgcggccat agcaaaaatc  1080
caaacagcaa aacttcctgt cgttttggtc ggcatgaaag gcggaagacc ggaagcaatt  1140
aaagcggttc gcaagctttt gaaaaaggtt cagcttccat tgttgaaaac atatcaagct  1200
gccggtaccc tttctagaga tttagaggat caatattttg gccgtatcgg tttgttccgc  1260
aaccagcctg gcgatttact gctagagcag gcagatgttg ttctgacgat cggctatgac  1320
ccgattgaat atgatccgaa attctggaat atcaatggag accggacaat tatccattta  1380
gacgagatta tcgctgacat tgatcatgct taccagcctg atcttgaatt gatcggtgac  1440
attccgtcca cgatcaatca tatcgaacac gatgctgtga agtgaatt tgcagagcgt  1500
gagcagaaaa tccttttctga tttaaaacaa tatatgcatg aaggtgagca ggtgcctgca  1560
```

```
gattggaaat cagacagagc gcaccctctt gaaatcgtta aagagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280 ttatttttt atagttatgt tagtattaag aacgttattt atatttcaaa ttttttctttt    2340 ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcaggcat ttgctcggca tgccggtaga    2580
ggtgtggtca ataagagcga cctcatgcta tacctgagaa agcaacctga cctacaggaa    2640
agagttactc aagaataaga atttcgtttt aaaacctaa gagtcacttt aaaatttgta    2700
tacacttatt tttttataa cttatttaat aataaaaatc ataaatcata agaaattcgc    2760
ttactcttaa ttaatcaagc atctaaaaca caaccgttgg aagcgttgga aaccaactta    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
ataatctcat cgccgtctct gaccaacccg ataggaccac cttcagcggc ttcgggaaca    3000
atgtggccga ttaagaaccc gtgagaacca ccagagaatc taccatcagt caacaatgca    3060
acatctttac ccaaaccgta acccatcaga gcagaggaag gctttagcat ttcaggcata    3120
cctggtgcac ctcttggacc ttcatatctg ataacaacaa cggttttttc acccttcttg    3180
atttcacctc tttccaaggc ttcaataaag gcaccttcct cttcgaacac acgtgctcta    3240
cccttgaagt aagtaccttc cttaccggta attttaccca cagctccacc tggtgccaat    3300
gaaccgtaca gaatttgcaa gtgaccgttg gccttgattg ggtgggagag tggcttaata    3360
atctcttgtc cttcaggtag gcttggtgct ttctttgcac gttctgccaa agtgtcaccg    3420
gtaacagtca ttgtgttacc gtgcaacatg ttgttttcat atagatactt aatcacagat    3480
tgggtaccac caacgttaat caaatcggcc atgacgtatt taccagaagg tttgaagtca    3540
ccgatcaatg gtgtagtatc actgattctt tggaaatcat ctggtgacaa cttgacaccc    3600
gcagagtgag caacagccac caaatgcaaa acagcattag tggacccacc ggttgcaacg    3660
acataagtaa tggcgttttc aaaagcctct tttgtgagga tatcacgagg taaaataccc    3720
aattccattg tcttcttgat gtattcacca atgttgtcac actcagctaa cttctccttg    3780
gaaacggctg ggaaggaaga ggagtttgga atggtcaaac ctagcacttc agcggcagaa    3840
gccattgtgt tggcagtata cataccacca caagaaccag gacctgggca tgcatgttcc    3900
acaacatctt ctctttcttc ttcagtgaat tgcttggaaa tatattcacc gtaggattgg    3960
```

-continued

```
aacgcagaga cgatatcgat gttttagag atcctgttaa aacctctagt ggagtagtag      4020
atgtaatcaa tgaagcggaa gccaaaagac cagagtagag gcctatagaa gaaactgcga      4080
tacctttgt gatggctaaa caaacagaca tcttttata tgtttttact tctgtatatc       4140
gtgaagtagt aagtgataag cgaatttggc taagaacgtt gtaagtgaac aagggacctc      4200
ttttgccttt caaaaaagga ttaaatggag ttaatcattg agatttagtt ttcgttagat      4260
tctgtatccc taaataactc ccttacccga cgggaaggca caaagactt gaataatagc       4320
aaacggccag tagccaagac caaataatac tagagttaac tgatggtctt aaacaggcat      4380
tacgtggtga actccaagac caatatacaa aatatcgata agttattctt gcccaccaat     4440
ttaaggagcc tacatcagga cagtagtacc attcctcaga gaagaggtat acataacaag      4500
aaaatcgcgt gaacacctta tataacttag cccgttattg agctaaaaaa ccttgcaaaa      4560
tttcctatga ataagaatac ttcagacgtg ataaaaattt actttctaac tcttctcacg      4620
ctgcccctat ctgttcttcc gctctaccgt gagaaataaa gcatcgagta cggcagttcg      4680
ctgtcactga actaaaacaa taaggctagt tcgaatgatg aacttgcttg ctgtcaaact      4740
tctgagttgc cgctgatgtg acactgtgac aataaattca aaccggttat agcggtctcc      4800
tccggtaccg gttctgccac ctccaataga gctcagtagg agtcagaacc tctgcggtgg      4860
ctgtcagtga ctcatccgcg tttcgtaagt tgtgcgcgtg cacatttcgc ccgttcccgc      4920
tcatcttgca gcaggcggaa attttcatca cgctgtagga cgcaaaaaaa aataattaa       4980
tcgtacaaga atcttggaaa aaaaattgaa aaatttgta taaaagggat gacctaactt      5040
gactcaatgg cttttacacc cagtattttc cctttccttg tttgttacaa ttatagaagc      5100
aagacaaaaa catatagaca acctattcct aggagttata ttttttacc ctaccagcaa       5160
tataagtaaa aaactagtat gaaggtgttt tacgataaag actgcgatct gagcatcatc      5220
cagggaaaga aggttgctat tataggatat ggttcccaag gacacgcaca agccttgaac      5280
ttgaaagatt ctggggtcga cgtgacagta ggtctgtata aaggtgctgc tgatgcagca      5340
aaggctgaag cacatggctt taaagtcaca gatgttgcag cggctgttgc tggcgctgat      5400
ttagtcatga ttttaattcc agatgaattt caatcgcaat tgtacaaaaa tgaaatagaa      5460
ccaaacatta agaagggcgc taccttggcc ttcagtcatg gatttgccat tcattacaat      5520
caagtagtcc ccagggcaga tttggacgtt attatgattg cacctaaggc tccggggcat      5580
actgttagga gcgaatttgt taagggtggt ggtattccag atttgatcgc tatataccaa      5640
gacgttagcg gaaacgctaa gaatgtagct ttaagctacg cagcaggagt tggtggcggg      5700
agaacgggta taatagaaac cacttttaaa gacgagactg agacagattt atttggagaa      5760
caagcggttc tgtgcggagg aactgttgaa ttggttaaag caggctttga gacgcttgtc      5820
gaagcagggt acgctcccga aatggcatac ttcgaatgtc tacatgaatt gaagttgata      5880
gtagacttaa tgtatgaagg tggtatagct aatatgaact attccatttc aaataatgca      5940
gaatatggtg agtatgtcac cggacctgaa gtcattaacg cagaatcaag acaagccatg      6000
agaaatgcct tgaaacgtat ccaggacggt gaatacgcta agatgttcat aagtgaaggc      6060
gctacgggtt acccgagtat gactgctaaa agaagaaaca atgcagcaca tggtatcgaa      6120
attattggtg aacagttaag gtctatgatg ccctggatcg gtgctaataa gatcgtagac      6180
aaggcgaaaa attaaggccc tgcaggccta tcaagtgctg gaaactttt ctcttggaat       6240
ttttgcaaca tcaagtcata gtcaattgaa ttgacccaat ttcacattta agattttttt      6300
```

```
tttttcatcc gacatacatc tgtacactag gaagccctgt ttttctgaag cagcttcaaa    6360
tatatatatt ttttacatat ttattatgat tcaatgaaca atctaattaa atcgaaaaca    6420
agaaccgaaa cgcgaataaa taatttattt agatggtgac aagtgtataa gtcctcatcg    6480
ggacagctac gatttctctt tcggttttgg ctgagctact ggttgctgtg acgcagcggc    6540
attagcgcgg cgttatgagc taccctcgtg gcctgaaaga tggcgggaat aaagcggaac    6600
taaaaattac tgactgagcc atattgaggt caatttgtca actcgtcaag tcacgtttgg    6660
tggacggccc ctttccaacg aatcgtatat actaacatgc gcgcgcttcc tatatacaca    6720
tatacatata tatatatata tatgtgtg cgtgtatgtg tacacctgta tttaatttcc    6780
ttactcgcgg gtttttcttt tttctcaatt cttggcttcc tctttctcga gtatataatt    6840
tttcaggtaa aatttagtac gatagtaaaa tacttctcga actcgtcaca tatacgtgta    6900
cataatgtct gaaccagctc aaaagaaaca aaaggttgct aacaactctc tagagcggcc    6960
gcccgcaaat taaagccttc gagcgtccca aaaccttctc aagcaaggtt tcagtataa    7020 tgttacatgc gtacacgcgt ctgtacagaa aaaaagaaa aatttgaaat ataaataacg    7080
ttcttaatac taacataact ataaaaaaat aaatagggac ctagacttca ggttgtctaa    7140
ctccttcctt ttcggttaga gcggatgtgg ggggagggcg tgaatgtaag cgtgacataa    7200
ctaattacat gattaattaa ttattggttt tctggtctca actttctgac ttccttacca    7260
accttccaga tttccatgtt tctgatggtg tctaattcct tttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttcttcg acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
acgtaaccgg aaccaatggc aacggccaaa gcttgggcct tttcgtgagc cttaccggtg    7740
acatcgttcc agacgcgta agaagagtta ataccacgac cttccttgaa caaagatctg    7800
acagttctac cggaacccctt tggagcaacc aagataacat ctaagtcctt tggtggttca    7860
acgtgagtca agtccttgaa gactggggag aaaccgtggg agaagtacaa agtcttaccc    7920
ttggtcaaca atggcttgat agcaggccag gtttctgatt gagcggcatc ggacaacaag    7980
ttcataacgt aactacctct cttgatagca tcttcaacag tgaacaagtt cttgcctgga    8040
acccaaccgt cttcgatggc agccttccaa gaagcaccat ctttacggac accaatgata    8100
acgttcaaac cgttgtctct caagttcaaa ccttgaccgt aaccttggga accgtaaccg    8160
atcaaagcaa aagtgtcgtt cttgaagtag tccaacaact tttctcttgg ccagtcagct    8220
ctttcgtaga cggtttcaac agtaccaccg aagttgattt gcttcaacat cctcagctct    8280
agatttgaat atgtattact tggttatggt tatatatgac aaaagaaaaa gaagaacaga    8340
agaataacgc aaggaagaac aataactgaa attgatagag aagtattatg tctttgtctt    8400
tttataataa atcaagtgca gaaatccgtt agacaacatg agggataaaa tttaacgtgg    8460
gcgaagaaga aggaaaaaag ttttttgtgag ggcgtaattg aagcgatctg ttgattgtag    8520 atttttttt tttgaggagt caaagtcaga agagaacaga caaatggtat taaccatcca    8580
atactttttt ggagcaacgc taagctcatg cttttccatt ggttacgtgc tcagttgtta    8640
gatatggaaa gagaggatgc tcacggcagc gtgactccaa ttgagcccga aagagaggat    8700
```

```
gccacgtttt cccgacggct gctagaatgg aaaaaggaaa aatagaagaa tcccattcct    8760
atcattattt acgtaatgac ccacacattt ttgagatttt caactattac gtattacgat    8820
aatcctgctg tcattatcat tattatctat atcgacgtat gcaacgtatg tgaagccaag    8880
taggcaatta tttagtactg tcagtattgt tattcatttc agatctatcc gcggtggagc    8940
tcgaattcac tggccgtcgt tttacaacgt cgtgactggg aaaaccctgg cgttacccaa    9000
cttaatcgcc ttgcagcaca tccccctttc gccagctggc gtaatagcga agaggcccgc    9060
accgatcgcc cttcccaaca gttgcgcagc ctgaatggcg aatggcgcct gatgcggtat    9120
tttctcctta cgcatctgtg cggtatttca caccgcatac gtcaaagcaa ccatagtacg    9180
cgccctgtag cggcgcatta agcgcggcgg gtgtggtggt tacgcgcagc gtgaccgcta    9240
cacttgccag cgccttagcg cccgctcctt tcgctttctt cccttccttt ctcgccacgt    9300
tcgccggctt tccccgtcaa gctctaaatc gggggctccc tttagggttc cgatttagtg    9360
ctttacggca cctcgacccc aaaaaacttg atttgggtga tggttcacgt agtgggccat    9420
cgccctgata cggttttt cgcccttga cgttggagtc cacgttcttt aatagtggac    9480
tcttgttcca aactggaaca acactcaact ctatctcggg ctattctttt gatttataag    9540
ggattttgcc gatttcggtc tattggttaa aaaatgagct gatttaacaa aaatttaacg    9600
cgaattttaa caaaatatta acgtttacaa ttttatggtg cactctcagt acaatctgct    9660
ctgatgccgc atagttaagc cagccccgac acccgccaac acccgctgac gcgccctgac    9720
gggcttgtct gctcccggca tccgcttaca cagaagctgt gaccgtctcc gggagctgca    9780
tgtgtcagag gttttcaccg tcatcaccga aacgcgcgag acgaaagggc ctcgtgatac    9840
gcctattttt ataggttaat gtcatgataa taatggtttc ttagacgtca ggtggcactt    9900
ttcggggaaa tgtgcgcgga acccctattt gtttatttt ctaaatacat tcaaatatgt    9960
atccgctcat gagacaataa ccctgataaa tgcttcaata atattgaaaa aggaagagta   10020
tgagtattca acatttccgt gtcgccctta ttcccttttt tgcggcattt tgccttcctg   10080
tttttgctca cccagaaacg ctggtgaaag taaaagatgc tgaagatcag ttgggtgcac   10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac caccgatgc    10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
cactgattaa gcattggtaa ctgtcagacc aagtttactc atatatactt tagattgatt   10920
taaaacttca tttttaattt aaaaggatct aggtgaagat cctttttgat aatctcatga   10980
ccaaaatccc ttaacgtgag ttttcgttcc actgagcgtc agaccccgta gaaaagatca   11040
```

```
aaggatcttc ttgagatcct ttttttctgc gcgtaatctg ctgcttgcaa acaaaaaaac    11100
caccgctacc agcggtggtt tgtttgccgg atcaagagct accaactctt tttccgaagg    11160
taactggctt cagcagagcg cagataccaa atactgttct tctagtgtag ccgtagttag    11220
gccaccactt caagaactct gtagcaccgc ctacatacct cgctctgcta atcctgttac    11280
cagtggctgc tgccagtggc gataagtcgt gtcttaccgg gttggactca agacgatagt    11340
taccggataa ggcgcagcgg tcgggctgaa cggggggttc gtgcacacag cccagcttgg    11400
agcgaacgac ctacaccgaa ctgagatacc tacagcgtga gctatgagaa agcgccacgc    11460
ttcccgaagg gagaaaggcg gacaggtatc cggtaagcgg cagggtcgga acaggagagc    11520
gcacgaggga gcttccaggg ggaaacgcct ggtatcttta tagtcctgtc gggtttcgcc    11580
acctctgact tgagcgtcga ttttttgtgat gctcgtcagg ggggcggagc ctatggaaaa    11640
acgccagcaa cgcggccttt ttacggttcc tggccttttg ctggcctttt gctcacatgt    11700
tctttcctgc gttatcccct gattctgtgg ataaccgtat taccgccttt gagtgagctg    11760
ataccgctcg ccgcagccga acgaccgagc gcagcgagtc agtgagcgag gaagcggaag    11820
agcgcccaat acgcaaaccg cctctccccg cgcgttggcc gattcattaa tgcagctggc    11880
acgacaggtt tcccgactgg aaagcgggca gtgagcgcaa cgcaattaat gtgagttagc    11940
tcactcatta ggcacccccag gctttacact ttatgcttcc ggctcgtatg ttgtgtggaa    12000
ttgtgagcgg ataacaattt cacacaggaa acagctatga ccatgattac gccaagcttt    12060
ttctttccaa tttttttttt ttcgtcatta taaaaatcat tacgaccgag attcccgggt    12120
aataactgat ataattaaat tgaagctcta atttgtgagt ttagtataca tgcatttact    12180
tataatacag ttttttagtt ttgctggccg catcttctca aatatgcttc ccagcctgct    12240
tttctgtaac gttcaccctc taccttagca tcccttccct ttgcaaatag tcctcttcca    12300
acaataataa tgtcagatcc tgtagagacc acatcatcca cggttctata ctgttgaccc    12360
aatgcgtctc ccttgtcatc taaacccaca ccgggtgtca taatcaacca atcgtaacct    12420
tcatctcttc cacccatgtc tctttgagca ataaagccga taacaaaatc tttgtcgctc    12480
ttcgcaatgt caacagtacc cttagtatat tctccagtag atagggagcc cttgcatgac    12540
aattctgcta acatcaaaag gcctctaggt tcctttgtta cttcttctgc cgcctgcttc    12600
aaaccgctaa caatacctgg gcccaccaca ccgtgtgcat tcgtaatgtc tgcccattct    12660
gctattctgt atacacccgc agagtactgc aatttgactg tattaccaat gtcagcaaat    12720
tttctgtctt cgaagagtaa aaaattgtac ttggcggata atgcctttag cggcttaact    12780
gtgccctcca tggaaaaatc agtcaagata tccacatgtg ttttttagtaa acaaattttg    12840 ggacctaatg cttcaactaa ctccagtaat tccttggtgg tacgaacatc caatgaagca    12900
cacaagtttg tttgcttttc gtgcatgata ttaaatagct tggcagcaac aggactagga    12960
tgagtagcag cacgttcctt atatgtagct ttcgacatga tttatcttcg tttcctgcag    13020 gttttttgttc tgtgcagttg ggttaagaat actgggcaat ttcatgtttc ttcaacacta    13080
catatgcgta tatataccaa tctaagtctg tgctccttcc ttcgttcttc cttctgttcg    13140
gagattaccg aatcaaaaaa atttcaagga aaccgaaatc aaaaaaaaga ataaaaaaaa    13200
aatgatgaat tgaaaagctt gcatgcctgc aggtcgactc tagtatactc cgtctactgt    13260
acgatacact tccgctcagg tccttgtcct ttaacgaggc cttaccactc ttttgttact    13320
ctattgatcc agctcagcaa aggcagtgtg atctaagatt ctatcttcgc gatgtagtaa    13380
aactagctag accgagaaag agactagaaa tgcaaaaggc acttctacaa tggctgccat    13440
```

```
cattattatc cgatgtgacg ctgcattttt tttttttttt tttttttttt tttttttttt   13500
tttttttttt ttttttttgta caaatatcat aaaaaaagag aatctttta agcaaggatt   13560
ttcttaactt cttcggcgac agcatcaccg acttcggtgg tactgttgga accacctaaa   13620
tcaccagttc tgatacctgc atccaaaacc tttttaactg catcttcaat ggctttacct   13680
tcttcaggca agttcaatga caatttcaac atcattgcag cagacaagat agtggcgata   13740
gggttgacct tattctttgg caaatctgga gcggaaccat ggcatggttc gtacaaacca   13800
aatgcggtgt tcttgtctgg caaagaggcc aaggacgcag atggcaacaa acccaaggag   13860
cctgggataa cggaggcttc atcggagatg atatcaccaa acatgttgct ggtgattata   13920
ataccattta ggtgggttgg gttcttaact aggatcatgg cggcagaatc aatcaattga   13980
tgttgaactt tcaatgtagg gaattcgttc ttgatggttt cctccacagt ttttctccat   14040
aatcttgaag aggccaaaac attagcttta tccaaggacc aaataggcaa tggtggctca   14100
tgttgtaggg ccatgaaagc ggccattctt gtgattcttt gcacttctgg aacggtgtat   14160
tgttcactat cccaagcgac accatcacca tcgtcttcct ttctcttacc aaagtaaata   14220
cctcccacta attctctaac aacaacgaag tcagtacctt tagcaaattg tggcttgatt   14280
ggagataagt ctaaaagaga gtcggatgca aagttacatg gtcttaagtt ggcgtacaat   14340
tgaagttctt tacggatttt tagtaaacct tgttcaggtc taacactacc ggtaccccat   14400
ttaggaccac ccacagcacc taacaaaacg gcatcagcct tcttggaggc ttccagcgcc   14460
tcatctggaa gtggaacacc tgtagcatcg atagcagcac caccaattaa atgattttcg   14520
aaatcgaact tgacattgga acgaacatca gaaatagctt taagaacctt aatggcttcg   14580
gctgtgattt cttgaccaac gtggtcacct ggcaaaacga cgatcttctt aggggcagac   14640
attacaatgg tatatccttg aaatatatat aaaaaaaaaa aaaaaaaaaa aaaaaaaaaa   14700
tgcagcttct caatgatatt cgaatacgct tgaggagat acagcctaat atccgacaaa    14760
ctgttttaca gatttacgat cgtacttgtt acccatcatt gaattttgaa catccgaacc   14820
tgggagtttt ccctgaaaca gatagtatat ttgaacctgt ataataatat atagtctagc   14880
gctttacgga agacaatgta tgtatttcgg ttcctggaga aactattgca tctattgcat   14940
aggtaatctt gcacgtcgca tccccggttc attttctgcg tttccatctt gcacttcaat   15000
agcatatctt tgttaacgaa gcatctgtgc ttcattttgt agaacaaaaa tgcaacgcga   15060
gagcgctaat ttttcaaaca aagaatctga gctgcatttt tacagaacag aaatgcaacg   15120
cgaaagcgct attttaccaa cgaagaatct gtgcttcatt tttgtaaaac aaaaatgcaa   15180
cgcgagagcg ctaattttc aaacaaagaa tctgagctgc attttt acag aacagaaatg   15240
caacgcgaga gcgctatttt accaacaaag aatctatact tcttttttgt tctacaaaaa   15300
tgcatcccga gagcgctatt tttctaacaa agcatcttag attactttt ttctcctttg    15360
tgcgctctat aatgcagtct cttgataact ttttgcactg taggtccgtt aaggttagaa   15420
gaaggctact ttggtgtcta ttttctcttc cataaaaaaa gcctgactcc acttcccgcg   15480
tttactgatt actagcgaag ctgcgggtgc attttttcaa gataaaggca tccccgatta   15540
tattctatac cgatgtggat tgcgcatact tgtgaacag aaagtgatag cgttgatgat    15600
tcttcattgg tcagaaaatt atgaacggtt tcttctattt tgtctctata tactacgtat   15660
aggaaatgtt tacattttcg tattgttttc gattcactct atgaatagtt cttactacaa   15720
ttttttttgtc taaagagtaa tactagagat aaacataaaa aatgtagagg tcgagtttag   15780
```

| | |
|---|---|
| atgcaagttc aaggagcgaa aggtggatgg gtaggttata tagggatata gcacagagat | 15840 |
| atatagcaaa gagatacttt tgagcaatgt ttgtggaagc ggtattcgca atattttagt | 15900 |
| agctcgttac agtccggtgc gttttttggtt ttttgaaagt gcgtcttcag agcgcttttg | 15960 |
| gttttcaaaa gcgctctgaa gttcctatac tttctagaga ataggaactt cggaatagga | 16020 |
| acttcaaagc gtttccgaaa acgagcgctt ccgaaaatgc aacgcgagct gcgcacatac | 16080 |
| agctcactgt tcacgtcgca cctatatctg cgtgttgcct gtatatatat atacatgaga | 16140 |
| agaacggcat agtgcgtgtt tatgcttaaa tgcgtactta tatgcgtcta tttatgtagg | 16200 |
| atgaaaggta gtctagtacc tcctgtgata ttatcccatt ccatgcgggg tatcgtatgc | 16260 |
| ttccttcagc actacccttt agctgttcta tatgctgcca ctcctcaatt ggattagtct | 16320 |
| catccttcaa tgctatcatt tccctttgata ttggatcata tgcatagtac cgagaaacta | 16380 |
| gaggatc | 16387 |

<210> SEQ ID NO 49
<211> LENGTH: 448
<212> TYPE: DNA
<213> ORGANISM: Saccharomyces cerevisiae

<400> SEQUENCE: 49

| | |
|---|---|
| cccattaccg acatttgggc gctatacgtg catatgttca tgtatgtatc tgtatttaaa | 60 |
| acacttttgt attattttttc ctcatatatg tgtataggtt tatacggatg atttaattat | 120 |
| tacttcacca ccctttattt caggctgata tcttagcctt gttactagtt agaaaaagac | 180 |
| attttttgctg tcagtcactg tcaagagatt cttttgctgg catttcttct agaagcaaaa | 240 |
| agagcgatgc gtcttttccg ctgaaccgtt ccagcaaaaa agactaccaa cgcaatatgg | 300 |
| attgtcagaa tcatataaaa gagaagcaaa taactccttg tcttgtatca attgcattat | 360 |
| aatatcttct tgttagtgca atatcatata gaagtcatcg aaatagatat taagaaaaac | 420 |
| aaactgtaca atcaatcaat caatcatc | 448 |

<210> SEQ ID NO 50
<211> LENGTH: 250
<212> TYPE: DNA
<213> ORGANISM: Saccharomyces cerevisiae

<400> SEQUENCE: 50

| | |
|---|---|
| ccgcaaatta aagccttcga gcgtcccaaa accttctcaa gcaaggtttt cagtataatg | 60 |
| ttacatgcgt acacgcgtct gtacagaaaa aaagaaaaa tttgaaatat aaataacgtt | 120 |
| cttaatacta acataactat aaaaaaataa atagggacct agacttcagg ttgtctaact | 180 |
| ccttcctttt cggttagagc ggatgtgggg ggagggcgtg aatgtaagcg tgacataact | 240 |
| aattacatga | 250 |

<210> SEQ ID NO 51
<211> LENGTH: 1181
<212> TYPE: DNA
<213> ORGANISM: Saccharomyces cerevisiae

<400> SEQUENCE: 51

| | |
|---|---|
| taaaacctct agtggagtag tagatgtaat caatgaagcg gaagccaaaa gaccagagta | 60 |
| gaggcctata gaagaaactg cgataccttt tgtgatggct aaacaaacag acatcttttt | 120 |
| atatgttttt acttctgtat atcgtgaagt agtaagtgat aagcgaattt ggctaagaac | 180 |
| gttgtaagtg aacaagggac ctcttttgcc tttcaaaaaa ggattaaatg gagttaatca | 240 |

```
ttgagattta gttttcgtta gattctgtat ccctaaataa ctcccttacc cgacgggaag    300
gcacaaaaga cttgaataat agcaaacggc cagtagccaa gaccaaataa tactagagtt    360
aactgatggt cttaaacagg cattacgtgg tgaactccaa gaccaatata caaaatatcg    420
ataagttatt cttgcccacc aatttaagga gcctacatca ggacagtagt accattcctc    480
agagaagagg tatacataac aagaaaatcg cgtgaacacc ttatataact tagcccgtta    540
ttgagctaaa aaaccttgca aaatttccta tgaataagaa tacttcagac gtgataaaaa    600
tttactttct aactcttctc acgctgcccc tatctgttct tccgctctac cgtgagaaat    660
aaagcatcga gtacggcagt tcgctgtcac tgaactaaaa caataaggct agttcgaatg    720
atgaacttgc ttgctgtcaa acttctgagt tgccgctgat gtgacactgt gacaataaat    780
tcaaaccggt tatagcggtc tcctccggta ccggttctgc cacctccaat agagctcagt    840
aggagtcaga acctctgcgg tggctgtcag tgactcatcc gcgtttcgta agttgtgcgc    900
gtgcacattt cgcccgttcc cgctcatctt gcagcaggcg gaaattttca tcacgctgta    960
ggacgcaaaa aaaaaataat taatcgtaca agaatcttgg aaaaaaaatt gaaaaatttt   1020
gtataaaagg gatgacctaa cttgactcaa tggcttttac acccagtatt ttccctttcc   1080
ttgtttgtta caattataga agcaagacaa aaacatatag acaacctatt cctaggagtt   1140
atattttttt accctaccag caatataagt aaaaaactag t                       1181

<210> SEQ ID NO 52
<211> LENGTH: 759
<212> TYPE: DNA
<213> ORGANISM: Saccharomyces cerevisiae

<400> SEQUENCE: 52
ggccctgcag gcctatcaag tgctggaaac tttttctctt ggaattttg caacatcaag      60 tcatagtcaa ttgaattgac ccaatttcac atttaagatt ttttttttt catccgacat    120 acatctgtac actaggaagc cctgtttttc tgaagcagct tcaaatatat atatttttta    180
catatttatt atgattcaat gaacaatcta attaaatcga aaacaagaac cgaaacgcga    240
ataaataatt tatttagatg gtgacaagtg tataagtcct catcgggaca gctacgattt    300
ctctttcggt tttggctgag ctactggttg ctgtgacgca gcggcattag cgcggcgtta    360
tgagctaccc tcgtggcctg aaagatggcg ggaataaagc ggaactaaaa attactgact    420
gagccatatt gaggtcaatt tgtcaactcg tcaagtcacg tttggtggac ggccccttc    480 caacgaatcg tatatactaa catgcgcgcg cttcctatat acacatatac atatatatat    540
atatatatat gtgtgcgtgt atgtgtacac ctgtatttaa tttccttact cgcgggtttt    600
tcttttttct caattcttgg cttcctcttt ctcgagtata taatttttca ggtaaaattt    660
agtacgatag taaaatactt ctcgaactcg tcacatatac gtgtacataa tgtctgaacc    720
agctcaaaag aaacaaaagg ttgctaacaa ctctctaga                           759

<210> SEQ ID NO 53
<211> LENGTH: 643
<212> TYPE: DNA
<213> ORGANISM: Saccharomyces cerevisiae

<400> SEQUENCE: 53
gaaatgaata acaatactga cagtactaaa taattgccta cttggcttca catacgttgc     60
atacgtcgat atagataata atgataatga cagcaggatt atcgtaatac gtaatagttg    120
```

|  |  |
|---|---|
| aaaatctcaa aaatgtgtgg gtcattacgt aaataatgat aggaatggga ttcttctatt | 180 |
| tttccttttt ccattctagc agccgtcggg aaaacgtggc atcctctctt tcgggctcaa | 240 |
| ttggagtcac gctgccgtga gcatcctctc tttccatatc taacaactga gcacgtaacc | 300 |
| aatggaaaag catgagctta gcgttgctcc aaaaaagtat tggatggtta ataccatttg | 360 |
| tctgttctct tctgactttg actcctcaaa aaaaaaaaat ctacaatcaa cagatcgctt | 420 |
| caattacgcc ctcacaaaaa ctttttttcct tcttcttcgc ccacgttaaa ttttatccct | 480 |
| catgttgtct aacggatttc tgcacttgat ttattataaa aagacaaaga cataatactt | 540 |
| ctctatcaat ttcagttatt gttcttcctt gcgttattct tctgttcttc ttttctttt | 600 |
| gtcatatata accataacca agtaatacat attcaaatct aga | 643 |

<210> SEQ ID NO 54
<211> LENGTH: 270
<212> TYPE: DNA
<213> ORGANISM: Saccharomyces cerevisiae

<400> SEQUENCE: 54

|  |  |
|---|---|
| gacctcgagt catgtaatta gttatgtcac gcttacattc acgccctccc cccacatccg | 60 |
| ctctaaccga aaaggaagga gttagacaac ctgaagtcta ggtccctatt tatttttta | 120 |
| tagttatgtt agtattaaga acgttattta tatttcaaat ttttcttttt tttctgtaca | 180 |
| gacgcgtgta cgcatgtaac attatactga aaaccttgct tgagaaggtt ttgggacgct | 240 |
| cgaaggcttt aatttgcggc cggtacccaa | 270 |

<210> SEQ ID NO 55
<211> LENGTH: 15539
<212> TYPE: DNA
<213> ORGANISM: artificial sequence
<220> FEATURE:
<223> OTHER INFORMATION: constructed plasmid

<400> SEQUENCE: 55

|  |  |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tcttttttcta | 300 |
| ttactcttgg cctcctctag tacactctat attttttat gcctcggtaa tgattttcat | 360 |
| ttttttttt ccacctagcg gatgactctt ttttttttctt agcgattggc attatcacat | 420 |
| aatgaattat acattatata aagtaatgtg atttcttcga agaatatact aaaaaatgag | 480 |
| caggcaagat aaacgaaggc aaagatgaca gagcagaaag ccctagtaaa gcgtattaca | 540 |
| aatgaaacca agattcagat tgcgatctct ttaaagggtg gtcccctagc gatagagcac | 600 |
| tcgatcttcc cagaaaaaga ggcagaagca gtagcagaac aggccacaca atcgcaagtg | 660 |
| attaacgtcc acacaggtat agggtttctg gaccatatga tacatgctct ggccaagcat | 720 |
| tccggctggt cgctaatcgt tgagtgcatt ggtgacttac acatagacga ccatcacacc | 780 |
| actgaagact gcgggattgc tctcggtcaa gcttttaaag aggccctagg ggccgtgcgt | 840 |
| ggagtaaaaa ggtttggatc aggatttgcg ccttttggatg aggcactttc cagagcggtg | 900 |
| gtagatcttt cgaacaggcc gtacgcagtt gtcgaacttg gtttgcaaag ggagaaagta | 960 |
| ggagatctct cttgcgagat gatcccgcat tttcttgaaa gctttgcaga ggctagcaga | 1020 |

```
attaccctcc acgttgattg tctgcgaggc aagaatgatc atcaccgtag tgagagtgcg    1080
ttcaaggctc ttgcggttgc cataagagaa gccacctcgc ccaatggtac caacgatgtt    1140
ccctccacca aaggtgttct tatgtagtga caccgattat ttaaagctgc agcatacgat    1200
atatatacat gtgtatatat gtatacctat gaatgtcagt aagtatgtat acgaacagta    1260
tgatactgaa gatgacaagg taatgcatca ttctatacgt gtcattctga acgaggcgcg    1320
cttttccttt ttcttttgc ttttttcttt ttttctctt gaactcgacg gatctatgcg     1380
gtgtgaaata ccgcacagat gcgtaaggag aaaataccgc atcaggaaat tgtaagcgtt    1440
aatattttgt taaaattcgc gttaaatttt tgttaaatca gctcattttt taaccaatag    1500
gccgaaatcg gcaaaatccc ttataaatca aagaataga ccgagatagg gttgagtgtt     1560
gttccagttt ggaacaagag tccactatta agaacgtgg actccaacgt caagggcga      1620
aaaaccgtct atcagggcga tggcccacta cgtgaaccat caccctaatc aagttttttg    1680
gggtcgaggt gccgtaaagc actaaatcgg aaccctaaag ggagccccg atttagagct     1740
tgacggggaa agccggcgaa cgtggcgaga aggaaggga agaaagcgaa aggagcgggc     1800
gctagggcgc tggcaagtgt agcggtcacg ctgcgcgtaa ccaccacacc cgccgcgctt    1860
aatgcgccgc tacagggcgc gtccattcgc cattcaggct gcgcaactgt tgggaagggc    1920
gcggtgcggg cctcttcgct attacgccag ctggcgaaag ggggatgtgc tgcaaggcga    1980
ttaagttggg taacgccagg gttttcccag tcacgacgtt gtaaaacgac ggccagtgag    2040
cgcgcgtaat acgactcact ataggggcgaa ttgggtaccg gccccccct cgaggtcgac    2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tccttcccc    2400
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttccttt tccattctag cagccgtcgg gaaaacgtgg catcctctct     2700
ttcgggctca attggagtca cgctgccgtg agcatcctct ctttccatat ctaacaactg    2760
agcacgtaac caatggaaaa gcatgagctt agcgttgctc caaaaaagta ttggatggtt    2820
aataccattt gtctgttctc ttctgacttt gactcctcaa aaaaaaaaat ctacaatcaa    2880
cagatcgctt caattacgcc ctcacaaaaa cttttttcct tcttcttcgc ccacgttaaa    2940
ttttatccct catgttgtct aacggattc tgcacttgat ttattataaa aagacaaaga    3000
cataatactt ctctatcaat ttcagttatt gttcttcctt gcgttattct tctgttcttc    3060
tttttctttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300
tggtaaaacta gccaaagtcg gtgttaagga agctggtgct tggccagttc agttcggaac    3360
```

```
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccattttg cttacggcgg aacaattgca cctggtaatt tagacggcaa     3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct cacccggctg aatccgcaga aagaaagca gatattgaag aagctggtcg     3840
cgctgttgtc aaaatgctcg aaatgggctt aaaaccttct gacattttaa cgcgtgaagc    3900
ttttgaagat gctattactg taactatggc tctgggaggt tcaaccaact caaccccttca   3960 cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa aacagtcgct gaaaatttga aggcttttga    4200
tgatttaaca cctggtcaaa aggttattat gccgcttgaa aatcctaaac gtgaagatgg    4260
tccgctcatt attctccatg gtaacttggc tccagacggt gccgttgcca agtttctgg     4320 tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttcccct tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaaatgttg tcctggttgc tgtggttaag cggccgcgtt    4860
aattcaaatt aattgatata gttttttaat gagtattgaa tctgtttaga aataatggaa    4920
tattattttt atttatttat ttatattatt ggtcggctct tttcttctga aggtcaatga    4980
caaaatgata tgaaggaaat aatgatttct aaaattttac aacgtaagat attttttacaa   5040 aagcctagct catcttttgt catgcactat tttactcacg cttgaaatta acggccagtc    5100
cactgcggag tcatttcaaa gtcatcctaa tcgatctatc gttttttgata gctcattttg    5160 gagttcgcga ttgtcttctg ttattcacaa ctgttttaat ttttatttca ttctggaact    5220
cttcgagttc tttgtaaagt cttttcatagt agcttacttt atcctccaac atatttaact   5280
tcatgtcaat ttcggctctt aaattttcca catcatcaag ttcaacatca tctttttaact  5340 tgaatttatt ctctagctct tccaaccaag cctcattgct ccttgattta ctggtgaaaa    5400
gtgatacact ttgcgcgcaa tccaggtcaa actttcctg caaagaattc accaatttct     5460
cgacatcata gtacaatttg ttttgttctc ccatcacaat ttaatatacc tgatggattc    5520
ttatgaagcg ctgggtaatg gacgtgtcac tctacttcgc ctttttccct actccttta    5580 gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760
```

```
tgattttttga tattgtataa aaaaaccaaa tatgtataaa aaaagtgaat aaaaaatacc    5820
aagtatggag aaatatatta gaagtctata cgttaaacca cccgggcccc ccctcgaggt    5880
cgacggtatc gataagcttg atatcgaatt cctgcagccc ggggatcca ctagttctag     5940 agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat tttttttata acttatttaa    6240
taataaaaat cataaatcat aagaaattcg cttactctta attaatcaaa aagttaaaat    6300
tgtacgaata gattcaccac ttcttaacaa atcaaacccct tcattgattt tctcgaatgg   6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga atcaactcc accgtttgac atttcagtaa ggacttcttg     6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440 tttgttttgga ttattaagaa gaataattac aaaaaaaatt acaaaggaag gtaattacaa   7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
```

```
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagatttta    8640
catttctggt gttgaaggga agatatgag ctatacagcg gaatttccat atcactcaga    8700
ttttgttatc taatttttc cttcccacgt ccgcgggaat ctgtgtatat tactgcatct    8760
agatatatgt tatcttatct tggcgcgtac atttaatttt caacgtattc tataagaaat    8820
tgcgggagtt tttttcatgt agatgatact gactgcacgc aaatataggc atgatttata    8880
ggcatgattt gatggctgta ccgataggaa cgctaagagt aacttcagaa tcgttatcct    8940
ggcggaaaaa attcatttgt aaactttaaa aaaaaaagcc aatatcccca aaattattaa    9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc    9240
tgcaggcctc agctcttgtt ttgttctgca ataacttac ccatcttttt caaaacttta    9300
ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca agtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaatttttcc ttcttaagag gcaaggatgg ttttcagcc   10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
```

```
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttc gttcttgcgt acccgtcggc catataggag    10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca atacctaccg tctttatata   11040
cttattagtc aagtagggga ataatttcag ggaactggtt tcaaccttt tttttcagctt   11100 tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt tttttgcctg tttgtgcccc tgttctctgt agttgcgcta agagaatgga   11280
cctatgaact gatggttggt gaagaaaaca atattttggt gctgggattc ttttttttc    11340 tggatgccag cttaaaaagc gggctccatt atatttagtg gatgccagga ataaactgtt   11400
cacccagaca cctacgatgt tatatattct gtgtaacccg ccccctattt tgggcatgta   11460
cgggttacag cagaattaaa aggctaattt tttgactaaa taaagttagg aaaatcacta   11520
ctattaatta tttacgtatt ctttgaaatg gcagtattga taatgataaa ctcgaactga   11580
aaaagcgtgt tttttattca aaatgattct aactcccta cgtaatcaag gatctttttt    11640
gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt ttgttccctt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
ttgcgtattg ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgcccccctg acgagcatca caaaaatcga   12420
cgctcaagtc agaggtggcg aaacccgaca ggactataaa gataccaggc gtttccccct   12480
ggaagctccc tcgtgcgctc tcctgttccg accctgccgc ttaccggata cctgtccgcc   12540
tttctccctt cgggaagcgt ggcgctttct catagctcac gctgtaggta tctcagttcg   12600
gtgtaggtcg ttcgctccaa gctgggctgt gtgcacgaac cccccgttca gcccgaccgc   12660
tgcgccttat ccggtaacta tcgtcttgag tccaacccgg taagacacga cttatcgcca   12720
ctggcagcag ccactggtaa caggattagc agagcgaggt atgtaggcgg tgctacagag   12780
ttcttgaagt ggtggcctaa ctacggctac actagaagaa cagtatttgg tatctgcgct   12840
```

```
ctgctgaagc cagttacctt cggaaaaaga gttggtagct cttgatccgg caaacaaacc    12900
accgctggta gcggtggttt ttttgtttgc aagcagcaga ttacgcgcag aaaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
taaaaatgaa gttttaaatc aatctaaagt atatatgagt aaacttggtc tgacagttac    13140
caatgcttaa tcagtgaggc acctatctca gcgatctgtc tatttcgttc atccatagtt    13200
gcctgactcc ccgtcgtgta gataactacg atacgggagg cttaccatc tggccccagt    13260 gctgcaatga taccgcgaga cccacgctca ccggctccag atttatcagc aataaaccag    13320
ccagccggaa gggccgagcg cagaagtggt cctgcaactt tatccgcctc catccagtct    13380
attaattgtt gccgggaagc tagagtaagt agttcgccag ttaatagttt gcgcaacgtt    13440
gttgccattg ctacaggcat cgtggtgtca cgctcgtcgt ttggtatggc ttcattcagc    13500
tccggttccc aacgatcaag gcgagttaca tgatccccca tgttgtgcaa aaaagcggtt    13560
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga gaatagtgta gcggcgacc gagttgctct    13740 tgcccggcgt caatacggga taataccgcg ccacatagca gaactttaaa agtgctcatc    13800
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttcctttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taattttttca acaaagaat ctgagctgca ttttttacaga    14220 acagaaatgc aacgcgaaag cgctatttta ccaacgaaga atctgtgctt catttttgta    14280
aaacaaaaat gcaacgcgag agcgctaatt tttcaaacaa agaatctgag ctgcattttt    14340
acagaacaga aatgcaacgc gagagcgcta ttttaccaac aaagaatcta tacttctttt    14400
ttgttctaca aaaatgcatc ccgagagcgc tattttcta acaaagcatc ttagattact    14460 tttttctcc tttgtgcgct ctataatgca gtctcttgat aacttttgc actgtaggtc    14520 cgttaaggtt agaagaaggc tactttggtg tctattttct cttccataaa aaagcctga    14580 ctccacttcc cgcgtttact gattactagc gaagctgcgg gtgcattttt tcaagataaa    14640
ggcatccccg attatattct ataccgatgt ggattgcgca tactttgtga acagaaagtg    14700
atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaattttt tgtctaaaga gtaaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggttttttga aagtgcgtct    15060
tcagagcgct tttggttttc aaaagcgctc tgaagttcct atactttcta gagaatagga    15120
acttcggaat aggaacttca aagcgtttcc gaaacgagc gcttccgaaa atgcaacgcg    15180
agctgcgcac atacagctca ctgttcacgt cgcacctata tctgcgtgtt gcctgtatat    15240
```

```
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc     15539

<210> SEQ ID NO 56
<211> LENGTH: 1125
<212> TYPE: DNA
<213> ORGANISM: artificial sequence
<220> FEATURE:
<223> OTHER INFORMATION: horse ADH coding region codon optimized for S.
      cerevisiae expression

<400> SEQUENCE: 56
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcc ttgaatccat aggtgaaggt     240
gttaccactg ttcgtcctgg tgataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
ttccttggta cttctacatt tccccaatac acagtggtgg acgagatatc tgtcgctaaa     480
atcgatgcag cttcaccact ggaaaaagtt tgcttgatag ggtgcggatt ttccaccggt     540
tacggttccg cagttaaagt tgcaaaggtt acacagggtt cgacttgtgc agtattcggt     600
ttaggaggag taggactaag cgttattatg gggtgtaaag ctgcaggcgc agcgaggatt     660
ataggtgtag acatcaataa ggacaaattt gcaaaagcta aggaggtcgg ggctactgaa     720
tgtgttaacc ctcaagatta taagaaacca atacaagaag tccttactga aatgtcaaac     780
ggtggagttg atttctcttt tgaagttata ggccgtcttg atactatggt aactgcgttg     840
tcctgctgtc aagaggcata tggagtcagt gtgatcgtag gtgttcctcc tgattcacaa     900
aatttgtcga tgaatcctat gctgttgcta agcggtcgta catggaaggg agctatattt     960
ggcggtttta gagcaagga tagtgttcca aaacttgttg ccgactttat ggcgaagaag    1020
tttgctcttg atcctttaat tacacatgta ttgccattcg agaaaatcaa tgaagggttt    1080
gatttgttaa gaagtggtga atctattcgt acaattttaa ctttt                   1125

<210> SEQ ID NO 57
<211> LENGTH: 375
<212> TYPE: PRT
<213> ORGANISM: Equus caballus

<400> SEQUENCE: 57

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60
```

| | | | | | | | | | | | | | | | |
|---|---|---|---|---|---|---|---|---|---|---|---|---|---|---|---|
| Ile | Ala | Gly | His | Glu | Ala | Ala | Gly | Ile | Val | Glu | Ser | Ile | Gly | Glu | Gly |
| 65 | | | | 70 | | | | | 75 | | | | | 80 | |
| Val | Thr | Thr | Val | Arg | Pro | Gly | Asp | Lys | Val | Ile | Pro | Leu | Phe | Thr | Pro |
| | | | | 85 | | | | | 90 | | | | | 95 | |
| Gln | Cys | Gly | Lys | Cys | Arg | Val | Cys | Lys | His | Pro | Glu | Gly | Asn | Phe | Cys |
| | | | 100 | | | | | 105 | | | | | 110 | | |
| Leu | Lys | Asn | Asp | Leu | Ser | Met | Pro | Arg | Gly | Thr | Met | Gln | Asp | Gly | Thr |
| | | | 115 | | | | | 120 | | | | | 125 | | |
| Ser | Arg | Phe | Thr | Cys | Arg | Gly | Lys | Pro | Ile | His | His | Phe | Leu | Gly | Thr |
| | 130 | | | | | 135 | | | | | 140 | | | | |
| Ser | Thr | Phe | Ser | Gln | Tyr | Thr | Val | Val | Asp | Glu | Ile | Ser | Val | Ala | Lys |
| 145 | | | | | 150 | | | | | 155 | | | | | 160 |
| Ile | Asp | Ala | Ala | Ser | Pro | Leu | Glu | Lys | Val | Cys | Leu | Ile | Gly | Cys | Gly |
| | | | | 165 | | | | | 170 | | | | | 175 | |
| Phe | Ser | Thr | Gly | Tyr | Gly | Ser | Ala | Val | Lys | Val | Ala | Lys | Val | Thr | Gln |
| | | | 180 | | | | | 185 | | | | | 190 | | |
| Gly | Ser | Thr | Cys | Ala | Val | Phe | Gly | Leu | Gly | Val | Gly | Leu | Ser | Val |
| | | 195 | | | | | 200 | | | | | 205 | | | |
| Ile | Met | Gly | Cys | Lys | Ala | Ala | Gly | Ala | Ala | Arg | Ile | Ile | Gly | Val | Asp |
| | 210 | | | | | 215 | | | | | 220 | | | | |
| Ile | Asn | Lys | Asp | Lys | Phe | Ala | Lys | Ala | Lys | Glu | Val | Gly | Ala | Thr | Glu |
| 225 | | | | | 230 | | | | | 235 | | | | | 240 |
| Cys | Val | Asn | Pro | Gln | Asp | Tyr | Lys | Lys | Pro | Ile | Gln | Glu | Val | Leu | Thr |
| | | | | 245 | | | | | 250 | | | | | 255 | |
| Glu | Met | Ser | Asn | Gly | Gly | Val | Asp | Phe | Ser | Phe | Glu | Val | Ile | Gly | Arg |
| | | | 260 | | | | | 265 | | | | | 270 | | |
| Leu | Asp | Thr | Met | Val | Thr | Ala | Leu | Ser | Cys | Cys | Gln | Glu | Ala | Tyr | Gly |
| | | 275 | | | | | 280 | | | | | 285 | | | |
| Val | Ser | Val | Ile | Val | Gly | Val | Pro | Pro | Asp | Ser | Gln | Asn | Leu | Ser | Met |
| | 290 | | | | | 295 | | | | | 300 | | | | |
| Asn | Pro | Met | Leu | Leu | Leu | Ser | Gly | Arg | Thr | Trp | Lys | Gly | Ala | Ile | Phe |
| 305 | | | | | 310 | | | | | 315 | | | | | 320 |
| Gly | Gly | Phe | Lys | Ser | Lys | Asp | Ser | Val | Pro | Lys | Leu | Val | Ala | Asp | Phe |
| | | | | 325 | | | | | 330 | | | | | 335 | |
| Met | Ala | Lys | Lys | Phe | Ala | Leu | Asp | Pro | Leu | Ile | Thr | His | Val | Leu | Pro |
| | | | 340 | | | | | 345 | | | | | 350 | | |
| Phe | Glu | Lys | Ile | Asn | Glu | Gly | Phe | Asp | Leu | Leu | Arg | Ser | Gly | Glu | Ser |
| | | | 355 | | | | | 360 | | | | | 365 | | |
| Ile | Arg | Thr | Ile | Leu | Thr | Phe | | | | | | | | | |
| | 370 | | | | | 375 | | | | | | | | | |

<210> SEQ ID NO 58
<211> LENGTH: 9089
<212> TYPE: DNA
<213> ORGANISM: artificial sequence
<220> FEATURE:
<223> OTHER INFORMATION: constructed plasmid

<400> SEQUENCE: 58

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataccac agcttttcaa ttcaattcat cattttttt ttattctttt ttttgatttc | 240 |

```
ggtttctttg aaattttttt gattcggtaa tctccgaaca gaaggaagaa cgaaggaagg      300
agcacagact tagattggta tatatacgca tatgtagtgt tgaagaaaca tgaaattgcc      360
cagtattctt aacccaactg cacagaacaa aaacctgcag gaaacgaaga taaatcatgt      420
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat ttgtttacta aaaacacatg      600
tggatatctt gactgatttt tccatggagg gcacagttaa gccgctaaag gcattatccg      660
ccaagtacaa tttttttactc ttcgaagaca gaaaatttgc tgacattggt aatacagtca      720
aattgcagta ctctgcgggt gtatacagaa tagcagaatg ggcagacatt acgaatgcac      780
acggtgtggt gggcccaggt attgttagcg gtttgaagca ggcggcagaa gaagtaacaa      840
aggaacctag aggccttttg atgttagcag aattgtcatg caagggctcc ctatctactg      900
gagaatatac taagggtact gttgacattg cgaagagcga caaagatttt gttatcggct      960
ttattgctca aagagacatg ggtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttggaag aggactattt gcaaagggaa     1140
gggatgctaa ggtagagggt gaacgttaca gaaaagcagg ctgggaagca tatttgagaa     1200
gatgcggcca gcaaaactaa aaaactgtat tataagtaaa tgcatgtata ctaaactcac     1260
aaattagagc ttcaatttaa ttatatcagt tattacccta tgcggtgtga aataccgcac     1320
agatgcgtaa ggagaaaata ccgcatcagg aaattgtaaa cgttaatatt ttgttaaaat     1380
tcgcgttaaa ttttttgttaa atcagctcat tttttaacca ataggccgaa atcggcaaaa     1440
tcccttataa atcaaaagaa tagaccgaga tagggttgag tgttgttcca gtttggaaca     1500
agagtccact attaaagaac gtggactcca acgtcaaagg gcgaaaaacc gtctatcagg     1560
gcgatggccc actacgtgaa ccatcaccct aatcaagttt ttggggtcg aggtgccgta     1620 aagcactaaa tcggaaccct aaagggagcc ccgatttag agcttgacgg ggaaagccgg     1680
cgaacgtggc gagaaaggaa gggaagaaag cgaaaggagc gggcgctagg gcgctggcaa     1740
gtgtagcggt cacgctgcgc gtaaccacca cacccgccgc gcttaatgcg ccgctacagg     1800
gcgcgtcgcg ccattcgcca ttcaggctgc gcaactgttg ggaagggcga tcggtgcggg     1860
cctcttcgct attacgccag ctggcgaaag ggggatgtgc tgcaaggcga ttaagttggg     1920
taacgccagg gttttcccag tcacgacgtt gtaaaacgac ggccagtgag cgcgcgtaat     1980
acgactcact atagggcgaa ttgggtaccg gccccccct cgaggtcgac tggccattaa     2040
tctttcccat attagatttc gccaagccat gaaagttcaa gaaaggtctt tagacgaatt     2100
acccttcatt tctcaaactg gcgtcaaggg atcctggtat ggttttatcg ttttatttct     2160
ggttcttata gcatcgtttt ggacttctct gttcccatta gcggttcag gagccagcgc     2220 agaatcattc tttgaaggat acttatcctt tccaattttg attgtctgtt acgttggaca     2280
taaactgtat actagaaatt ggactttgat ggtgaaacta aagatatgg atcttgatac     2340 cggcagaaaa caagtagatt tgactcttcg tagggaagaa atgaggattg agcgagaaac     2400
attagcaaaa agatccttcg taacaagatt tttacatttc tggtgttgaa gggaaagata     2460
tgagctatac agcggaattt ccatatcact cagatttgt tatctaattt tttccttccc     2520
acgtccgcgg gaatctgtgt atattactgc atctagatat atgttatctt atcttggcgc     2580
gtacatttaa ttttcaacgt attctataag aaattgcggg agtttttttc atgtagatga     2640
```

```
tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaagaa    2880
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctgtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tctttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg gtttttacca tacccgggcc    3780
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca ctttttggcg catgggtgac cattaaatac    3960
aactgcattc cccgcagcta tcatacctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acattttcaa atactccaaa acatgaagag ttatctttgt aattctttaa    4380
gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca atacctaccg tctttatata cttattagtc aagtagggga ataatttcag    4620
ggaactggtt tcaaccttttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc    4800 tgttctctgt agttgcgcta agagaatgga cctatgaact gatggttggt gaagaaaaca    4860 atatttggt gctgggattc ttttttttc tggatgccag cttaaaaagc gggctccatt    4920
atatttagtg gatgccagga ataaactgtt cacccagaca cctacgatgt tatatattct    4980
```

```
gtgtaacccg cccctattt tgggcatgta cgggttacag cagaattaaa aggctaattt    5040
tttgactaaa taaagttagg aaaatcacta ctattaatta tttacgtatt ctttgaaatg   5100
gcagtattga taatgataaa ctcgaactga aaaagcgtgt ttttattca aaatgattct    5160
aactcccttta cgtaatcaag gaatcttttt gccttggcct ccgcgtcatt aaacttcttg  5220
ttgttgacgc taacattcaa cgctagtata tattcgtttt tttcaggtaa gttctttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat  5400
ttaaatcttg gctctcttgg gctcaaggtg acaaggtcct cgaaaatagg gcgcgcccca  5460
ccgcggtgga gctccagctt tgttcccctt tagtgagggt taattgcgcg cttggcgtaa  5520
tcatggtcat agctgtttcc tgtgtgaaat tgttatccgc tcacaattcc acacaacata  5580
ggagccggaa gcataaagtg taaagcctgg ggtgcctaat gagtgaggta actcacatta  5640
attgcgttgc gctcactgcc cgcttttcca tcgggaaacc tgtcgtgcca gctgcattaa  5700
tgaatcggcc aacgcgcggg gagaggcggt ttgcgtattg ggcgctcttc cgcttcctcg  5760
ctcactgact cgctgcgctc ggtcgttcgg ctgcggcgag cggtatcagc tcactcaaag  5820
gcggtaatac ggttatccac agaatcaggg gataacgcag gaaagaacat gtgagcaaaa  5880
ggccagcaaa aggccaggaa ccgtaaaaag gccgcgttgc tggcgttttt ccataggctc  5940
cgcccccctg acgagcatca caaaaatcga cgctcaagtc agaggtggcg aaacccgaca  6000
ggactataaa gataccaggc gtttccccct ggaagctccc tcgtgcgctc tcctgttccg  6060
accctgccgc ttaccggata cctgtccgcc tttctccctt cgggaagcgt ggcgctttct  6120
catagctcac gctgtaggta tctcagttcg gtgtaggtcg ttcgctccaa gctgggctgt  6180
gtgcacgaac cccccgttca gcccgaccgc tgcgccttat ccggtaacta tcgtcttgag  6240
tccaacccgg taagacacga cttatcgcca ctggcagcag ccactggtaa caggattagc  6300
agagcgaggt atgtaggcgg tgctacagag ttcttgaagt ggtggcctaa ctacggctac  6360
actagaagga cagtatttgg tatctgcgct ctgctgaagc cagttacctt cggaaaaaga  6420
gttggtagct cttgatccgg caaacaaacc accgctggta gcggtggttt ttttgtttgc  6480
aagcagcaga ttacgcgcag aaaaaaagga tctcaagaag atcctttgat cttttctacg  6540
gggtctgacg ctcagtggaa cgaaaactca cgttaaggga ttttggtcat gagattatca  6600
aaaaggatct tcacctagat ccttttaaat taaaaatgaa gttttaaatc aatctaaagt  6660
atatatgagt aaacttggtc tgacagttac caatgcttaa tcagtgaggc acctatctca  6720
gcgatctgtc tatttcgttc atccatagtt gcctgactcc ccgtcgtgta gataactacg  6780
atacgggagg gcttaccatc tggccccagt gctgcaatga taccgcgaga cccacgctca  6840
ccggctccag atttatcagc aataaaccag ccagccggaa gggccgagcg cagaagtggt  6900
cctgcaactt tatccgcctc catccagtct attaattgtt gccgggaagc tagagtaagt  6960
agttcgccag ttaatagttt gcgcaacgtt gttgccattg ctacaggcat cgtggtgtca  7020
cgctcgtcgt ttggtatggc ttcattcagc tccggttccc aacgatcaag gcgagttaca  7080
tgatccccca tgttgtgcaa aaaagcggtt agctccttcg gtcctccgat cgttgtcaga  7140
agtaagttgg ccgcagtgtt atcactcatg gttatggcag cactgcataa ttctcttact  7200
gtcatgccat ccgtaagatg cttttctgtg actggtgagt actcaaccaa gtcattctga  7260
gaatagtgta tgcggcgacc gagttgctct tgcccggcgt caatacggga taataccgcg  7320
ccacatagca gaactttaaa agtgctcatc attggaaaac gttcttcggg gcgaaaactc  7380
```

```
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttccttttt    7560
caatattatt gaagcattta tcagggttat tgtctcatga gcggatacat atttgaatgt    7620
atttagaaaa ataaacaaat aggggttccg cgcacatttc cccgaaaagt gccacctgaa    7680
cgaagcatct gtgcttcatt ttgtagaaca aaaatgcaac gcgagagcgc taattttttca    7740 aacaaagaat ctgagctgca ttttttacaga acagaaatgc aacgcgaaag cgctatttta    7800
ccaacgaaga atctgtgctt cattttttgta aaacaaaaat gcaacgcgag agcgctaatt    7860
tttcaaacaa agaatctgag ctgcattttt acagaacaga aatgcaacgc gagagcgcta    7920
ttttaccaac aaagaatcta tacttctttt ttgttctaca aaaatgcatc ccgagagcgc    7980 tattttttcta acaaagcatc ttagattact ttttttctcc tttgtgcgct ctataatgca    8040
gtctcttgat aactttttgc actgtaggtc cgttaaggtt agaagaaggc tactttggtg    8100
tctattttct cttccataaa aaaagcctga ctccacttcc cgcgtttact gattactagc    8160
gaagctgcgg gtgcatttttt tcaagataaa ggcatccccg attatattct ataccgatgt    8220
ggattgcgca tactttgtga acagaaagtg atagcgttga tgattcttca ttggtcagaa    8280
aattatgaac ggtttcttct attttgtctc tatatactac gtataggaaa tgtttacatt    8340
ttcgtattgt tttcgattca ctctatgaat agttcttact acaatttttt tgtctaaaga    8400
gtaatactag ataaaacat aaaaaatgta gaggtcgagt ttagatgcaa gttcaaggag    8460
cgaaaggtgg atgggtaggt tatataggga tatagcacag agatatatag caaagagata    8520
cttttgagca atgtttgtgg aagcggtatt cgcaatattt tagtagctcg ttacagtccg    8580
gtgcgttttt ggttttttga aagtgcgtct tcagagcgct tttggttttc aaaagcgctc    8640
tgaagttcct atactttcta gagaatagga acttcggaat aggaacttca aagcgtttcc    8700
gaaaacgagc gcttccgaaa atgcaacgcg agctgcgcac atacagctca ctgttcacgt    8760
cgcacctata tctgcgtgtt gcctgtatat atatatacat gagaagaacg gcatagtgcg    8820
tgtttatgct taaatgcgta cttatatgcg tctatttatg taggatgaaa ggtagtctag    8880
tacctcctgt gatattatcc cattccatgc ggggtatcgt atgcttcctt cagcactacc    8940
ctttagctgt tctatatgct gccactcctc aattggatta gtctcatcct tcaatgctat    9000
catttccttt gatattggat catactaaga aaccattatt atcatgacat taacctataa    9060
aaataggcgt atcacgaggc cctttcgtc                                      9089
```

<210> SEQ ID NO 59
<211> LENGTH: 672
<212> TYPE: DNA
<213> ORGANISM: Saccharomyces cerevisiae

<400> SEQUENCE: 59

```
agttcgagtt tatcattatc aatactgcca tttcaaagaa tacgtaaata attaatagta     60
gtgattttcc taactttatt tagtcaaaaa attagccttt taattctgct gtaacccgta    120
catgcccaaa atagggggcg ggttacacag aatatataac atcgtaggtg tctgggtgaa    180
cagtttattc ctggcatcca ctaaatataa tggagcccgc ttttttaagct ggcatccaga    240 aaaaaaaga tcccagcac caaaatattg ttttcttcac caaccatcag ttcataggtc    300
cattctctta gcgcaactac agagaacagg ggcacaaaca ggcaaaaaac gggcacaacc    360
```

```
tcaatggagt gatgcaacct gcctggagta aatgatgaca caaggcaatt gacccacgca    420
tgtatctatc tcattttctt acaccttcta ttaccttctg ctctctctga tttggaaaaa    480
gctgaaaaaa aaggttgaaa ccagttccct gaaattattc ccctacttga ctaataagta    540
tataaagacg gtaggtattg attgtaattc tgtaaatcta tttcttaaac ttcttaaatt    600 ctactttttat agttagtctt ttttttagtt ttaaaacacc aagaacttag tttcgaataa    660
acacacataa ac                                                        672

<210> SEQ ID NO 60
<211> LENGTH: 1023
<212> TYPE: DNA
<213> ORGANISM: Saccharomyces cerevisiae

<400> SEQUENCE: 60
caccgcggtg gggcgcgccc tattttcgag gaccttgtca ccttgagccc aagagagcca     60
agatttaaat tttcctatga cttgatgcaa attcccaaag ctaataacat gcaagacacg    120
tacggtcaag aagacatatt tgacctctta acaggttcag acgcgactgc ctcatcagta    180
agacccgttg aaaagaactt acctgaaaaa aacgaatata tactagcgtt gaatgttagc    240
gtcaacaaca agaagtttaa tgacgcggag gccaaggcaa aaagattcct tgattacgta    300
agggagttag aatcattttg aataaaaaac acgcttttc agttcgagtt tatcattatc    360
aatactgcca tttcaaagaa tacgtaaata attaatagta gtgattttcc taactttatt    420
tagtcaaaaa attagccttt taattctgct gtaacccgta catgcccaaa atagggggcg    480
ggttacacag aatatataac atcgtaggtg tctgggtgaa cagtttattc ctggcatcca    540
ctaaatataa tggagcccgc ttttttaagct ggcatccaga aaaaaaaaga atcccagcac    600
caaaatattg ttttcttcac caaccatcag ttcataggtc cattctctta gcgcaactac    660
agagaacagg ggcacaaaca ggcaaaaaac gggcacaacc tcaatggagt gatgcaacct    720
gcctggagta aatgatgaca caaggcaatt gacccacgca tgtatctatc tcattttctt    780
acaccttcta ttaccttctg ctctctctga tttggaaaaa gctgaaaaaa aaggttgaaa    840
ccagttccct gaaattattc ccctacttga ctaataagta tataaagacg gtaggtattg    900
attgtaattc tgtaaatcta tttcttaaac ttcttaaatt ctactttttat agttagtctt    960 ttttttagtt ttaaaacacc aagaacttag tttcgaataa acacacataa actagtaaac   1020
aaa                                                                 1023

<210> SEQ ID NO 61
<211> LENGTH: 21
<212> TYPE: DNA
<213> ORGANISM: artificial sequence
<220> FEATURE:
<223> OTHER INFORMATION: primer

<400> SEQUENCE: 61
caaaagctga gctccaccgc g                                               21

<210> SEQ ID NO 62
<211> LENGTH: 44
<212> TYPE: DNA
<213> ORGANISM: artificial sequence
<220> FEATURE:
<223> OTHER INFORMATION: primer

<400> SEQUENCE: 62
gtttactagt ttatgtgtgt ttattcgaaa ctaagttctt ggtg                       44
```

<210> SEQ ID NO 63
<211> LENGTH: 8994
<212> TYPE: DNA
<213> ORGANISM: artificial sequence
<220> FEATURE:
<223> OTHER INFORMATION: constructed plasmid

<400> SEQUENCE: 63

| | | | | | |
|---|---|---|---|---|---|
| ctagttctag | agcggccgcc | accgcggtgg | agctccagct | tttgttccct | ttagtgaggg | 60 |
| ttaattgcgc | gcttggcgta | atcatggtca | tagctgtttc | ctgtgtgaaa | ttgttatccg | 120 |
| ctcacaattc | cacacaacat | aggagccgga | agcataaagt | gtaaagcctg | gggtgcctaa | 180 |
| tgagtgaggt | aactcacatt | aattgcgttg | cgctcactgc | ccgctttcca | gtcgggaaac | 240 |
| ctgtcgtgcc | agctgcatta | atgaatcggc | caacgcgcgg | ggagaggcgg | tttgcgtatt | 300 |
| gggcgctctt | ccgcttcctc | gctcactgac | tcgctgcgct | cggtcgttcg | gctgcggcga | 360 |
| gcggtatcag | ctcactcaaa | ggcggtaata | cggttatcca | cagaatcagg | ggataacgca | 420 |
| ggaaagaaca | tgtgagcaaa | aggccagcaa | aaggccagga | accgtaaaaa | ggccgcgttg | 480 |
| ctggcgtttt | tccataggct | ccgcccccct | gacgagcatc | acaaaaatcg | acgctcaagt | 540 |
| cagaggtggc | gaaacccgac | aggactataa | agataccagg | cgtttccccc | tggaagctcc | 600 |
| ctcgtgcgct | ctcctgttcc | gaccctgccg | cttaccggat | acctgtccgc | ctttctccct | 660 |
| tcgggaagcg | tggcgctttc | tcatagctca | cgctgtaggt | atctcagttc | ggtgtaggtc | 720 |
| gttcgctcca | agctgggctg | tgtgcacgaa | ccccccgttc | agcccgaccg | ctgcgcctta | 780 |
| tccggtaact | atcgtcttga | gtccaacccg | gtaagacacg | acttatcgcc | actggcagca | 840 |
| gccactggta | acaggattag | cagagcgagg | tatgtaggcg | gtgctacaga | gttcttgaag | 900 |
| tggtggccta | actacggcta | cactagaagg | acagtatttg | gtatctgcgc | tctgctgaag | 960 |
| ccagttacct | tcggaaaaag | agttggtagc | tcttgatccg | gcaaacaaac | caccgctggt | 1020 |
| agcggtggtt | tttttgtttg | caagcagcag | attacgcgca | gaaaaaaagg | atctcaagaa | 1080 |
| gatcctttga | tcttttctac | ggggtctgac | gctcagtgga | acgaaaactc | acgttaaggg | 1140 |
| attttggtca | tgagattatc | aaaaaggatc | ttcacctaga | tccttttaaa | ttaaaaatga | 1200 |
| agttttaaat | caatctaaag | tatatatgag | taaacttggt | ctgacagtta | ccaatgctta | 1260 |
| atcagtgagg | cacctatctc | agcgatctgt | ctatttcgtt | catccatagt | tgcctgactc | 1320 |
| cccgtcgtgt | agataactac | gatacgggag | ggcttaccat | ctggccccag | tgctgcaatg | 1380 |
| ataccgcgag | acccacgctc | accggctcca | gatttatcag | caataaacca | gccagccgga | 1440 |
| agggccgagc | gcagaagtgg | tcctgcaact | ttatccgcct | ccatccagtc | tattaattgt | 1500 |
| tgccgggaag | ctagagtaag | tagttcgcca | gttaatagtt | tgcgcaacgt | tgttgccatt | 1560 |
| gctacaggca | tcgtggtgtc | acgctcgtcg | tttggtatgg | cttcattcag | ctccggttcc | 1620 |
| caacgatcaa | ggcgagttac | atgatccccc | atgttgtgca | aaaaagcggt | tagctccttc | 1680 |
| ggtcctccga | tcgttgtcag | aagtaagttg | gccgcagtgt | tatcactcat | ggttatggca | 1740 |
| gcactgcata | attctcttac | tgtcatgcca | tccgtaagat | gcttttctgt | gactggtgag | 1800 |
| tactcaacca | agtcattctg | agaatagtgt | atgcggcgac | cgagttgctc | ttgcccggcg | 1860 |
| tcaatacggg | ataataccgc | gccacatagc | agaactttaa | aagtgctcat | cattggaaaa | 1920 |
| cgttcttcgg | ggcgaaaact | ctcaaggatc | ttaccgctgt | tgagatccag | ttcgatgtaa | 1980 |
| cccactcgtg | cacccaactg | atcttcagca | tcttttactt | tcaccagcgt | ttctgggtga | 2040 |

```
gcaaaaacag gaaggcaaaa tgccgcaaaa aagggaataa gggcgacacg gaaatgttga    2100
atactcatac tcttcctttt tcaatattat tgaagcattt atcagggtta ttgtctcatg    2160
agcggataca tatttgaatg tatttagaaa aataaacaaa tagggggttcc gcgcacattt    2220 ccccgaaaag tgccacctga acgaagcatc tgtgcttcat tttgtagaac aaaaatgcaa    2280
cgcgagagcg ctaattttc aaacaaagaa tctgagctgc attttacag aacagaaatg    2340 caacgcgaaa gcgctatttt accaacgaag aatctgtgct tcattttgt aaaacaaaaa    2400 tgcaacgcga gagcgctaat ttttcaaaca aagaatctga gctgcatttt tacagaacag    2460
aaatgcaacg cgagagcgct atttaccaa caaagaatct atacttcttt tttgttctac    2520
aaaaatgcat cccgagagcg ctattttct aacaaagcat cttagattac ttttttctc    2580 ctttgtgcgc tctataatgc agtctcttga taactttttg cactgtaggt ccgttaaggt    2640
tagaagaagg ctactttggt gtctatttc tcttccataa aaaaagcctg actccacttc    2700
ccgcgtttac tgattactag cgaagctgcg ggtgcatttt ttcaagataa aggcatcccc    2760
gattatattc tataccgatg tggattgcgc atactttgtg aacagaaagt gatagcgttg    2820
atgattcttc attggtcaga aaattatgaa cggtttcttc tattttgtct ctatatacta    2880
cgtataggaa atgtttacat tttcgtattg ttttcgattc actctatgaa tagttcttac    2940 tacaatttt ttgtctaaag agtaatacta gagataaaca taaaaatgt agaggtcgag    3000 tttagatgca agttcaagga gcgaaaggtg gatgggtagg ttatataggg atatagcaca    3060
gagatatata gcaaagagat acttttgagc aatgtttgtg gaagcggtat tcgcaatatt    3120
ttagtagctc gttacagtcc ggtgcgtttt tggtttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaataggcg tatcacgagg cccttttcgtc tcgcgcgttt    3660 cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaacttc accattatgg    3900 gaaatgcttc aagaaggtat tgacttaaac tccatcaaat ggtcaggtca ttgagtgttt    3960
tttatttgtt gtatttttt tttttagag aaaatcctcc aatatcaaat taggaatcgt    4020
agtttcatga ttttctgtta cacctaactt tttgtgtggt gccctcctcc ttgtcaatat    4080
taatgttaaa gtgcaattct ttttccttat cacgttgagc cattagtatc aatttgctta    4140
cctgtattcc tttactatcc tccttttct ccttcttgat aaatgtatgt agattgcgta    4200
tatagtttcg tctaccctat gaacatattc cattttgtaa tttcgtgtcg tttctattat    4260
gaatttcatt tataaagttt atgtacaaat atcataaaaa aagagaatct ttttaagcaa    4320
ggattttctt aacttcttcg gcgacagcat caccgacttc ggtggtactg ttggaaccac    4380
ctaaatcacc agttctgata cctgcatcca aaacctttt aactgcatct tcaatggcct    4440
```

| | |
|---|---|
| taccttcttc aggcaagttc aatgacaatt tcaacatcat tgcagcagac aagatagtgg | 4500 |
| cgatagggtc aaccttattc tttggcaaat ctggagcaga accgtggcat ggttcgtaca | 4560 |
| aaccaaatgc ggtgttcttg tctggcaaag aggccaagga cgcagatggc aacaaaccca | 4620 |
| aggaacctgg gataacggag gcttcatcgg agatgatatc accaaacatg ttgctggtga | 4680 |
| ttataatacc atttaggtgg gttgggttct taactaggat catggcggca gaatcaatca | 4740 |
| attgatgttg aaccttcaat gtagggaatt cgttcttgat ggtttcctcc acagtttttc | 4800 |
| tccataatct tgaagaggcc aaaagattag ctttatccaa ggaccaaata ggcaatggtg | 4860 |
| gctcatgttg tagggccatg aaagcggcca ttcttgtgat tctttgcact tctggaacgg | 4920 |
| tgtattgttc actatcccaa gcgacaccat caccatcgtc ttcctttctc ttaccaaagt | 4980 |
| aaatacctcc cactaattct ctgacaacaa cgaagtcagt acctttagca aattgtggct | 5040 |
| tgattggaga taagtctaaa agagagtcgg atgcaaagtt acatggtctt aagttggcgt | 5100 |
| acaattgaag ttcttacgg atttttagta aaccttgttc aggtctaaca ctaccggtac | 5160 |
| cccatttagg accagccaca gcacctaaca aaacggcatc aaccttcttg gaggcttcca | 5220 |
| gcgcctcatc tggaagtggg acacctgtag catcgatagc agcaccacca attaaatgat | 5280 |
| tttcgaaatc gaacttgaca ttggaacgaa catcagaaat agctttaaga accttaatgg | 5340 |
| cttcggctgt gatttcttga ccaacgtggt cacctggcaa aacgacgatc ttcttagggg | 5400 |
| cagacatagg ggcagacatt agaatggtat atccttgaaa tatatatata tattgctgaa | 5460 |
| atgtaaaagg taagaaaagt tagaaagtaa gacgattgct aaccacctat tggaaaaaac | 5520 |
| aataggtcct taaataatat tgtcaacttc aagtattgtg atgcaagcat ttagtcatga | 5580 |
| acgcttctct attctatatg aaaagccggt tccggcctct caccttccct ttttctccca | 5640 |
| attttcagt tgaaaaaggt atatgcgtca ggcgacctct gaaattaaca aaaaatttcc | 5700 |
| agtcatcgaa tttgattctg tgcgatagcg cccctgtgtg ttctcgttat gttgaggaaa | 5760 |
| aaaataatgg ttgctaagag attcgaactc ttgcatctta cgatacctga gtattcccac | 5820 |
| agttaactgc ggtcaagata tttcttgaat caggcgcctt agaccgctcg gccaaacaac | 5880 |
| caattacttg ttgagaaata gagtataatt atcctataaa tataacgttt ttgaacacac | 5940 |
| atgaacaagg aagtacagga caattgattt tgaagagaat gtggattttg atgtaattgt | 6000 |
| tgggattcca tttttaataa ggcaataata ttaggtatgt ggatatacta gaagttctcc | 6060 |
| tcgaccgtcg atatgcggtg tgaaataccg cacagatgcg taaggagaaa ataccgcatc | 6120 |
| aggaaattgt aaacgttaat attttgttaa aattcgcgtt aaattttgt taaatcagct | 6180 |
| catttttaa ccaataggcc gaaatcggca aaatcccttaa taaatcaaaa gaatagaccg | 6240 |
| agatagggtt gagtgttgtt ccagtttgga acaagagtcc actattaaag aacgtggact | 6300 |
| ccaacgtcaa agggcgaaaa accgtctatc agggcgatgg cccactacgt gaaccatcac | 6360 |
| cctaatcaag ttttttgggg tcgaggtgcc gtaaagcact aaatcggaac cctaaaggga | 6420 |
| gccccgatt tagagcttga cggggaaagc cggcgaacgt ggcgagaaag gaagggaaga | 6480 |
| aagcgaaagg agcgggcgct agggcgctgg caagtgtagc ggtcacgctg cgcgtaacca | 6540 |
| ccacacccgc cgcgcttaat gcgccgctac agggcgcgtc gcgccattcg ccattcaggc | 6600 |
| tgcgcaactg ttgggaaggg cgatcggtgc gggcctcttc gctattacgc cagctggcga | 6660 |
| aaggggatg tgctgcaagg cgattaagtt gggtaacgcc agggttttcc cagtcacgac | 6720 |
| gttgtaaaac gacggccagt gagcgcgcgt aatacgactc actatagggc gaattgggta | 6780 |

```
ccgggccccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
tatatatata tagccatagt gatgtctaag taaccttat ggtatatttc ttaatgtgga    7200
aagatactag cgcgcgcacc cacacacaag cttcgtcttt tcttgaagaa aagaggaagc    7260
tcgctaaatg ggattccact ttccgttccc tgccagctga tggaaaaagg ttagtggaac    7320
gatgaagaat aaaaagagag atccactgag gtgaaatttc agctgacagc gagtttcatg    7380
atcgtgatga acaatggtaa cgagttgtgg ctgttgccag ggagggtggt tctcaacttt    7440
taatgtatgg ccaaatcgct acttgggttt gttatataac aaagaagaaa taatgaactg    7500
attctcttcc tccttcttgt cctttcttaa ttctgttgta attaccttcc tttgtaattt    7560
tttttgtaat tattcttctt aataatccaa acaaacacac atattacaat agctagctga    7620
ggatgaaggc attagtttat catggggatc acaaatttc gttagaagac aaaccaaaac    7680
ccactctgca gaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaaggggg    7860
ataaagttt aatctcctgc gttactagct gtggatcgtg tgattattgc aagaagcaac    7920
tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tataccccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactacccca atgttgatga    8520
aggtagcctc tactgataaa ttgcctttaa agaaaatgat tactcacagg tttgagttag    8580
ctgaaatcga acacgcatat caggttttct tgaatggcgc taaagaaaaa gctatgaaga    8640
ttattctatc taatgcaggt gccgcctaat taattaagag taagcgaatt tcttatgatt    8700
tatgattttt attattaaat aagttataaa aaaataagt gtatacaaat tttaaagtga    8760
ctcttaggtt ttaaaacgaa aattcttatt cttgagtaac tctttcctgt aggtcaggtt    8820
gctttctcag gtatagcatg aggtcgctct tattgaccac acctctaccg gcatgccgag    8880
caaatgcctg caaatcgctc cccatttcac ccaattgtag atatgctaac tccagcaatg    8940
agttgatgaa tctcggtgtg tattttatgt cctcagagga caacacctgt ggta          8994
```

<210> SEQ ID NO 64
<211> LENGTH: 753
<212> TYPE: DNA
<213> ORGANISM: Saccharomyces cerevisiae

<400> SEQUENCE: 64

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatagccata    300
gtgatgtcta agtaaccttt atggtatatt tcttaatgtg gaaagatact agcgcgcgca    360
cccacacaca agcttcgtct tttcttgaag aaaagaggaa gctcgctaaa tgggattcca    420
ctttccgttc cctgccagct gatggaaaaa ggttagtgga acgatgaaga ataaaaagag    480
agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt ttgttatata acaaagaaga ataatgaac tgattctctt cctccttctt     660
gtcctttctt aattctgttg taattacctt cctttgtaat tttttttgta attattcttc    720
ttaataatcc aaacaaacac acatattaca ata                                 753
```

<210> SEQ ID NO 65
<211> LENGTH: 316
<212> TYPE: DNA
<213> ORGANISM: Saccharomyces cerevisiae

<400> SEQUENCE: 65

```
gagtaagcga atttcttatg atttatgatt tttattatta aataagttat aaaaaaaata      60
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtatttta tgtcctcaga    300
ggacaacacc tgtggt                                                    316
```

<210> SEQ ID NO 66
<211> LENGTH: 39
<212> TYPE: DNA
<213> ORGANISM: artificial sequence
<220> FEATURE:
<223> OTHER INFORMATION: primer

<400> SEQUENCE: 66

```
cacacatatt acaatagcta gctgaggatg aaagctctg                            39
```

<210> SEQ ID NO 67
<211> LENGTH: 39
<212> TYPE: DNA
<213> ORGANISM: artificial sequence
<220> FEATURE:
<223> OTHER INFORMATION: primer

<400> SEQUENCE: 67

```
cagagctttc atcctcagct agctattgta atatgtgtg                            39
```

<210> SEQ ID NO 68
<211> LENGTH: 9491
<212> TYPE: DNA
<213> ORGANISM: artificial sequence
<220> FEATURE:

<223> OTHER INFORMATION: constructed plasmid

<400> SEQUENCE: 68

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcggggctgg cttaactatg cggcatcaga gcagattgta ctgagagtgc      180
accataaatt cccgttttaa gagcttggtg agcgctagga gtcactgcca ggtatcgttt      240
gaacacggca ttagtcaggg aagtcataac acagtccttt cccgcaattt tcttttttcta     300
ttactcttgg cctcctctag tacactctat atttttttat gcctcggtaa tgattttcat      360
ttttttttt cccctagcgg atgactcttt tttttcttta gcgattggca ttatcacata       420
atgaattata cattatataa agtaatgtga tttcttcgaa gaatatacta aaaaatgagc      480
aggcaagata acgaaggca aagatgacag agcagaaagc cctagtaaag cgtattacaa       540
atgaaaccaa gattcagatt gcgatctctt taaagggtgg tcccctagcg atagagcact     600
cgatcttccc agaaaagag gcagaagcag tagcagaaca ggccacacaa tcgcaagtga      660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag cttttaaaga ggccctactg gcgcgtggag     840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca   1080
aggctcttgc ggttgccata agaaagcca cctcgcccaa tggtaccaac gatgttccct     1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt   1320
ccttttttct ttttgctttt tcttttttttt tctcttgaac tcgacggatc tatgcggtgt    1380
gaaataccgc acagatgcgt aaggagaaaa taccgcatca ggaaattgta aacgttaata   1440
ttttgttaaa attcgcgtta aattttttgtt aaatcagctc atttttttaac caataggccg   1500
aaatcggcaa aatcccttat aaatcaaaag aatagaccga tagggttg agtgttgttc      1560
cagtttggaa caagagtcca ctattaaaga acgtggactc caacgtcaaa gggcgaaaaa     1620
ccgtctatca gggcgatggc ccactacgtg aaccatcacc ctaatcaagt ttttttgggt      1680
cgaggtgccg taaagcacta atcggaacc ctaaagggag ccccgattt agagcttgac       1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa agggggatgt gctgcaaggc   1980
gattaagttg ggtaacgcca gggttttccc agtcacgacg ttgtaaaacg acggccagtg    2040
agcgcgcgta atacgactca ctatagggcg aattgggtac cgggcccccc ctcgaggtcg    2100
acggcgcgcc actggtagag agcgactttg tatgccccaa ttgcgaaacc cgcgatatcc    2160
ttctcgattc tttagtaccc gaccaggaca aggaaaagga ggtcgaaacg ttttttgaaga   2220
aacaagagga actacacgga agctctaaag atggcaacca gccagaaact aagaaaatga   2280
```

```
agttgatgga tccaactggc accgctggct tgaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat gataggaatg   2640
ggattcttct attttttcctt tttccattct agcagccgtc gggaaaacgt ggcatcctct   2700
ctttcgggct caattggagt cacgctgccg tgagcatcct ctctttccat atctaacaac   2760
tgagcacgta accaatggaa aagcatgagc ttagcgttgc tccaaaaaag tattggatgg   2820
ttaataccat ttgtctgttc tcttctgact ttgactcctc aaaaaaaaaa aatctacaat   2880
caacagatcg cttcaattac gccctcacaa aaacttttttt ccttcttctt cgcccacgtt   2940 aaatttatc cctcatgttg tctaacggat ttctgcactt gatttattat aaaaagacaa   3000
agacataata cttctctatc aatttcagtt attgttcttc cttgcgttat tcttctgttc   3060
ttctttttct tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
tatcgtcggt gtcatttcaa cttgggctga aaacacacct tgtaatatcc acttacatga   3300
ctttggtaaa ctagccaaag tcggtgttaa ggaagctggt gcttggccag ttcagttcgg   3360
aacaatcacg gtttctgatg gaatcgccat gggaacccaa ggaatgcgtt tctccttgac   3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaagaaa gcagatattg aagaagctgg   3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag gggtaccagc agttatgaaa tatctcctta aaaatggctt   4140
ccttcatggt gaccgtatca cttgtactgg caaaacagtc gctgaaaatt tgaaggcttt   4200
tgatgattta acacctggtc aaaaggttat tatgccgctt gaaaatccta acgtgaaga   4260 tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
cattgaagct gtcttgaatg atgatattgt tgatggtgat gttgttgtcg tacgttttgt   4440
aggaccaaag ggcggtcctg gtatgcctga aatgctttcc cttttcatcaa tgattgttgg   4500 taaagggcaa ggtgaaaaag ttgcccttct gacagatggc cgcttctcag gtggtactta   4560
tggtcttgtc gtgggtcata tcgctcctga agcacaagat ggcggtccaa tcgcctacct   4620
```

```
gcaaacagga gacatagtca ctattgacca agacactaag gaattacact ttgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagtttttt aatgagtatt gaatctgttt agaaataatg    4920
gaatattatt tttatttatt tatttatatt attggtcggc tcttttcttc tgaaggtcaa    4980
tgacaaaatg atatgaagga aataatgatt tctaaaattt tacaacgtaa gatattttta    5040
caaaagccta gctcatcttt tgtcatgcac tattttactc acgcttgaaa ttaacggcca    5100
gtccactgcg gagtcatttc aaagtcatcc taatcgatct atcgtttttg atagctcatt    5160
ttggagttcg cgattgtctt ctgttattca caactgtttt aatttttatt tcattctgga    5220
actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgttttgtt ctcccatcac aatttaatat acctgatgga    5520
ttcttatgaa gcgctgggta atggacgtgt cactctactt cgccttttc cctactcctt     5580 ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga aattgttatc cgctcacaat tccacacaac ataggagccg aagcataaa     6000 gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacgttatc     6240 cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
tcagcccgac cgctgcgcct tatccggtaa ctatcgtctt gagtccaacc cggtaagaca    6660
cgacttatcg ccactggcag cagccactgg taacaggatt agcagagcga ggtatgtagg    6720
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg tttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020
```

```
gatccttta  aattaaaaat  gaagttttaa  atcaatctaa  agtatatatg  agtaaacttg   7080
gtctgacagt  taccaatgct  taatcagtga  ggcacctatc  tcagcgatct  gtctatttcg   7140
ttcatccata  gttgcctgac  tccccgtcgt  gtagataact  acgatacggg  agggcttacc   7200
atctggcccc  agtgctgcaa  tgataccgcg  agacccacgc  tcaccggctc  cagatttatc   7260
agcaataaac  cagccagccg  gaagggccga  gcgcagaagt  ggtcctgcaa  ctttatccgc   7320
ctccatccag  tctattaatt  gttgccggga  agctagagta  agtagttcgc  cagttaatag   7380
tttgcgcaac  gttgttgcca  ttgctacagg  catcgtggtg  tcacgctcgt  cgtttggtat   7440
ggcttcattc  agctccggtt  cccaacgatc  aaggcgagtt  acatgatccc  ccatgttgtg   7500
caaaaaagcg  gttagctcct  tcggtcctcc  gatcgttgtc  agaagtaagt  tggccgcagt   7560
gttatcactc  atggttatgg  cagcactgca  taattctctt  actgtcatgc  catccgtaag   7620
atgcttttct  gtgactggtg  agtactcaac  caagtcattc  tgagaatagt  gtatgcggcg   7680
accgagttgc  tcttgcccgg  cgtcaatacg  ggataatacc  gcgccacata  gcagaacttt   7740
aaaagtgctc  atcattggaa  aacgttcttc  ggggcgaaaa  ctctcaagga  tcttaccgct   7800
gttgagatcc  agttcgatgt  aacccactcg  tgcacccaac  tgatcttcag  catcttttac   7860
tttcaccagc  gtttctgggt  gagcaaaaac  aggaaggcaa  aatgccgcaa  aaaagggaat   7920
aagggcgaca  cggaaatgtt  gaatactcat  actcttcctt  tttcaatatt  attgaagcat   7980
ttatcagggt  tattgtctca  tgagcggata  catatttgaa  tgtatttaga  aaaataaaca   8040
aataggggtt  ccgcgcacat  ttccccgaaa  agtgccacct  gaacgaagca  tctgtgcttc   8100
attttgtaga  acaaaaatgc  aacgcgagag  cgctaatttt  tcaaacaaag  aatctgagct   8160 gcattttac  agaacagaaa  tgcaacgcga  aagcgctatt  ttaccaacga  agaatctgtg   8220
cttcattttt  gtaaaacaaa  aatgcaacgc  gagagcgcta  ttttttcaaa  caagaatctg   8280
gagctgcatt  tttacagaac  agaaatgcaa  cgcgagagcg  ctattttacc  aacaaagaat   8340
ctatacttct  tttttgttct  acaaaaatgc  atcccgagag  cgctattttt  ctaacaaagc   8400
atcttagatt  acttttttc  tcctttgtgc  gctctataat  gcagtctctt  gataactttt   8460
tgcactgtag  gtccgttaag  gttagaagaa  ggctactttg  gtgtctattt  tctcttccat   8520
aaaaaaagcc  tgactccact  tcccgcgttt  actgattact  agcgaagctg  cgggtgcatt   8580
ttttcaagat  aaaggcatcc  ccgattatat  tctataccga  tgtggattgc  gcatactttg   8640
tgaacagaaa  gtgatagcgt  tgatgattct  tcattggtca  gaaaattatg  aacggtttct   8700
tctattttgt  ctctatatac  tacgtatagg  aaatgtttac  attttcgtat  tgttttcgat   8760
tcactctatg  aatagttctt  actacaattt  ttttgtctaa  agagtaatac  tagagataaa   8820
cataaaaaat  gtagaggtcg  agtttagatg  caagttcaag  gagcgaaagg  tggatgggta   8880
ggttatatag  ggatatagca  cagagatata  tagcaaagag  atactttga  gcaatgtttg   8940 tggaagcggt  attcgcaata  ttttagtagc  tcgttacagt  ccggtgcgtt  tttggttttt   9000
tgaaagtgcg  tcttcagagc  gcttttggtt  ttcaaaagcg  ctctgaagtt  cctatacttt   9060
ctagagaata  ggaacttcgg  aataggaact  tcaaagcgtt  tccgaaaacg  agcgcttccg   9120
aaaatgcaac  gcgagctgcg  cacatacagc  tcactgttca  cgtcgcacct  atatctgcgt   9180
gttgcctgta  tatatatata  catgagaaga  acggcatagt  gcgtgtttat  gcttaaatgc   9240
gtacttatat  gcgtctattt  atgtaggatg  aaaggtagtc  tagtacctcc  tgtgatatta   9300
tcccattcca  tgcggggtat  cgtatgcttc  cttcagcact  acccttagc  tgttctatat   9360
```

```
gctgccactc ctcaattgga ttagtctcat ccttcaatgc tatcatttcc tttgatattg   9420
gatcatctaa gaaaccatta ttatcatgac attaacctat aaaaataggc gtatcacgag   9480 gcccttttcgt c                                                       9491

<210> SEQ ID NO 69
<211> LENGTH: 1000
<212> TYPE: DNA
<213> ORGANISM: Saccharymoces cerevisiae

<400> SEQUENCE: 69
gttaattcaa attaattgat atagtttttt aatgagtatt gaatctgttt agaaataatg     60
gaatattatt tttatttatt tatttatatt attggtcggc tcttttcttc tgaaggtcaa    120
tgacaaaatg atatgaagga aataatgatt tctaaaattt tacaacgtaa gatattttta    180
caaaagccta gctcatcttt tgtcatgcac tattttactc acgcttgaaa ttaacggcca    240
gtccactgcg gagtcatttc aaagtcatcc taatcgatct atcgttttg  atagctcatt    300 ttggagttcg cgattgtctt ctgttattca caactgtttt aattttttatt tcattctgga   360 actcttcgag ttctttgtaa agtctttcat agtagcttac tttatcctcc aacatatttta   420 acttcatgtc aatttcggct cttaaatttt ccacatcatc aagttcaaca tcatctttta    480
acttgaattt attctctagc tcttccaacc aagcctcatt gctccttgat ttactggtga    540
aaagtgatac actttgcgcg caatccaggt caaaactttc ctgcaaagaa ttcaccaatt    600
tctcgacatc atagtacaat ttgttttgtt ctcccatcac aatttaatat acctgatgga    660
ttcttatgaa gcgctgggta atggacgtgt cactctactt cgccttttc cctactcctt     720 ttagtacgga agacaatgct aataaataag agggtaataa taatattatt aatcggcaaa    780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000

<210> SEQ ID NO 70
<211> LENGTH: 760
<212> TYPE: PRT
<213> ORGANISM: Escherichia coli

<400> SEQUENCE: 70

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
        50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125
```

```
Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540
```

| | | | | | | | | | | | | | | | |
|---|---|---|---|---|---|---|---|---|---|---|---|---|---|---|---|
|Val|Lys|Pro|Ile|Arg|Asp|Glu|Asp|Gly|Leu|Ala|Ile|Asp|Phe|Glu|Ile|
|545| | | |550| | | |555| | | |560| | | |

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760

<210> SEQ ID NO 71
<211> LENGTH: 2283
<212> TYPE: DNA
<213> ORGANISM: Escherichia coli

<400> SEQUENCE: 71

```
atgtccgagc ttaatgaaaa gttagccaca gcctgggaag ttttaccaa aggtgactgg      60 cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcacct ctcacgacgc tggctacatc aacaagcagc ttgagaaaat cgttggtctg     300
cagactgaag ctccgctgaa acgtgctctt atcccgttcg gtggtatcaa aatgatcgaa     360
ggttcctgca aagcgtacaa ccgcgaactg gatccgatga tcaaaaaaat cttcactgaa     420
taccgtaaaa ctcacaacca gggcgtgttc gacgtttaca ctccggacat cctgcgttgc     480
cgtaaatctg gtgttctgac cggtctgcca gatgcatatg gccgtggccg tatcatcggt     540
gactaccgtc gcgttgcgct gtacggtatc gactacctga tgaaagacaa actggcacag     600
ttcacttctc tgcaggctga tctggaaaac ggcgtaaacc tggaacagac tatccgtctg     660
cgcgaagaaa tcgctgaaca gcaccgcgct ctgggtcaga tgaaagaaat ggctgcgaaa     720
tacggctacg acatctctgg tccggctacc aacgctcagg aagctatcca gtggacttac     780
ttcggctacc tggctgctgt taagtctcag aacggtgctg caatgtcctt cggtcgtacc     840
tccaccttcc tggatgtgta catcgaacgt gacctgaaag ctggcaagat caccgaacaa     900
```

```
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg taccctggtt accaaaaaca gcttccgttt cctgaacacc   1080
ctgtacacca tgggtccgtc tccggaaccg aacatgacca ttctgtggtc tgaaaaactg   1140
ccgctgaact tcaagaaatt cgccgctaaa gtgtccatcg acacctcttc tctgcagtat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca gtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga agttaaaacc gattcgtgac gaagacggtc tggctatcga cttcgaaatc   1680
gaaggcgaat acccgcagtt tggtaacaat gatccgcgtg tagatgaccct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggaccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact ccaccacga agcatccatc   2100
gaaggtggtc agcacctgaa cgttaacgtg atgaaccgtg aaatgctgct cgacgcgatg   2160
gaaaacccgg aaaatatccc gcagctgacc atccgtgtat ctggctacgc agtacgtttc   2220
aactcgctga ctaaagaaca gcagcaggac gttattactc gtaccttcac tcaatctatg   2280
taa                                                                  2283
```

<210> SEQ ID NO 72
<211> LENGTH: 244
<212> TYPE: PRT
<213> ORGANISM: Escherichia coli

<400> SEQUENCE: 72

```
Met Ala Glu Met Lys Asn Leu Lys Ile Glu Val Val Arg Tyr Asn Pro
1               5                   10                  15

Glu Val Asp Thr Ala Pro His Ser Ala Phe Glu Val Pro Tyr Asp
            20                  25                  30

Ala Thr Thr Ser Leu Leu Asp Ala Leu Gly Tyr Ile Lys Asp Asn Leu
        35                  40                  45

Ala Pro Asp Leu Ser Tyr Arg Trp Ser Cys Arg Met Ala Ile Cys Gly
    50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
```

| | | | | | | | | | | | | | | |
|---|---|---|---|---|---|---|---|---|---|---|---|---|---|---|
| | | | | 115 | | | | | 120 | | | | | 125 |

Asp Gln Gly Thr Asn Ile Gln Thr Pro Ala Gln Met Ala Lys Tyr His
     130                         135                      140

Gln Phe Ser Gly Cys Ile Asn Cys Gly Leu Cys Tyr Ala Ala Cys Pro
145                      150                    155                    160

Gln Phe Gly Leu Asn Pro Glu Phe Ile Gly Pro Ala Ala Ile Thr Leu
     165                         170                      175

Ala His Arg Tyr Asn Glu Asp Ser Arg Asp His Gly Lys Lys Glu Arg
         180                      185                    190

Met Ala Gln Leu Asn Ser Gln Asn Gly Val Trp Ser Cys Thr Phe Val
         195                      200                    205

Gly Tyr Cys Ser Glu Val Cys Pro Lys His Val Asp Pro Ala Ala Ala
     210                        215                    220

Ile Gln Gln Gly Lys Val Glu Ser Ser Lys Asp Phe Leu Ile Ala Thr
225                      230                    235                    240

Leu Lys Pro Arg

<210> SEQ ID NO 73
<211> LENGTH: 735
<212> TYPE: DNA
<213> ORGANISM: Escherichia coli

<400> SEQUENCE: 73

| | | |
|---|---|---:|
| atggctgaga tgaaaaacct gaaaattgag gtggtgcgct ataacccgga agtcgatacc | | 60 |
| gcaccgcata gcgcattcta tgaagtgcct tatgacgcaa ctacctcatt actggatgcg | | 120 |
| ctgggctaca tcaaagacaa cctggcaccg gacctgagct accgctggtc ctgccgtatg | | 180 |
| gcgatttgtg gttcctgcgg catgatggtt aacaacgtgc aaaactggc atgtaaaacc | | 240 |
| ttcctgcgtg attacaccga cggtatgaag gttgaagcgt tagctaactt cccgattgaa | | 300 |
| cgcgatctgg tggtcgatat gacccacttc atcgaaagtc tggaagcgat caaaccgtac | | 360 |
| atcatcggca actcccgcac cgcggatcag ggtactaaca tccagacccc ggcgcagatg | | 420 |
| gcgaagtatc accagttctc cggttgcatc aactgtggtt tgtgctacgc cgcgtgcccg | | 480 |
| cagtttggcc tgaacccaga gttcatcggt ccggctgcca ttacgctggc gatcgttat | | 540 |
| aacgaagata ccgcgaccca cggtaagaag gagcgtatgg cgcagttgaa cagccagaac | | 600 |
| ggcgtatgga gctgtacttt cgtgggctac tgctccgaag tctgcccgaa acacgtcgat | | 660 |
| ccggctgcgg ccattcagca gggcaaagta gaaagttcga agactttct tatcgcgacc | | 720 |
| ctgaaaccac gctaa | | 735 |

<210> SEQ ID NO 74
<211> LENGTH: 891
<212> TYPE: PRT
<213> ORGANISM: Escherichia coli

<400> SEQUENCE: 74

Met Ala Val Thr Asn Val Ala Glu Leu Asn Ala Leu Val Glu Arg Val
1               5                    10                    15

Lys Lys Ala Gln Arg Glu Tyr Ala Ser Phe Thr Gln Glu Gln Val Asp
          20                      25                    30

Lys Ile Phe Arg Ala Ala Ala Leu Ala Ala Asp Ala Arg Ile Pro
             35                    40                    45

Leu Ala Lys Met Ala Val Ala Glu Ser Gly Met Gly Ile Val Glu Asp
50                      55                    60

```
Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Thr Phe Gly
                 85                  90                  95

Thr Ile Thr Ile Ala Glu Pro Ile Gly Ile Cys Gly Ile Val Pro
                100                 105                 110

Thr Thr Asn Pro Thr Ser Thr Ala Ile Phe Lys Ser Leu Ile Ser Leu
                115                 120                 125

Lys Thr Arg Asn Ala Ile Ile Phe Ser Pro His Pro Arg Ala Lys Asp
            130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
                180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Ile Asp Glu Thr
210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
            275                 280                 285

Asn Gly Ala Leu Asn Ala Ala Ile Val Gly Gln Pro Ala Tyr Lys Ile
            290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
            370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
                420                 425                 430

Val Gly Pro Lys His Leu Ile Asn Lys Lys Thr Val Ala Lys Arg Ala
                435                 440                 445

Glu Asn Met Leu Trp His Lys Leu Pro Lys Ser Ile Tyr Phe Arg Arg
                450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
```

```
            485                 490                 495
Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
                690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
                770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 75
```

<211> LENGTH: 2676
<212> TYPE: DNA
<213> ORGANISM: Escherichia coli

<400> SEQUENCE: 75

| | | | | | |
|---|---|---|---|---|---|
| atggctgtta | ctaatgtcgc | tgaacttaac | gcactcgtag | agcgtgtaaa | aaaagcccag | 60 |
| cgtgaatatg | ccagtttcac | tcaagagcaa | gtagacaaaa | tcttccgcgc | cgccgctctg | 120 |
| gctgctgcag | atgctcgaat | cccactcgcg | aaaatggccg | ttgccgaatc | cggcatgggt | 180 |
| atcgtcgaag | ataaagtgat | caaaaaccac | tttgcttctg | aatatatcta | caacgcctat | 240 |
| aaagatgaaa | aaacctgtgg | tgttctgtct | gaagacgaca | cttttggtac | catcactatc | 300 |
| gctgaaccaa | tcggtattat | ttgcggtatc | gttccgacca | ctaacccgac | ttcaactgct | 360 |
| atcttcaaat | cgctgatcag | tctgaagacc | cgtaacgcca | ttatcttctc | cccgcacccg | 420 |
| cgtgcaaaag | atgccaccaa | caaagcggct | gatatcgttc | tgcaggctgc | tatcgctgcc | 480 |
| ggtgctccga | agatctgat | cggctggatc | gatcaacctt | ctgttgaact | gtctaacgca | 540 |
| ctgatgcacc | acccagacat | caacctgatc | ctcgcgactg | tggtccgggg | catggttaaa | 600 |
| gccgcataca | gctccggtaa | accagctatc | ggtgtaggcg | cgggcaacac | tccagttgtt | 660 |
| atcgatgaaa | ctgctgatat | caaacgtgca | gttgcatctg | tactgatgtc | caaaaccttc | 720 |
| gacaacggcg | taatctgtgc | ttctgaacag | tctgttgttg | ttgttgactc | tgtttatgac | 780 |
| gctgtacgtg | aacgttttgc | aacccacggc | ggctatctgt | tgcagggtaa | agagctgaaa | 840 |
| gctgttcagg | atgttatcct | gaaaaacggt | gcgctgaacg | cggctatcgt | tggtcagcca | 900 |
| gcctataaaa | ttgctgaact | ggcaggcttc | tctgtaccag | aaaacaccaa | gattctgatc | 960 |
| ggtgaagtga | ccgttgttga | tgaaagcgaa | ccgttcgcac | atgaaaaact | gtccccgact | 1020 |
| ctggcaatgt | accgcgctaa | agatttcgaa | gacgcggtag | aaaaagcaga | gaaactggtt | 1080 |
| gctatgggcg | gtatcggtca | tacctcttgc | ctgtacactg | accaggataa | ccaaccggct | 1140 |
| cgcgtttctt | acttcggtca | gaaaatgaaa | acggcgcgta | tcctgattaa | cacccccagcg | 1200 |
| tctcagggtg | gtatcggtga | cctgtataac | ttcaaactcg | caccttccct | gactctgggt | 1260 |
| tgtggttctt | ggggtggtaa | ctccatctct | gaaaacgttg | gtccgaaaca | cctgatcaac | 1320 |
| aagaaaaccg | ttgctaagcg | agctgaaaac | atgttgtggc | acaaacttcc | gaaatctatc | 1380 |
| tacttccgcc | gtggctccct | gccaatcgcg | ctggatgaag | tgattactga | tggccacaaa | 1440 |
| cgtgcgctca | tcgtgactga | ccgcttcctg | ttcaacaatg | ttatgctga | tcagatcact | 1500 |
| tccgtactga | aagcagcagg | cgttgaaact | gaagtcttct | cgaagtaga | agcggacccg | 1560 |
| accctgagca | tcgttcgtaa | aggtgcagaa | ctggcaaact | ccttcaaacc | agacgtgatt | 1620 |
| atcgcgctgg | gtggtggttc | cccgatggac | gccgcgaaga | tcatgtgggt | tatgtacgaa | 1680 |
| catccggaaa | ctcacttcga | agagctggcg | ctgcgcttta | tggatatccg | taaacgtatc | 1740 |
| tacaagttcc | cgaaaatggg | cgtgaaagcg | aaaatgatcg | ctgtcaccac | cacttctggt | 1800 |
| acaggttctg | aagtcactcc | gtttgcggtt | gtaactgacg | acgctactgg | tcagaaatat | 1860 |
| ccgctggcag | actatgcgct | gactccggat | atggcgattg | tcgacgccaa | cctggttatg | 1920 |
| gacatgccga | agtccctgtg | tgctttcggt | ggtctggacg | cagtaactca | cgccatggaa | 1980 |
| gcttatgttt | ctgtactggc | atctgagttc | tctgatggtc | aggctctgca | ggcactgaaa | 2040 |
| ctgctgaaag | aatatctgcc | agcgtcctac | cacgaagggt | ctaaaaatcc | ggtagcgcgt | 2100 |
| gaacgtgttc | acagtgcagc | gactatcgcg | ggtatcgcgt | ttgcgaacgc | cttcctgggt | 2160 |
| gtatgtcact | caatggcgca | caaactgggt | tcccagttcc | atattccgca | cggtctggca | 2220 |

```
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctggaaa cgctgaaagc tgaactgggt attccgaaat ctatccgtga agctggcgtt    2460
caggaagcag acttcctggc gaacgtggat aaactgtctg aagatgcatt cgatgaccag    2520
tgcaccggcg ctaacccgcg ttacccgctg atctccgagc tgaaacagat tctgctggat    2580
acctactacg gtcgtgatta tgtagaaggt gaaactgcag cgaagaaaga agctgctccg    2640
gctaaagctg agaaaaaagc gaaaaaatcc gcttaa                              2676
```

<210> SEQ ID NO 76
<211> LENGTH: 329
<212> TYPE: PRT
<213> ORGANISM: Escherichia coli

<400> SEQUENCE: 76

```
Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Val Phe Arg Arg Leu Ser Ala Cys His
        275                 280                 285
```

Asn Val Leu Phe Thr Gly His Gln Ala Phe Leu Thr Ala Glu Ala Leu
        290                 295                 300
Thr Ser Ile Ser Gln Thr Thr Leu Gln Asn Leu Ser Asn Leu Glu Lys
305                 310                 315                 320
Gly Glu Thr Cys Pro Asn Glu Leu Val
                325

<210> SEQ ID NO 77
<211> LENGTH: 990
<212> TYPE: DNA
<213> ORGANISM: Escherichia coli

<400> SEQUENCE: 77
atgaaactcg ccgtttatag cacaaaacag tacgacaaga agtacctgca acaggtgaac    60
gagtcctttg gctttgagct ggaattttttt gactttctgc tgacggaaaa aaccgctaaa   120
actgccaatg gctgcgaagc ggtatgtatt ttcgtaaacg atgacggcag ccgcccggtg   180
ctggaagagc tgaaaaagca cggcgttaaa tatatcgccc tgcgctgtgc cggtttcaat   240
aacgtcgacc ttgacgcggc aaaagaactg gggctgaaag tagtccgtgt tccagcctat   300
gatccagagg ccgttgctga acacgccatc ggtatgatga tgacgctgaa ccgccgtatt   360
caccgcgcgt atcagcgtac ccgtgatgct aacttctctc tggaaggtct gaccggcttt   420
actatgtatg caaaacggc aggcgttatc ggtaccggta aaatcggtgt ggcgatgctg   480
cgcattctga aggttttgg tatgcgtctg ctggcgttcg atccgtatcc aagtgcagcg   540
gcgctggaac tcggtgtgga gtatgtcgat ctgccaaccc tgttctctga atcagacgtt   600
atctctctgc actgcccgct gacaccggaa actatcatc tgttgaacga agccgccttc   660
gaacagatga aaaatggcgt gatgatcgtc aataccagtc gcggtgcatt gattgattct   720
caggcagcaa ttgaagcgct gaaaaatcag aaaattggtt cgttgggtat ggacgtgtat   780
gagaacgaac gcgatctatt ctttgaagat aaatccaacg acgtgatcca ggatgacgta   840
ttccgtcgcc tgtctgcctg ccacaacgtg ctgtttaccg gcaccaggc attcctgaca   900
gcagaagctc tgaccagtat ttctcagact acgctgcaaa acttaagcaa tctggaaaaa   960
ggcgaaacct gcccgaacga actggtttaa                                    990

<210> SEQ ID NO 78
<211> LENGTH: 24
<212> TYPE: DNA
<213> ORGANISM: artificial sequence
<220> FEATURE:
<223> OTHER INFORMATION: primer

<400> SEQUENCE: 78
tcatcactga taacctgatt ccgg                                           24

<210> SEQ ID NO 79
<211> LENGTH: 26
<212> TYPE: DNA
<213> ORGANISM: artificial sequence
<220> FEATURE:
<223> OTHER INFORMATION: primer

<400> SEQUENCE: 79
cgagtctgtt ttggcagtca ccttaa                                         26

<210> SEQ ID NO 80
<211> LENGTH: 23
<212> TYPE: DNA

```
<213> ORGANISM: artificial sequence
<220> FEATURE:
<223> OTHER INFORMATION: primer

<400> SEQUENCE: 80
gagcgtgacg acgtcaactt cct                                              23

<210> SEQ ID NO 81
<211> LENGTH: 23
<212> TYPE: DNA
<213> ORGANISM: artificial sequence
<220> FEATURE:
<223> OTHER INFORMATION: primer

<400> SEQUENCE: 81
cagttcaatg ctgaaccaca cag                                              23

<210> SEQ ID NO 82
<211> LENGTH: 23
<212> TYPE: DNA
<213> ORGANISM: artificial sequence
<220> FEATURE:
<223> OTHER INFORMATION: primer

<400> SEQUENCE: 82
gaaggttgcg cctacactaa gca                                              23

<210> SEQ ID NO 83
<211> LENGTH: 23
<212> TYPE: DNA
<213> ORGANISM: artificial sequence
<220> FEATURE:
<223> OTHER INFORMATION: primer

<400> SEQUENCE: 83
gggagcggca agattaaacc agt                                              23

<210> SEQ ID NO 84
<211> LENGTH: 23
<212> TYPE: DNA
<213> ORGANISM: artificial sequence
<220> FEATURE:
<223> OTHER INFORMATION: primer

<400> SEQUENCE: 84
tggatcacgt aatcagtacc cag                                              23

<210> SEQ ID NO 85
<211> LENGTH: 23
<212> TYPE: DNA
<213> ORGANISM: artificial sequence
<220> FEATURE:
<223> OTHER INFORMATION: primer

<400> SEQUENCE: 85
atccttaact gatcggcatt gcc                                              23

<210> SEQ ID NO 86
<211> LENGTH: 30
<212> TYPE: DNA
<213> ORGANISM: artificial sequence
<220> FEATURE:
<223> OTHER INFORMATION: primer

<400> SEQUENCE: 86
ggaattcaca catgaaagct ctggtttatc                                       30
```

<210> SEQ ID NO 87
<211> LENGTH: 28
<212> TYPE: DNA
<213> ORGANISM: artificial sequence
<220> FEATURE:
<223> OTHER INFORMATION: primer

<400> SEQUENCE: 87
gcgtccaggg cgtcaaagat caggcagc                28

<210> SEQ ID NO 88
<211> LENGTH: 30
<212> TYPE: DNA
<213> ORGANISM: artificial sequence
<220> FEATURE:
<223> OTHER INFORMATION: primer

<400> SEQUENCE: 88
gacctaggag gtcacacatg aaagctctgg              30

<210> SEQ ID NO 89
<211> LENGTH: 25
<212> TYPE: DNA
<213> ORGANISM: artificial sequence
<220> FEATURE:
<223> OTHER INFORMATION: primer

<400> SEQUENCE: 89
cgactctaga ggatccccgg gtacc                   25

<210> SEQ ID NO 90
<211> LENGTH: 602
<212> TYPE: PRT
<213> ORGANISM: Escherichia coli

<400> SEQUENCE: 90

Met Gln Thr Phe Gln Ala Asp Leu Ala Ile Val Gly Ala Gly Gly Ala
1               5                   10                  15

Gly Leu Arg Ala Ala Ile Ala Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala

```
              180                 185                 190
Thr Gly Gly Ala Gly Arg Val Tyr Arg Tyr Asn Thr Asn Gly Gly Ile
            195                 200                 205
Val Thr Gly Asp Gly Met Gly Met Ala Leu Ser His Gly Val Pro Leu
        210                 215                 220
Arg Asp Met Glu Phe Val Gln Tyr His Pro Thr Gly Leu Pro Gly Ser
225                 230                 235                 240
Gly Ile Leu Met Thr Glu Gly Cys Arg Gly Glu Gly Gly Ile Leu Val
                245                 250                 255
Asn Lys Asn Gly Tyr Arg Tyr Leu Gln Asp Tyr Gly Met Gly Pro Glu
            260                 265                 270
Thr Pro Leu Gly Glu Pro Lys Asn Lys Tyr Met Glu Leu Gly Pro Arg
        275                 280                 285
Asp Lys Val Ser Gln Ala Phe Trp His Glu Trp Arg Lys Gly Asn Thr
290                 295                 300
Ile Ser Thr Pro Arg Gly Asp Val Val Tyr Leu Asp Leu Arg His Leu
305                 310                 315                 320
Gly Glu Lys Lys Leu His Glu Arg Leu Pro Phe Ile Cys Glu Leu Ala
                325                 330                 335
Lys Ala Tyr Val Gly Val Asp Pro Val Lys Glu Pro Ile Pro Val Arg
            340                 345                 350
Pro Thr Ala His Tyr Thr Met Gly Gly Ile Glu Thr Asp Gln Asn Cys
        355                 360                 365
Glu Thr Arg Ile Lys Gly Leu Phe Ala Val Gly Glu Cys Ser Ser Val
    370                 375                 380
Gly Leu His Gly Ala Asn Arg Leu Gly Ser Asn Ser Leu Ala Glu Leu
385                 390                 395                 400
Val Val Phe Gly Arg Leu Ala Gly Glu Gln Ala Thr Glu Arg Ala Ala
                405                 410                 415
Thr Ala Gly Asn Gly Asn Glu Ala Ala Ile Glu Ala Gln Ala Ala Gly
            420                 425                 430
Val Glu Gln Arg Leu Lys Asp Leu Val Asn Gln Asp Gly Gly Glu Asn
        435                 440                 445
Trp Ala Lys Ile Arg Asp Glu Met Gly Leu Ala Met Glu Glu Gly Cys
    450                 455                 460
Gly Ile Tyr Arg Thr Pro Glu Leu Met Gln Lys Thr Ile Asp Lys Leu
465                 470                 475                 480
Ala Glu Leu Gln Glu Arg Phe Lys Arg Val Arg Ile Thr Asp Thr Ser
                485                 490                 495
Ser Val Phe Asn Thr Asp Leu Leu Tyr Thr Ile Glu Leu Gly His Gly
            500                 505                 510
Leu Asn Val Ala Glu Cys Met Ala His Ser Ala Met Ala Arg Lys Glu
        515                 520                 525
Ser Arg Gly Ala His Gln Arg Leu Asp Glu Gly Cys Thr Glu Arg Asp
    530                 535                 540
Asp Val Asn Phe Leu Lys His Thr Leu Ala Phe Arg Asp Ala Asp Gly
545                 550                 555                 560
Thr Thr Arg Leu Glu Tyr Ser Asp Val Lys Ile Thr Thr Leu Pro Pro
                565                 570                 575
Ala Lys Arg Val Tyr Gly Gly Glu Ala Asp Ala Ala Asp Lys Ala Glu
            580                 585                 590
Ala Ala Asn Lys Lys Glu Lys Ala Asn Gly
        595                 600
```

<210> SEQ ID NO 91
<211> LENGTH: 1809
<212> TYPE: DNA
<213> ORGANISM: Escherichia coli

<400> SEQUENCE: 91

| | | | | | |
|---|---|---|---|---|---|
| gtgcaaacct | ttcaagccga | tcttgccatt | gtaggcgccg | gtggcgcggg | attacgtgct | 60 |
| gcaattgctg | ccgcgcaggc | aaatccgaat | gcaaaaatcg | cactaatctc | aaaagtatac | 120 |
| ccgatgcgta | gccataccgt | tgctgcagaa | ggggctccg | ccgctgtcgc | gcaggatcat | 180 |
| gacagcttcg | aatatcactt | tcacgataca | gtagcgggtg | gcgactggtt | gtgtgagcag | 240 |
| gatgtcgtgg | attatttcgt | ccaccactgc | ccaaccgaaa | tgacccaact | ggaactgtgg | 300 |
| ggatgcccat | ggagccgtcg | cccggatggt | agcgtcaacg | tacgtcgctt | cggcggcatg | 360 |
| aaaatcgagc | gcacctggtt | cgccgccgat | aagaccggct | tccatatgct | gcacacgctg | 420 |
| ttccagacct | ctctgcaatt | cccgcagatc | cagcgttttg | acgaacattt | cgtgctggat | 480 |
| attctggttg | atgatggtca | tgttcgcggc | ctggtagcaa | tgaacatgat | ggaaggcacg | 540 |
| ctggtgcaga | tccgtgctaa | cgcggtcgtt | atggctactg | gcggtgcggg | tcgcgtttat | 600 |
| cgttacaaca | ccaacggcgg | catcgttacc | ggtgacggta | tgggtatggc | gctaagccac | 660 |
| ggcgttccgc | tgcgtgacat | ggaattcgtt | cagtatcacc | caaccggtct | gccaggttcc | 720 |
| ggtatcctga | tgaccgaagg | ttgccgcggt | gaaggcggta | ttctggtcaa | caaaaatggc | 780 |
| taccgttatc | tgcaagatta | cggcatgggc | ccggaaactc | cgctgggcga | ccgaaaaac | 840 |
| aaatatatgg | aactgggtcc | acgcgacaaa | gtctctcagg | ccttctggca | cgaatggcgt | 900 |
| aaaggcaaca | ccatctccac | gccgcgtggc | gatgtggttt | atctcgactt | gcgtcacctc | 960 |
| ggcgagaaaa | aactgcatga | acgtctgccg | ttcatctgcg | aactggcgaa | agcgtacgtt | 1020 |
| ggcgtcgatc | cggttaaaga | accgattccg | gtacgtccga | ccgcacacta | ccatgggc | 1080 |
| ggtatcgaaa | ccgatcagaa | ctgtgaaacc | cgcattaaag | gtctgttcgc | cgtgggtgaa | 1140 |
| tgttcctctg | ttggtctgca | cggtgcaaac | cgtctgggtt | ctaactccct | ggcggaactg | 1200 |
| gtggtcttcg | gccgtctggc | cggtgaacaa | gcgacagagc | gtgcagcaac | tgccggtaat | 1260 |
| ggcaacgaag | cggcaattga | agcgcaggca | gctggcgttg | aacaacgtct | gaaagatctg | 1320 |
| gttaaccagg | atggcggcga | aaactggcg | aagatccgcg | acgaaatggg | cctggctatg | 1380 |
| gaagaaggct | gcggtatcta | ccgtacgccg | gaactgatgc | agaaaaccat | cgacaagctg | 1440 |
| gcagagctgc | aggaacgctt | caagcgcgtg | cgcatcaccg | acacttccag | cgtgttcaac | 1500 |
| accgacctgc | tctacaccat | tgaactgggc | cacggtctga | cgttgctga | atgtatggcg | 1560 |
| cactccgcaa | tggcacgtaa | agagtcccgc | ggcgcgcacc | agcgtctgga | cgaaggttgc | 1620 |
| accgagcgtg | acgacgtcaa | cttcctcaaa | cacaccctcg | ccttccgcga | tgctgatggc | 1680 |
| acgactcgcc | tggagtacag | cgacgtgaag | attactacgc | tgccgccagc | taaacgcgtt | 1740 |
| tacggtggcg | aagcggatgc | agccgataag | gcggaagcag | ccaataagaa | ggagaaggcg | 1800 |
| aatggctga | | | | | | 1809 |

<210> SEQ ID NO 92
<211> LENGTH: 131
<212> TYPE: PRT
<213> ORGANISM: Escherichia coli

<400> SEQUENCE: 92

Met Thr Thr Lys Arg Lys Pro Tyr Val Arg Pro Met Thr Ser Thr Trp
1               5                   10                  15

Trp Lys Lys Leu Pro Phe Tyr Arg Phe Tyr Met Leu Arg Glu Gly Thr
                20                  25                  30

Ala Val Pro Ala Val Trp Phe Ser Ile Glu Leu Ile Phe Gly Leu Phe
            35                  40                  45

Ala Leu Lys Asn Gly Pro Glu Ala Trp Ala Gly Phe Val Asp Phe Leu
        50                  55                  60

Gln Asn Pro Val Ile Val Ile Asn Leu Ile Thr Leu Ala Ala Ala
65                  70                  75                  80

Leu Leu His Thr Lys Thr Trp Phe Glu Leu Ala Pro Lys Ala Ala Asn
                85                  90                  95

Ile Ile Val Lys Asp Glu Lys Met Gly Pro Glu Pro Ile Ile Lys Ser
            100                 105                 110

Leu Trp Ala Val Thr Val Val Ala Thr Ile Val Ile Leu Phe Val Ala
        115                 120                 125

Leu Tyr Trp
    130

<210> SEQ ID NO 93
<211> LENGTH: 396
<212> TYPE: DNA
<213> ORGANISM: Escherichia coli

<400> SEQUENCE: 93
atgacgacta aacgtaaacc gtatgtacgg ccaatgacgt ccacctggtg gaaaaaattg     60 ccgtttttatc gcttttacat gctgcgcgaa ggcacggcgg ttccggctgt gtggttcagc   120
attgaactga ttttcgggct gtttgccctg aaaaatggcc cggaagcctg gcgggattc    180 gtcgactttt tacaaaaccc ggttatcgtg atcattaacc tgatcactct ggcggcagct   240
ctgctgcaca ccaaaacctg gtttgaactg gcaccgaaag cggccaatat cattgtaaaa   300
gacgaaaaaa tgggaccaga gccaattatc aaaagtctct gggcggtaac tgtggttgcc   360
accatcgtaa tcctgtttgt tgccctgtac tggtaa                              396

<210> SEQ ID NO 94
<211> LENGTH: 119
<212> TYPE: PRT
<213> ORGANISM: Escherichia coli

<400> SEQUENCE: 94

Met Ile Asn Pro Asn Pro Lys Arg Ser Asp Glu Pro Val Phe Trp Gly
1               5                   10                  15

Leu Phe Gly Ala Gly Gly Met Trp Ser Ala Ile Ile Ala Pro Val Met
                20                  25                  30

Ile Leu Leu Val Gly Ile Leu Leu Pro Leu Gly Leu Phe Pro Gly Asp
            35                  40                  45

Ala Leu Ser Tyr Glu Arg Val Leu Ala Phe Ala Gln Ser Phe Ile Gly
        50                  55                  60

Arg Val Phe Leu Phe Leu Met Ile Val Leu Pro Leu Trp Cys Gly Leu
65                  70                  75                  80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
            100                 105                 110

Leu Ile Gly Val Val Thr Ile

```
                          115

<210> SEQ ID NO 95
<211> LENGTH: 360
<212> TYPE: DNA
<213> ORGANISM: Escherichia coli

<400> SEQUENCE: 95
atgattaatc caaatccaaa gcgttctgac gaaccggtat tctggggcct cttcggggcc      60
ggtggtatgt ggagcgccat cattgcgccg gtgatgatcc tgctggtggg tattctgctg     120
ccactggggt tgtttccggg tgatgcgctg agctacgagc gcgttctggc gttcgcgcag     180
agcttcattg gtcgcgtatt cctgttcctg atgatcgttc tgccgctgtg gtgtggttta     240
caccgtatgc accacgcgat gcacgatctg aaaatccacg tacctgcggg caaatgggtt     300
ttctacggtc tggctgctat cctgacagtt gtcacgctga ttggtgtcgt tacaatctaa     360
```